US011116902B2

(12) United States Patent
El-Khatib et al.

(10) Patent No.: US 11,116,902 B2
(45) Date of Patent: Sep. 14, 2021

(54) BLOOD GLUCOSE CONTROL SYSTEM WITH CONTROL PARAMETER MODIFICATION

(71) Applicant: BETA BIONICS, INC., Concord, MA (US)

(72) Inventors: Firas H. El-Khatib, Allston, MA (US); Edward R. Damiano, Acton, MA (US)

(73) Assignee: Beta Bionics, Inc., Concord, MA (US)

( * ) Notice: Subject to any disclaimer, the term of this patent is extended or adjusted under 35 U.S.C. 154(b) by 0 days.

(21) Appl. No.: 17/061,927

(22) Filed: Oct. 2, 2020

(65) Prior Publication Data

US 2021/0016004 A1 Jan. 21, 2021

Related U.S. Application Data

(63) Continuation-in-part of application No. PCT/US2020/042269, filed on Jul. 16, 2020, which is
(Continued)

(51) Int. Cl.
*A61M 5/172* (2006.01)
*G16H 20/17* (2018.01)
(Continued)

(52) U.S. Cl.
CPC ...... *A61M 5/1723* (2013.01); *A61M 5/14244* (2013.01); *G16H 10/40* (2018.01);
(Continued)

(58) Field of Classification Search
CPC .... A61M 5/1723; A61M 5/172; A61M 5/168; A61M 5/14; A61M 5/14244;
(Continued)

(56) References Cited

U.S. PATENT DOCUMENTS

| 4,280,494 A | 7/1981 | Cosgrove et al. |
| 4,464,170 A | 8/1984 | Clemens et al. |

(Continued)

FOREIGN PATENT DOCUMENTS

| CN | 1973768 | 6/2007 |
| CN | 201186082 | 1/2009 |

(Continued)

OTHER PUBLICATIONS

Albisser et al., May 1974, An Artificial Endocrine Pancreas, Diabetes, 23(5):389-396.
(Continued)

*Primary Examiner* — Jason E Flick
(74) *Attorney, Agent, or Firm* — Knobbe Martens Olson & Bear, LLP

(57) ABSTRACT

A blood glucose control system is configured to modify therapy provided to a subject. The system can cause first therapy to be delivered by the blood glucose control system to a subject during a first therapy period. The first therapy can be delivered based at least in part on a first value of a control parameter used by a control algorithm to generate a dose control signal. The system can determine a first effect corresponding at least in part to the first therapy and autonomously generate a second value of the control parameter. The system can cause second therapy to be delivered by the blood glucose control system to the subject during a second therapy period, wherein the second therapy is delivered based at least in part on the second value of the control parameter.

29 Claims, 22 Drawing Sheets

Related U.S. Application Data a continuation-in-part of application No. PCT/US2020/042195, filed on Jul. 15, 2020, which is a continuation-in-part of application No. PCT/US2020/042198, filed on Jul. 15, 2020.

(60) Provisional application No. 62/874,928, filed on Jul. 16, 2019, provisional application No. 62/874,934, filed on Jul. 16, 2019, provisional application No. 62/874,950, filed on Jul. 16, 2019, provisional application No. 62/874,954, filed on Jul. 16, 2019, provisional application No. 62/874,959, filed on Jul. 16, 2019, provisional application No. 62/874,964, filed on Jul. 16, 2019, provisional application No. 62/874,968, filed on Jul. 16, 2019, provisional application No. 62/874,972, filed on Jul. 16, 2019, provisional application No. 62/874,975, filed on Jul. 16, 2019, provisional application No. 62/874,977, filed on Jul. 16, 2019, provisional application No. 62/910,970, filed on Oct. 4, 2019, provisional application No. 62/911,017, filed on Oct. 4, 2019, provisional application No. 62/911,143, filed on Oct. 4, 2019, provisional application No. 62/987,842, filed on Mar. 10, 2020, provisional application No. 63/037,472, filed on Jun. 10, 2020.

(51) Int. Cl.
*G16H 10/40* (2018.01)
*G16H 20/60* (2018.01)
*A61M 5/142* (2006.01)
*G16H 40/67* (2018.01)

(52) U.S. Cl.
CPC .............. *G16H 20/17* (2018.01); *G16H 20/60* (2018.01); *G16H 40/67* (2018.01); *A61M 2005/14208* (2013.01); *A61M 2005/1726* (2013.01); *A61M 2205/16* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2230/201* (2013.01)

(58) Field of Classification Search
CPC ........ A61M 5/142; A61M 2005/14208; A61M 2005/1726; A61M 2230/201; A61M 2230/20; A61M 2230/00
See application file for complete search history.

(56) References Cited

U.S. PATENT DOCUMENTS

| | | | |
|---|---|---|---|
| 5,665,065 A | 9/1997 | Colman | |
| 6,544,212 B2 | 4/2003 | Galley et al. | |
| 6,554,798 B1 | 4/2003 | Mann et al. | |
| 6,572,542 B1 | 6/2003 | Houben | |
| 7,347,836 B2 | 3/2008 | Peterson | |
| 7,491,187 B2 | 2/2009 | Van Den Berghe et al. | |
| 7,651,845 B2 | 1/2010 | Doyle, III et al. | |
| 7,655,618 B2 | 2/2010 | Green et al. | |
| 7,678,762 B2 | 3/2010 | Green et al. | |
| 7,678,763 B2 | 3/2010 | Green et al. | |
| 7,683,027 B2 | 3/2010 | Green et al. | |
| 7,766,829 B2 | 8/2010 | Sloan et al. | |
| 7,806,854 B2 | 10/2010 | Damiano et al. | |
| 7,850,641 B2 | 12/2010 | Lebel et al. | |
| 8,273,052 B2 | 9/2012 | Damiano et al. | |
| 8,348,842 B1 | 1/2013 | Osorio | |
| 8,377,031 B2 | 2/2013 | Hayter et al. | |
| 8,454,510 B2 | 6/2013 | Yodfat et al. | |
| 8,457,901 B2 | 6/2013 | Beshan | |
| 8,478,557 B2 | 7/2013 | Hayter | |
| 8,562,587 B2 | 10/2013 | Kovatchev et al. | |
| 8,622,988 B2 | 1/2014 | Hayter | |
| 8,679,016 B2 | 3/2014 | Mastrototaro et al. | |
| 8,690,820 B2 | 4/2014 | Cinar | |
| 8,840,582 B2 | 9/2014 | Blomquist et al. | |
| 9,283,323 B2 | 3/2016 | Toumazou | |
| 9,351,670 B2 | 5/2016 | Dunn | |
| 9,398,869 B2 | 7/2016 | Kovatchev et al. | |
| 9,445,757 B2 | 9/2016 | Desborough | |
| 9,486,578 B2 | 11/2016 | Finan | |
| 9,750,438 B2 | 9/2017 | Kovatchev et al. | |
| 9,833,570 B2 | 12/2017 | El-Khatib et al. | |
| 9,839,395 B2* | 12/2017 | Shariati | G16H 20/17 |
| 9,901,677 B2 | 2/2018 | Estes | |
| 9,907,909 B2 | 3/2018 | Finan | |
| 9,999,728 B2 | 6/2018 | Parikh | |
| 10,188,793 B2 | 1/2019 | Mazlish | |
| 10,188,795 B2 | 1/2019 | El-Khatib et al. | |
| 10,357,607 B2 | 7/2019 | Blomquist et al. | |
| 10,463,786 B2 | 11/2019 | Saint | |
| 10,543,313 B2 | 1/2020 | Damiano et al. | |
| 10,569,016 B2 | 2/2020 | Rosinko | |
| 10,653,834 B2 | 5/2020 | Kruse et al. | |
| 10,842,934 B2 | 11/2020 | El-Khatib et al. | |
| 10,940,267 B2 | 3/2021 | El-Khatib | |
| 10,960,137 B2 | 3/2021 | El-Khatib et al. | |
| 2003/0181852 A1 | 9/2003 | Mann et al. | |
| 2004/0028707 A1 | 2/2004 | Pinkerton | |
| 2004/0034295 A1 | 2/2004 | Salganicoff | |
| 2004/0147872 A1 | 7/2004 | Thompson | |
| 2004/0253736 A1 | 12/2004 | Stout et al. | |
| 2005/0018633 A1 | 1/2005 | Kovachev et al. | |
| 2005/0182366 A1 | 8/2005 | Vogt et al. | |
| 2005/0272640 A1 | 12/2005 | Doyle, III et al. | |
| 2006/0276771 A1 | 2/2006 | Gally | |
| 2006/0272652 A1 | 12/2006 | Stocker | |
| 2007/0282299 A1 | 12/2007 | Hellwig | |
| 2008/0154187 A1 | 6/2008 | Krulevitch | |
| 2008/0183060 A1 | 7/2008 | Steil et al. | |
| 2008/0208113 A1 | 8/2008 | Damiano et al. | |
| 2008/0269714 A1 | 10/2008 | Mastrototaro | |
| 2008/0319384 A1 | 12/2008 | Yodfat et al. | |
| 2009/0006061 A1 | 1/2009 | Thukral et al. | |
| 2009/0036753 A1 | 2/2009 | King | |
| 2009/0164239 A1 | 6/2009 | Hayter et al. | |
| 2009/0177154 A1 | 7/2009 | Blomquist | |
| 2010/0057057 A1* | 3/2010 | Hayter | A61B 5/4839 604/890.1 |
| 2010/0082167 A1 | 4/2010 | Haueter | |
| 2010/0125241 A1 | 5/2010 | Prud'homme et al. | |
| 2010/0137788 A1 | 6/2010 | Braithwaite et al. | |
| 2010/0145262 A1 | 6/2010 | Bengtsson | |
| 2010/0256466 A1 | 10/2010 | Shekalim | |
| 2010/0262117 A1 | 10/2010 | Magni et al. | |
| 2010/0292634 A1 | 11/2010 | Kircher, Jr. | |
| 2011/0021898 A1 | 1/2011 | Wei et al. | |
| 2011/0054391 A1 | 3/2011 | Ward et al. | |
| 2011/0208155 A1 | 8/2011 | Palerm et al. | |
| 2011/0208156 A1 | 8/2011 | Doyle, III et al. | |
| 2012/0065894 A1 | 3/2012 | Tubb et al. | |
| 2012/0078067 A1 | 3/2012 | Kovatchev et al. | |
| 2012/0245556 A1 | 9/2012 | Kovatchev et al. | |
| 2012/0246106 A1 | 9/2012 | Atlas et al. | |
| 2012/0265126 A1 | 10/2012 | Estes | |
| 2012/0265722 A1 | 10/2012 | Blomquist | |
| 2012/0277723 A1 | 11/2012 | Skladnev | |
| 2012/0283694 A1 | 11/2012 | Yodfat et al. | |
| 2013/0190583 A1 | 7/2013 | Grosman | |
| 2014/0031786 A1 | 1/2014 | Kircher, Jr. et al. | |
| 2014/0039455 A1 | 2/2014 | Miller et al. | |
| 2015/0217052 A1 | 8/2015 | Keenan et al. | |
| 2015/0217053 A1 | 8/2015 | Booth | |
| 2016/0224756 A1 | 8/2016 | Berger | |
| 2016/0331898 A1 | 11/2016 | Damiano | |
| 2017/0095612 A1 | 4/2017 | El-Khatib et al. | |
| 2017/0189614 A1 | 7/2017 | Mazlish et al. | |

(56) References Cited

U.S. PATENT DOCUMENTS

| | | |
|---|---|---|
| 2017/0203038 A1 | 7/2017 | Desborough et al. |
| 2018/0185587 A1 | 7/2018 | Brauker |
| 2018/0200435 A1 | 7/2018 | Mazlish et al. |
| 2018/0200440 A1 | 7/2018 | Mazlish et al. |
| 2019/0214124 A1 | 7/2019 | Mougiakakou |
| 2019/0247578 A1 | 8/2019 | Desborough |
| 2019/0336684 A1 | 11/2019 | O'Connor |
| 2020/0254240 A1* | 8/2020 | Windmiller ............ A61N 1/30 |
| 2021/0085869 A1 | 3/2021 | El-Khatib et al. |

FOREIGN PATENT DOCUMENTS

| | | |
|---|---|---|
| CN | 101795623 | 8/2010 |
| CN | 102667787 | 9/2012 |
| CN | 104667368 | 8/2017 |
| CN | 104667379 | 8/2017 |
| EP | 1 575 656 | 6/2009 |
| EP | 3 453 414 | 3/2019 |
| JP | 03-500129 | 3/1989 |
| JP | 2001-204817 | 7/2001 |
| JP | 2003-079723 | 3/2003 |
| JP | 2004-502474 | 1/2004 |
| JP | 2007-529241 | 10/2007 |
| JP | 2007-312923 | 12/2007 |
| JP | 2012-516735 | 7/2012 |
| JP | 2012-519018 | 8/2012 |
| WO | WO 04/006982 | 1/2004 |
| WO | WO 04/084820 | 10/2004 |
| WO | WO 06/124716 | 11/2006 |
| WO | WO 08/057384 | 5/2008 |
| WO | WO 08/094249 | 8/2008 |
| WO | WO 08/114254 | 9/2008 |
| WO | WO 08/157780 | 12/2008 |
| WO | WO 09/001349 | 12/2008 |
| WO | WO 12/058694 | 5/2012 |
| WO | WO 14/110541 | 7/2014 |
| WO | WO 15/021041 | 2/2015 |

OTHER PUBLICATIONS

Bellazzi et al., 1995, Adaptive Controllers for Intelligent Monitoring, Artif. Intell. Med., 7:515-540.

Bellomo et al., May 1982, Optimal Feedback Glycaemia Regulation in Diabetics, Med. & Biol. Eng. & Comp. 20:329-335.

Berian et al., 2019, A wearable closed-loop insulin delivery systme based on low-power SoCs, Electronics, 8:612.

Botz, May 1976, An Improved Control Algorithm for an Artificial .beta.-Cell, IEEE Trans. Biomed. Eng., BME-23(3):252-255.

Brunetti et al., 1993, A Simulation Study on a Self-Tuning Portable Controller of Blood Glucose, Int. J. Artif. Org., 16(1):51-57.

Candas et al., Feb. 1994, An Adaptive Plasma Glucose Controller Based on a Nonlinear Insulin/Glucose Model, IEEE Trans. Biomed. Eng. 41(2):116-124.

Clemens, 1979, Feedback Control Dynamics for Glucose Controlled Insulin Infusion Systems, Med. Prog. Technol. 6:91-98.

El-Khatib et al., Apr. 14, 2010, A Bihormonal Closed-Loop Artificial Pancreas for Type 1 Diabetes, Science.Trans. Med., 2(27):1-12.

El-Khatib et al., Jul. 2009, A Feasibility Study of Bihormonal Closed-Loop Blood-Glucose Control Using Dual Subcutaneous Infusion of Insulin and Glucagon in Ambulatory Diabetic Swine, Journal of Diabetes Science and Technology, 3(4):789-803.

El-Khatib, et al., Mar. 2007, Adaptive Closed-Loop Control Provides Blood-Glucose Regulation Using Dual Subcutaneous Insulin nd Glucagon Infusion in Diabetic Swine, Journal of Diabetes Science and Technology, 1(2):181-192.

El-Khatib, et al., May 2014, Autonomous and Continuous Adaptation of a Bihormonal Bionic Pancreas in Adults and Adolescents Nilh Type 1 Diabetes, Journal of Clinical Endocrin. Melab., 99(5):1701-1711.

Femat et al., Aug. 22-27, 1999, Blood Glucose Regulation: An Output Feedback Approach, Proc. IEEE Int. Conf. Control App. pp. 1290-1293.

Fischer et al., Aug. 1987, Does Physiological Blood Glucose Control Require an Adaptive Control Strategy?, IEEE Tran. Biomed. Eng., BME-34:575-582.

Fletcher et al., 2001, Feasibility of an Implanted, Closed-Loop, Blood-Glucose Control Device, Immunology 230, Stanford University, Spring 01, 31 pp.

Furler et al., Nov.-Dec. 1985, Blood Glucose Control by Intermittent Loop Closure in the Basal Mode: Computer Simulation Studies with a Diabetic Model, Diabetes Care, 8(6):553-561.

Kan et al., 2000, Novel Control System for Blood Glucose Using a Model Predictive Method, ASAIO Journal, 4:657-662.

Lal et al., Jul. 5, 2019, Realizing a closed-loop (artifical pancreas) system for the treatment of type 1 diabetes, Endocrine reviews, 40(6):1521-1546.

Lauritzen et al., May 1983 Pharmacokinetics of Continuous Subcutaneous Insulin Infusion, Diabetologia, 24(5):326-329.

Marliss et al., Jul. 1977, Normalization of Glycemia in Diabetics During Meals with Insulin and Glucagon Delivery by the Artificial Pancreas, Diabetes, 26:663-672.

Medtronic, 2020, Minimed™ 670G Insulin Pump System, product brochure, https://www.medtronicdiabetes.com/products/minimed-670g-insulin-pump-system, 7 pp.

Pagurek et al., 1972, Adaptive Control of the Human Glucose Regulatory System, Med. Biol. Eng., 10:752-761.

Panteleon et al., Jul. 2006, Evaluation of the effect of gain on the meal response of an automated closed-loop insulin delivery system, Diabetes, 55:1995-2000.

Parker et al., 1996, Model Predictive Control for Infusion Pump Insulin Delivery, Proceedings of the 18th Annual International Conference of the IEEE, 6:1822-1823.

Parker et al., Feb. 1999, A Model-Based Algorithm for Blood Glucose Control in Type I Diabetic Patients, IEEE Trans. Biomed. Eng. 46(2):148-157.

Parker et al., Jan.-Feb. 2001, The Intravenous Route to Blood Glucose Control, IEEE Eng. Med. & Biol., pp. 65-73.

Parrish et al., Jun. 1997, Control of an Artificial Human Pancreas Using the SDRE Method, Proc. American Control Conf., 2:1059-1060.

Russell et al., Nov. 2010, Efficacy Determinants of Subcutaneous Microdose Glucagon during Closed-Loop Control, Journal of Diabetes Science and Technology, 4(6):1288-1304.

Russell, et al., Jun. 15, 2014, Outpatient Glycemic Control with a Bionic Pancreas in Type 1 Diabetes, The New England Journal of Medicine, 371(4):313-325.

Russell, et al., Nov. 2012, Blood Glucose Control in Type 1 Diabetes With a Bihormonal Bionic Endocrine Pancreas, Diabetes Care, 35:2148-2155.

Sivaramakrishnan et al., 2017, Optimal model based control for blood glucose insulin system using continuous glucose monitoring, J. Pharm. Sci & Res., 9(4):465-469.

Steil et al., 2006, Metabolic modelling and the closed-loop insulin delivery problem, Diabetes Research and Clinical Practice, 74:S183-S186.

Steil et al., Dec. 2006, Feasibility of automating insulin delivery for the treatment of type 1 diabetes, Diabetes, 55:3344-3350.

Trajanoski et al., Sep. 1998, Neural Predictive Controller for Insulin Delivery Using the Subcutaneous Route, Biomedical Engineering, 45(9):1122-1134.

International Search Report and Written Opinion dated Oct. 29, 2020 in PCT/US2020/042269.

International Search Report and Written Opinion dated Dec. 14, 2020 in PCT/US2020/054130.

Clarke et al., 2009, Statistical Tools to Analyze Continuous Glucose Monitor Data, Diabetes Technology and Therapeutics, 11:S45-S54.

University of California, San Francisco, Diabetes Education Online, Calculating Insulin Dose, https://dtc.ucsf.edu/types-of-diabetes/type2/treatment-of-type-2-diabetes/medications-and-therapies/type-2-insulin-rx/calculating-insuling-dose/, downloaded Apr. 9, 2021, 11 pp.

* cited by examiner

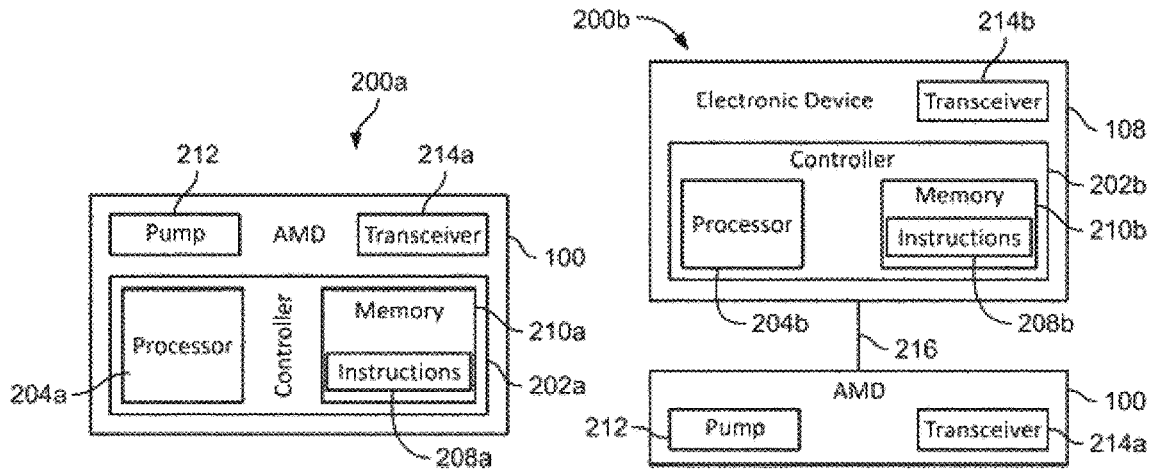
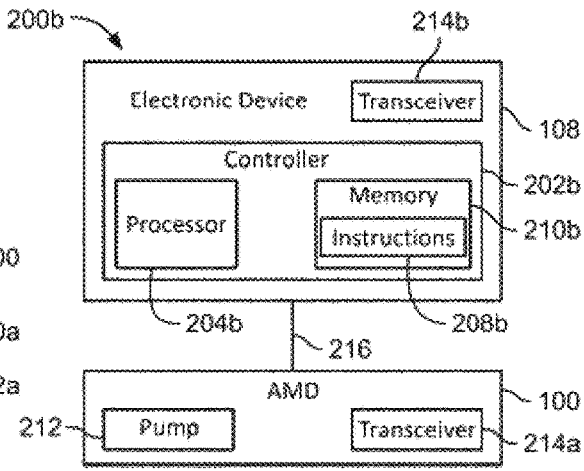
FIG. 2A
FIG. 2B
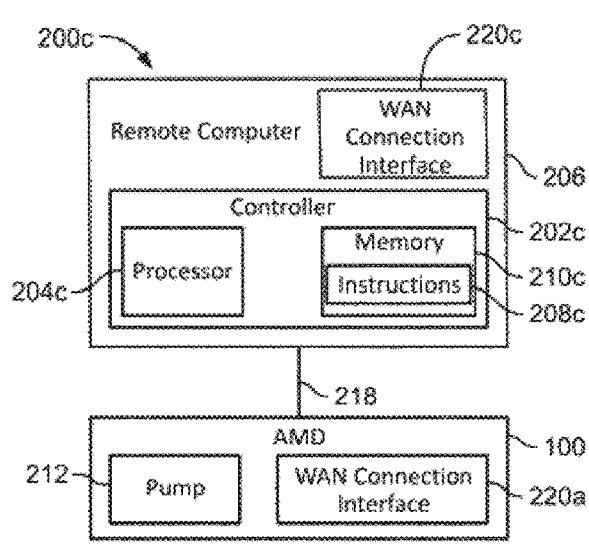
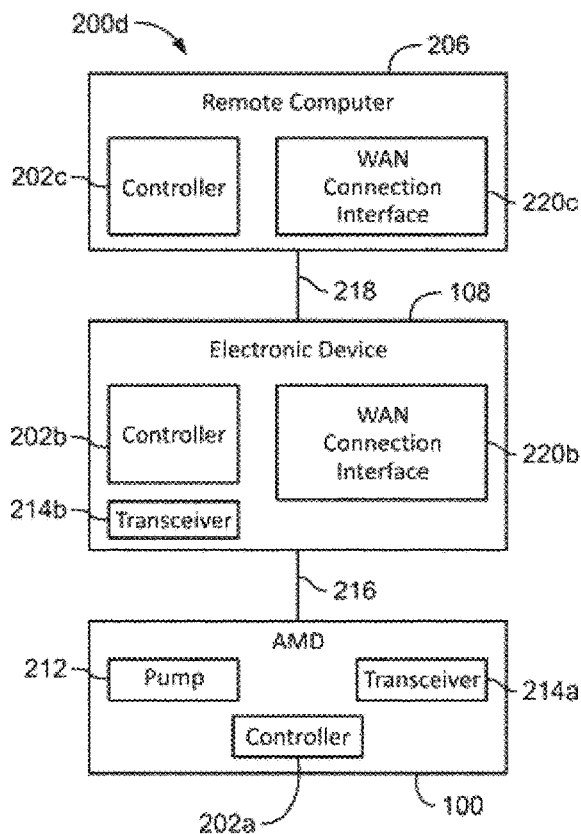
FIG. 2C
FIG. 2D

1000

| 90 Days | Saturday, January 1, 2019-Monday, March 29, 2019 |

Backup Therapy
Your glucose control system has learned your insulin needs. If your glucose control system goes offline or is temporarily unavailable, the below protocol is recommended for use for up to 72 hours.

1002

| Injections | |
|---|---|
| Usual Breakfast | 6 Units |
| Usual Lunch | 8 Units |
| Usual Dinner | 8 Units |
| Long Acting Insulin Units | 14 |
| Correction Factor mg/dL lowered per 1 Unit | 9mg/dL |

1004

| Pump Settings | |
|---|---|
| Usual Breakfast Units | 6 Units |
| Usual Lunch Units | 8 Units |
| Usual Dinner Units | 8 Units |
| Basal Rate 12:00 A.M - 6:00 A.M | .6 units per hour |
| Basal Rate 6:00 A.M - 12:00 P.M | .5 units per hour |
| Basal Rate 12:00 P.M - 6:00 P.M | .6 units per hour |
| Basal Rate 6:00 P.M - 12:00 A.M | .7 units per hour |
| Correction Factor mg/dL lowered per 1 Unit | 9 mg/dL |

Autonomous Control Summary
The autonomous control summary provides you key information about your glucose control performance during the specified time period.

1010

| 152 mg/dL Mean Glucose (CGM) | ##% Time in range 70-180 mg/dL | #.#% Time < 54 mg/dL | 4.2 Mean Meal Announcements Per Day | 45.2u Total Daily Insulin | 98% CGM Connectivity Uptime |
|---|---|---|---|---|---|
| 6.9% Estimated A1C | ##% >180 mg/dL | #.#% | | 3.2μ Total Daily Glucagon | |

FIG. 10

Ambulatory Glucose Profile (AGP)

AGP is a summary of glucose values from the report, with median (50%) and other percentiles shown as if occurring in a single day.

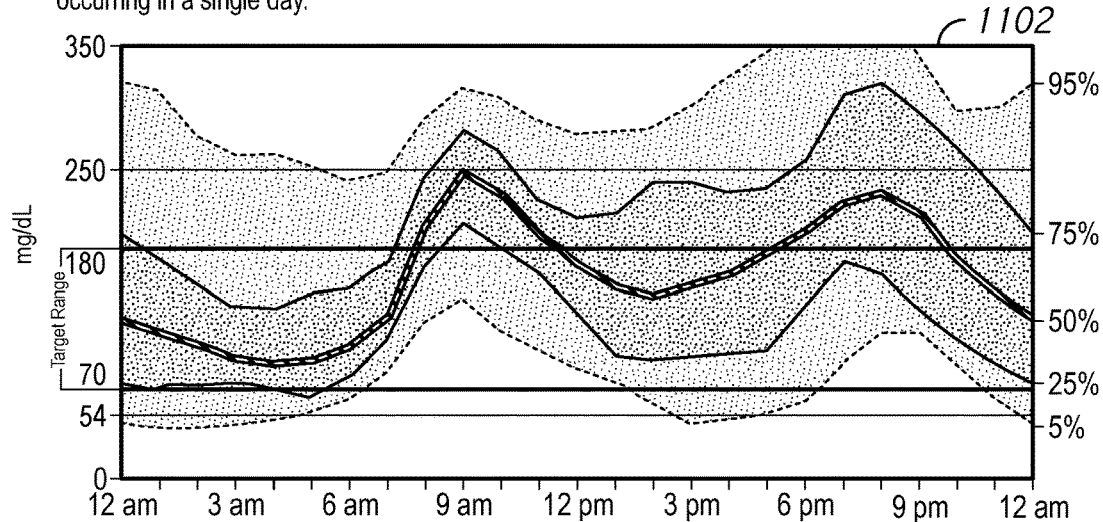

Adjustable Settings & Behavior

Settings

| | Current Entry | Previous Entry |
|---|---|---|
| Body Weight | ### pounds | ### pounds<br>last set on DD/MM/YYYY |

| Bionic Daytime Target | % time selected |
|---|---|
| Higher | ## % |
| Usual | ## % |
| Lower | ## % |

| Bionic Nightime Target | % time selected |
|---|---|
| Higher | ## % |
| Usual | ## % |
| Lower | ## % |

Bionic Temporary Targets: You set a temporary target ## times during the selected date range.
Pause Insulin: You paused insulin ## times during the selected date range.

FIG. 11

1200
Your Adjustable Behaviors
Meal Announcement
 Breakfast　　　　　　　　　　　　1202
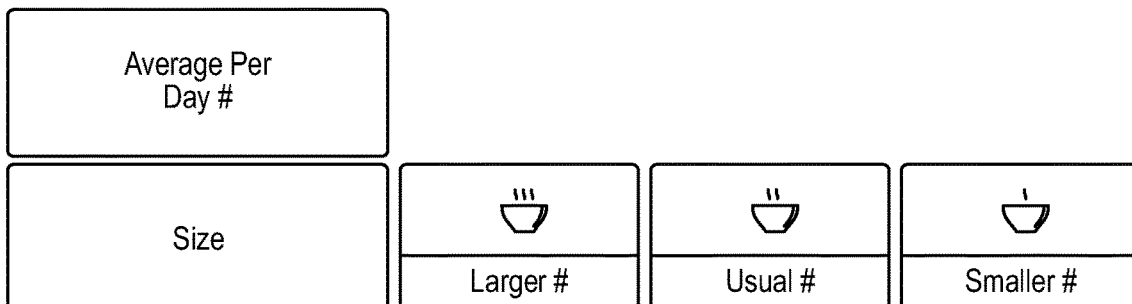
 Lunch
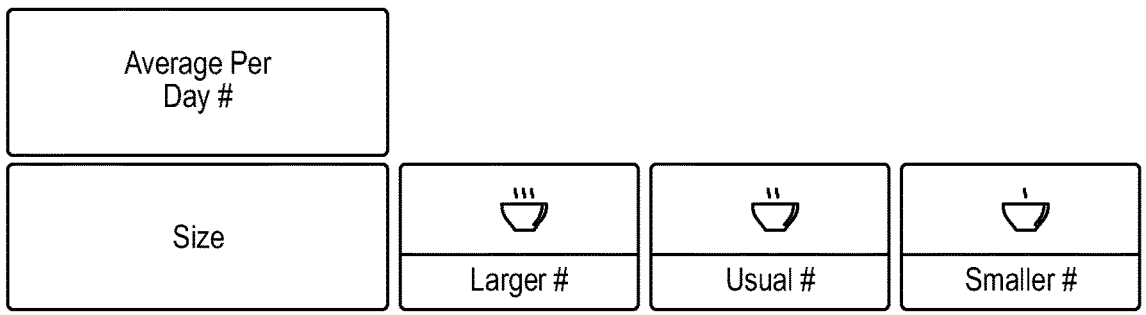
 Dinner
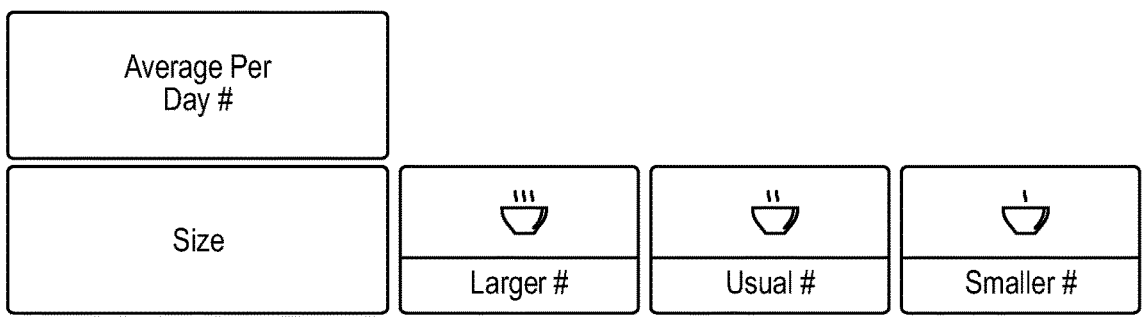
FIG. 12

BLOOD GLUCOSE CONTROL SYSTEM WITH CONTROL PARAMETER MODIFICATION

STATEMENT REGARDING FEDERALLY SPONSORED RESEARCH OR DEVELOPMENT

This invention was made with U.S. Government support under Agreement No. W912CG20C0013, awarded by Defense Advanced Research Projects Agency. The Government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. In addition, this application hereby incorporates by reference in their entirety for all purposes and makes a part of this specification the following applications filed on the same date as this application:

| U.S. application No. | Title | Filing Date |
| --- | --- | --- |
| 17/062,022 | BLOOD GLUCOSE CONTROL SYSTEM WITH CARBOHYDRATE THERAPY INDICATION | Oct. 2, 2020 |
| 17/061,917 | BLOOD GLUCOSE CONTROL SYSTEM WITH REAL-TIME GLYCEMIC CONTROL OPTIMIZATION | Oct. 2, 2020 |
| 17/061,990 | BLOOD GLUCOSE CONTROL SYSTEM WITH AUTOMATED BACKUP THERAPY PROTOCOL GENERATION | Oct. 2, 2020 |

TECHNICAL FIELD

The present disclosure relates to ambulatory medical devices, such as blood glucose control systems, that provide therapy to a subject.

BACKGROUND

Sustained delivery, pump driven medicament injection devices generally include a delivery cannula mounted in a subcutaneous manner through the skin of the patient at an infusion site. The pump draws medicine from a reservoir and delivers it to the patient via the cannula. The injection device typically includes a channel that transmits a medicament from an inlet port to the delivery cannula which results in delivery to the subcutaneous tissue layer where the delivery cannula terminates. Some infusion devices are configured to deliver one medicament to a patient while others are configured to deliver multiple medicaments to a patient.

SUMMARY

The systems, methods, and devices of this disclosure each have several innovative aspects, no single one of which is solely responsible for all the desirable attributes disclosed herein. Details of one or more implementations of the subject matter described in this specification are set forth in the accompanying drawings and the description below.

Certain embodiments disclosed herein relate to a computer-implemented method of generating an indication of total carbohydrate therapy over a period in a subject using a medicament pump configured to deliver at least insulin therapy to the subject. The method may be performed by a hardware processor configured to generate dose control signals for the medicament pump configured to deliver at least insulin therapy to the subject. The method may include receiving a glucose level of the subject and determining based at least in part on the glucose level that a triggering event for raising blood glucose level of the subject has occurred. The triggering event may comprise determining that an impending risk of hypoglycemia is present in the subject or that an episode of hypoglycemia is present in the subject. The method may further include determining an amount of a counter-regulatory agent to respond to the impending risk of hypoglycemia or the episode of hypoglycemia. Further, the method may include determining a dose of carbohydrate therapy based at least in part on the amount of the counter-regulatory agent. Additionally, the method may include tracking, over a period comprising a plurality of hypoglycemia risk events or hypoglycemia episodes, determined doses of carbohydrate therapy to generate the indication of total carbohydrate therapy over the period. The method may include outputting the indication of total carbohydrate therapy.

Additional embodiments of the present disclosure relate to an automated blood glucose control system configured to generate an indication of total carbohydrate therapy over a period in a subject. The automated blood glucose control system may include a medicament delivery interface configured to operatively connect to a medicament pump configured to infuse medicament into the subject. The medicament may comprise at least insulin. Further, the automated blood glucose control system may include a memory configured to store specific computer-executable instructions, and a hardware processor in communication with the memory and configured to execute the specific computer-executable instructions to at least: receive a glucose level of the subject; determine based at least in part on the glucose level that a triggering event for raising blood glucose level of the subject has occurred, wherein the triggering event comprises that an impending risk of hypoglycemia is present in the subject or that an episode of hypoglycemia is present in the subject; determine an amount of a counter-regulatory agent to respond to the impending risk of hypoglycemia or the episode of hypoglycemia; determine a dose of carbohydrate therapy based at least in part on the amount of the counter-regulatory agent; track, over a period comprising a plurality of hypoglycemia risk events or hypoglycemia episodes, determined doses of carbohydrate therapy to generate the indication of total carbohydrate therapy over the period; and output the indication of total carbohydrate therapy.

Certain embodiments of the present disclosure relate to an automated blood glucose control system configured to generate a backup therapy protocol comprising insulin therapy instructions derived from autonomously determined doses of insulin. The automated blood glucose control system may include a medicament delivery interface configured to operatively connect to a medicament pump for infusing medicament into the subject. Further, the automated blood glucose control system may include a memory configured to store specific computer-executable instructions, and a hardware processor in communication with the memory and configured to execute the specific computer-executable instructions to at least: receive a glucose level signal from a sensor operatively configured to determine glucose levels in the subject; generate a dose control signal using a control algorithm configured to autonomously determine doses of insulin to be infused into the subject for the purpose of controlling blood glucose of the subject based at least in part on the glucose level signal; track insulin therapy administered to the subject over a tracking period comprising at least one day by the automated blood glucose control system, wherein tracking the insulin therapy comprises storing an indication of the autonomously determined doses of insulin delivered to the subject as basal insulin, correction boluses of insulin, or as mealtime boluses of insulin; generate at least one of a backup injection therapy protocol or a backup pump therapy protocol comprising insulin therapy instructions based at least in part on the insulin therapy administered to the subject over the tracking period; and output the at least one of the backup injection therapy protocol or the backup pump therapy protocol on a display enabling therapy to be maintained at a rate determined by the automated blood glucose control system when the automated blood glucose control system is not providing therapy to the subject.

Additional embodiments of the present disclosure relate to a computer-implemented method of generating a backup therapy protocol comprising insulin therapy instructions derived from autonomously determined doses of insulin determined by an automated blood glucose control system. The method may be performed by a hardware processor of the automated blood glucose control system. The method may include receiving a glucose level signal from a sensor operatively configured to determine glucose levels in the subject and generating a dose control signal using a control algorithm configured to autonomously determine doses of insulin to be infused into the subject for the purpose of controlling blood glucose of the subject based at least in part on the glucose level signal. Further, the method may include tracking insulin therapy administered by the automated blood glucose control system to the subject over a tracking period comprising at least one day. Tracking the insulin therapy may comprise storing an indication of the autonomously determined doses of insulin delivered to the subject. Further, the method may include generating at least one of a backup injection therapy protocol or a backup pump therapy protocol comprising insulin therapy instructions based at least in part on the insulin therapy administered to the subject over the tracking period. In addition, the method may include outputting the at least one of the backup injection therapy protocol or the backup pump therapy protocol on a display enabling therapy to be maintained at a rate determined by the automated blood glucose control system when the automated blood glucose control system is not providing therapy to the subject.

Some embodiments of the present disclosure relate to an automated blood glucose control system configured to generate a report of therapy protocol modifications made by a user of the automated blood glucose control system. The automated blood glucose control system may include a medicament delivery interface configured to operatively connect to a medicament pump for infusing medicament into a subject. Further, the automated blood glucose control system may include a memory configured to store specific computer-executable instructions, a stored control parameter value, and a therapy log. Moreover, the automated blood glucose control system may include a hardware processor in communication with the memory and configured to execute the specific computer-executable instructions to at least: receive a glucose level signal from a sensor operatively configured to determine glucose levels in the subject; generate a dose control signal using a control algorithm configured to autonomously determine doses of insulin to be infused into the subject for the purpose of controlling blood glucose of the subject based at least in part on the glucose level signal and a control parameter that is modifiable by user interaction with a control parameter selection interface element; track user modifications to the control parameter over a tracking period comprising at least one day, wherein tracking the user modifications comprises storing in the therapy log whether each of the user modifications comprises an increase or a decrease in the control parameter from the stored control parameter value and a time during which each of the user modifications occurred; and generate a report of user modifications to the control parameter, wherein the report comprises a measure of frequency of increases and decreases from the stored control parameter value.

Certain embodiments of the present disclosure relate to a computer-implemented method of modifying therapy provided to a subject using a blood glucose control system. The method may be performed by a hardware processor configured to generate a dose control signal for the blood glucose control system. Further, the method may include receiving a glucose level signal from a glucose level sensor operatively connected to the subject. Moreover, the method may include causing first therapy to be delivered by the blood glucose control system to a subject during a first therapy period, wherein the first therapy is delivered based at least in part on a first value of a control parameter used by a control algorithm to generate the dose control signal. The control parameter may be used by the control algorithm to account for accumulation of insulin in the subject, thereby controlling an insulin dosing response of the control algorithm to a blood glucose excursion in the subject as indicated by the glucose level signal. Further, the method may include determining a first effect corresponding at least in part to the first therapy. Determining the first effect may comprise analyzing glycemic control of blood glucose in the subject as indicated by the glucose level signal. Moreover, the method may include autonomously generating a second value of the control parameter. The autonomously generated second value may be determined as a function based on the first value and the first effect. In addition, the method may include modifying the control parameter from the first value to the second value and causing second therapy to be delivered by the blood glucose control system to the subject during a second therapy period. The second therapy may be delivered based at least in part on the second value of the control parameter. Further, changing the control parameter may modify the therapy provided to the subject.

Additional embodiments of the present disclosure relate to a computer-implemented method of modifying therapy provided to a subject using a blood glucose control system. The method may be performed by a hardware processor configured to generate a dose control signal for the blood glucose control system. The method may include causing first therapy to be delivered by the blood glucose control system to a subject during a first therapy period. The first therapy may be delivered based at least in part on a first value of a control parameter used by a control algorithm to generate the dose control signal. The method may further include determining a first effect corresponding at least in part to the first therapy. Determining the first effect may comprise receiving a glucose level signal from a glucose level sensor operatively connected to the subject. Further, the method may include autonomously generating a second value of the control parameter based at least in part on a baseline value of the control parameter and an output of a function defined based on glycemic control of the subject. The glucose level signal may comprise an indication of the glycemic control of the subject during the first therapy period. Moreover, the method may include modifying the control parameter from the first value to the second value and causing second therapy to be delivered by the blood glucose control system to the subject during a second therapy period. The second therapy may be delivered based at least in part on the second value of the control parameter. Changing the control parameter may include modifying the therapy provided to the subject.

Some embodiments of the present disclosure relate to a computer-implemented method of modifying therapy provided to a subject using a blood glucose control system. The method may be implemented by a hardware processor configured to generate a dose control signal for the blood glucose control system. The method may include causing first therapy to be delivered by the blood glucose control system to a subject during a first therapy period. The first therapy may be delivered based at least in part on a first value of a control parameter used by a control algorithm to generate the dose control signal. The method may further include determining a first effect corresponding at least in part to the first therapy. Determining the first effect may comprise receiving a glucose level signal from a glucose level sensor operatively connected to the subject. Further, the method may include autonomously generating a second value of the control parameter. The autonomously generated second value may be determined as a function based at least in part on a baseline value. Moreover, the method may include modifying the control parameter from the first value to the second value. The method may further include causing second therapy to be delivered by the blood glucose control system to the subject during a second therapy period. The second therapy may be delivered based at least in part on the second value of the control parameter. Further, changing the control parameter may include modifying the therapy provided to the subject. The method may further include determining a second effect corresponding at least in part to the second therapy and autonomously performing a comparison of the first effect and the second effect without action by a human. Further, the method may include selecting one of the first value of the control parameter or the second value of the control parameter as an active control parameter value based at least in part on the comparison of the first effect and the second effect. Moreover, the method may include configuring the blood glucose control system to provide therapy to the subject during a third therapy period based at least in part on the active control parameter value. The selection of the active control parameter value may modify the therapy provided to the subject.

Moreover, any of the aforementioned embodiments may be combined. For example, a single automated blood glucose control system may be configured to implement one or more of the aforementioned embodiments.

BRIEF DESCRIPTION OF THE DRAWINGS

Throughout the drawings, reference numbers are re-used to indicate correspondence between referenced elements.

The drawings are provided to illustrate certain aspects of the subject matter described herein and not to limit the scope thereof.

FIG. 2A shows a block diagram of an example blood glucose control system.

FIG. 2B shows a block diagram of another example blood glucose control system.

FIG. 2C shows a block diagram of another example blood glucose control system.

FIG. 2D shows a block diagram of another example blood glucose control system.

FIG. 10 illustrates an example backup therapy protocol in accordance with certain embodiments.

FIG. 11 illustrates an example control parameter modification report in accordance with certain embodiments.

FIG. 12 illustrates an example meal selection report that may be included as part of some implementations of the control parameter modification report of FIG. 11 in accordance with certain embodiments.

DETAILED DESCRIPTION

Figure 1A:
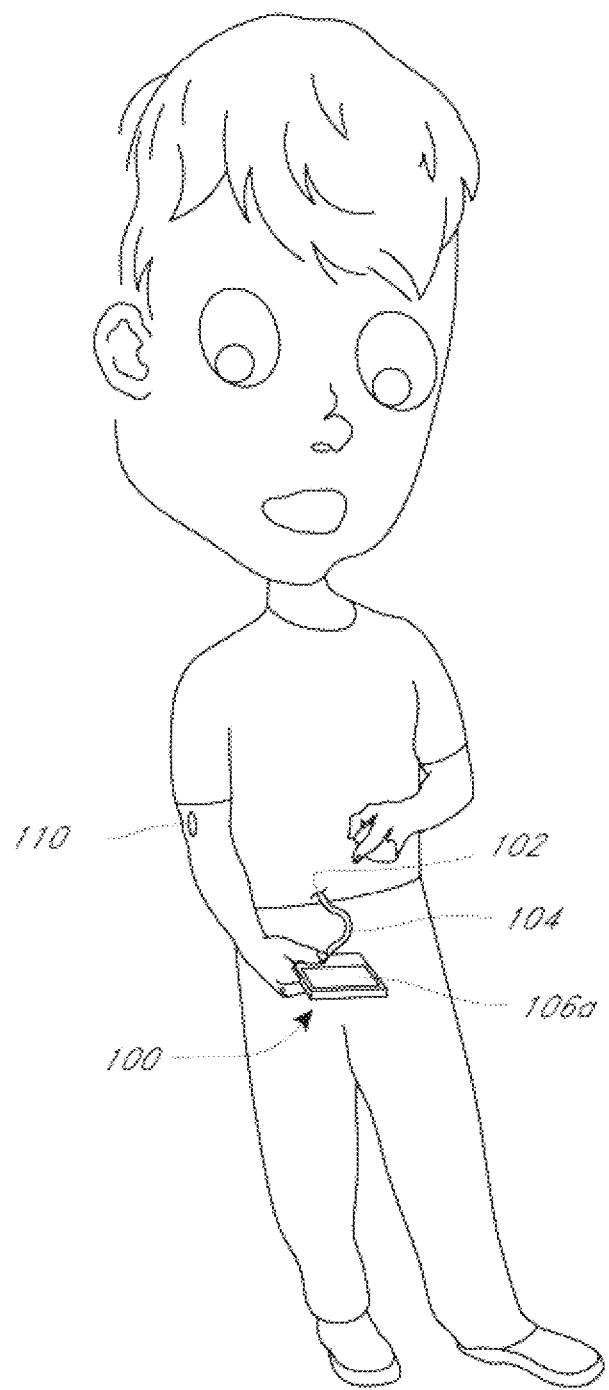
FIG. 1A illustrates an example blood glucose control system that provides blood glucose control via an ambulatory medicament pump.

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a patient. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A blood glucose control system can operate in conjunction with an infusion system to infuse one or more medicaments, including at least one blood glucose control agent, into a subject. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Blood Glucose Control System Overview

Blood glucose control systems are used to control blood glucose level in a subject. Blood glucose control systems can include a controller configured to generate dose control signals for one or more glucose control agents that can be infused into the subject. Glucose control agents include regulatory agents that tend to decrease blood glucose level, such as insulin and insulin analogs, and counter-regulatory agents that tend to increase blood glucose level, such as glucagon or dextrose. A blood glucose control system configured to be used with two or more glucose control agents can generate a dose control signal for each of the agents. In some embodiments, a blood glucose control system can generate a dose control signal for an agent even though the agent may not be available for dosing via a medicament pump connected to the subject.

Glucose control agents can be delivered to a subject via subcutaneous injection, via intravenous injection, or via another suitable delivery method. In the case of blood glucose control therapy via an ambulatory medicament pump, subcutaneous injection is most common. An ambulatory medicament pump 100 is a type of ambulatory medical device, which is sometimes referred to herein as an ambulatory device, an ambulatory medicament device, a mobile ambulatory device, or an AMD. Ambulatory medical devices include ambulatory medicament pumps and other devices configured to be carried by a subject and to deliver therapy to the subject.

In some examples, the ambulatory medical device (AMD) is an electrical stimulation device, and therapy delivery includes providing electrical stimulation to a subject. An example of an electrical stimulation device is a cardiac pacemaker. A cardiac pacemaker generates electrical stimulation of the cardiac muscle to control heart rhythms. Another example of an electrical stimulation device is a deep brain stimulator to treat Parkinson's disease or movement disorders.

Figure 1B:
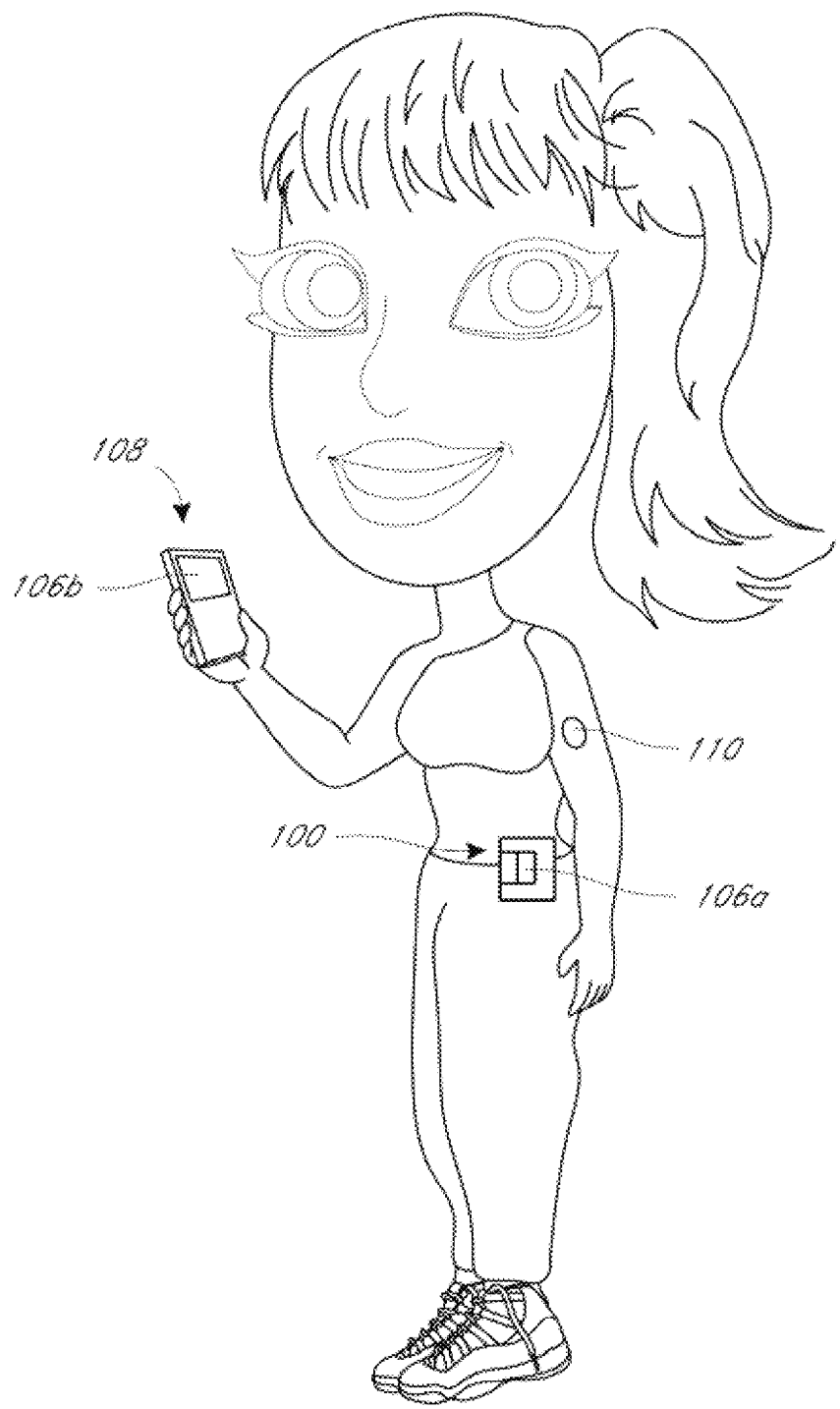
FIG. 1B illustrates another example blood glucose control system that provides blood glucose control via an ambulatory medicament pump.
Figure 1C:
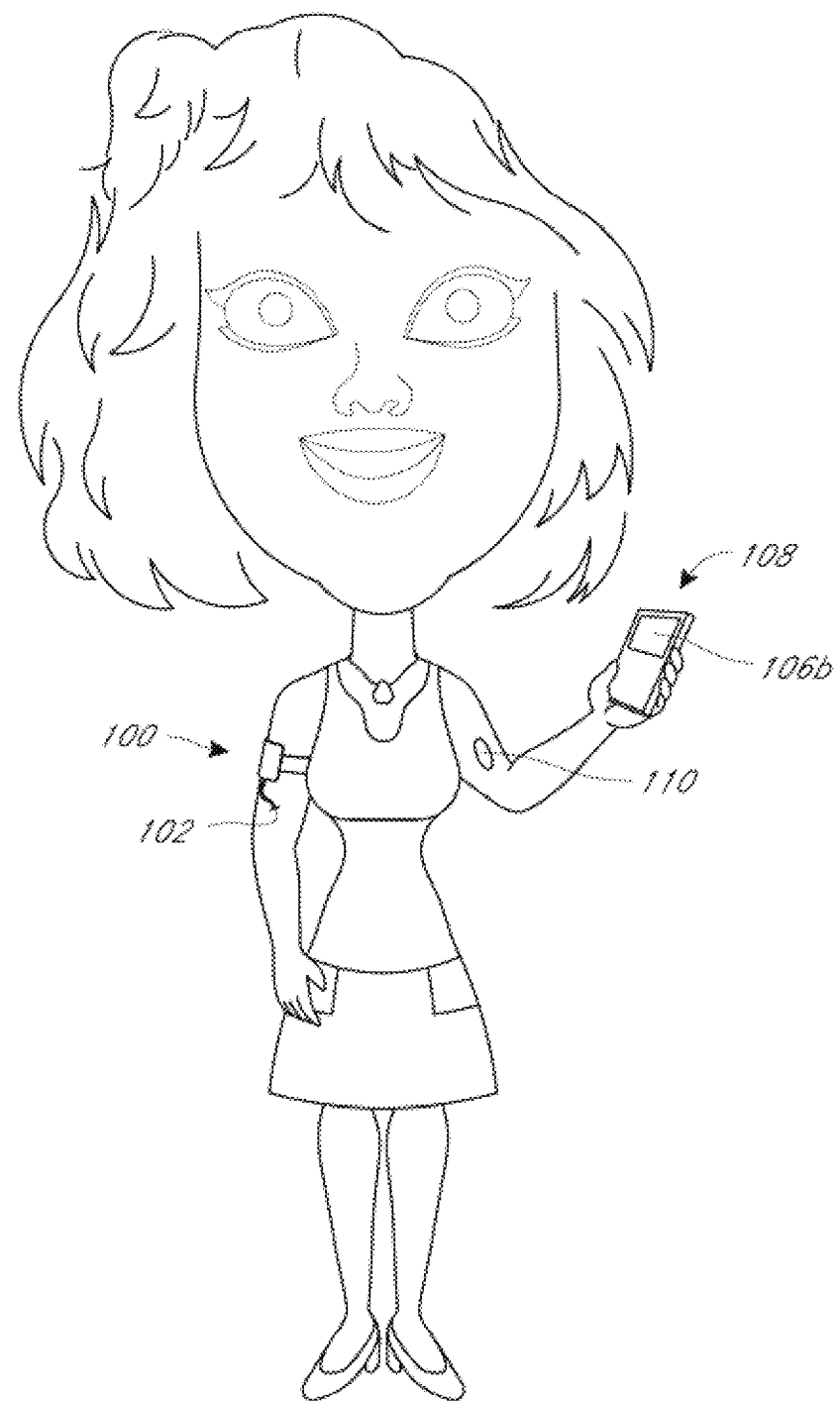
FIG. 1C illustrates a further example blood glucose control system that provides blood glucose control via an ambulatory medicament pump.

FIGS. 1A-1C show examples of blood glucose control systems that provide blood glucose control via an ambulatory medicament pump connected to a subject. In FIG. 1A, the medicament pump 100 is connected to an infusion site 102 using an infusion set 104. The medicament pump has integrated pump controls 106a that permit a user to view pump data and change therapy settings via user interaction with the pump controls 106a. A glucose level sensor 110 generates a glucose level signal that is received by the blood glucose control system.

In FIG. 1B, the medicament pump 100 communicates with an external electronic device 108 (such as, for example, a smartphone) via a wireless data connection. At least some of the pump controls 106a and 106b can be manipulated via user interaction with user interface elements of the external electronic device 108. The glucose level sensor 110 can also communicate with the medicament pump 100 via a wireless data connection.

In FIG. 1C, the medicament pump 100 includes an integrated cannula that inserts into the infusion site 102 without a separate infusion set. At least some of the pump controls 106b can be manipulated via user interaction with user interface elements of an external electronic device 108. In some instances, pump controls can be manipulated via user interaction with user interface elements generated by a remote computing environment (not shown), such as, for example, a cloud computing service, that connects to the medicament pump 100 via a direct or indirect electronic data connection.

Glucose control systems typically include a user interface configured to provide one or more of therapy information, glucose level information, and/or therapy control elements capable of changing therapy settings via user interaction with interface controls. The user interface can be implemented via an electronic device that includes a display and one or more buttons, switches, dials, capacitive touch interfaces, or touchscreen interfaces. In some embodiments, at least a portion of the user interface is integrated with an ambulatory medicament pump that can be tethered to a body of a subject via an infusion set configured to facilitate subcutaneous injection of one or more glucose control agents. In certain embodiments, at least a portion of the user interface is implemented via an electronic device separate from the ambulatory medicament pump, such as a smartphone.

FIGS. 2A-2D illustrate block diagrams showing example configurations of a glucose control system 200. As shown in FIG. 2A, a glucose control system 200a can include a controller 202a having an electronic processor 204a and a memory 210a that stores instructions 208a executable by the processor 204a. The controller 202a and a pump 212 can be integrated with into an ambulatory medical device (AMD) 100. The AMD 100 can include a transceiver 214a for wireless digital data communications with external electronic devices. When the instructions 208a stored in memory 210a are executed by the electronic processor 204a, the controller 202a can implement at least a portion of a control algorithm that generates dose control signals for one or more glucose control agents based on time-varying glucose levels of the subject and one or more control parameters. The dose control signals, when delivered to the pump 212, result in dosing operations that control the blood glucose of a subject.

As shown in FIG. 2B, a glucose control system 200b can operate at least partially via execution of instructions 208b by an electronic processor 204b of an electronic device 108 separate from the ambulatory medical device 100. The electronic device 108 can include a transceiver 214b capable of establishing a wireless digital data connection to the AMD 100, and a controller 202b can implement at least a portion of a control algorithm via execution of instructions 208b stored in memory 210b. When the instructions 208b stored in memory 210b are executed by the electronic processor 204b, the controller 202b can implement at least a portion of a control algorithm that generates dose control signals for one or more glucose control agents based on time-varying glucose levels of the subject and one or more control parameters. The dose control signals, when delivered to the pump 212, result in dosing operations that control the blood glucose of a subject. In some embodiments, the dose control signals are transmitted from the device transceiver 214b to the AMD transceiver 214a over a short-range wireless data connection 216. The AMD 100 receives the dose control signals and passes them to the pump 212 for dosing operations.

As shown in FIG. 2C, a glucose control system 200c can operate at least partially via execution of instructions 208c on an electronic processor 204c integrated with a remote computer 206, such as, for example, a cloud service. When the instructions 208c stored in memory 210c are executed by the electronic processor 204c, the controller 202c can implement at least a portion of a control algorithm that generates dose control signals for one or more glucose control agents based on time-varying glucose levels of the subject and one or more control parameters. The dose control signals, when delivered to the pump 212, result in dosing operations that control the blood glucose of a subject. In some embodiments, the dose control signals are transmitted from the remote computer WAN connection interface 220c to the AMD WAN connection interface 220a over an end-to-end wireless data connection 218. The AMD 100 receives the dose control signals and passes them to the pump 212 for dosing operations.

As shown in FIG. 2D, a glucose control system 200d can have two or more controllers 202a, 202b, 202c that cooperate to generate a dose control signal for dosing operations by the pump 212. A remote computer 206 can transmit or receive data or instructions passed through a WAN connection interface 220c via a WAN wireless data connection 218 to a WAN connection interface 220b of an electronic device 108. The electronic device 108 can transmit or receive data or instructions passed through a transceiver 214b via a short-range wireless data connection 216 to a transceiver 214a of an AMD 100. In some embodiments, the electronic device can be omitted, and the controllers 202a, 202c of the AMD 100 and the remote computer 206 cooperate to generate dose control signals that are passed to the pump 212. In such embodiments, the AMD 100 may have its own WAN connection interface 220a to support a direct end-to-end wireless data connection to the remote computer 206.

Figure 3:
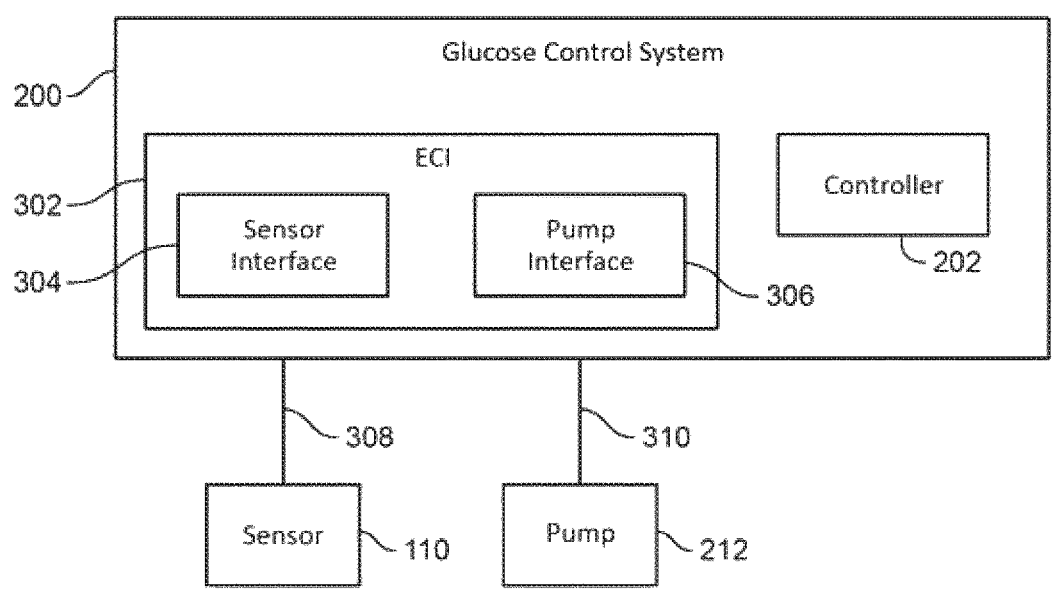
FIG. 3 is a schematic of an example glucose control system that includes an electronic communications interface.

As shown in FIG. 3, in some embodiments, the glucose control system 200 includes circuitry that implements an electronic communications interface (ECI) 302 configured to send and receive electronic data from one or more electronic devices. The ECI includes a sensor interface 304 configured to receive a glucose level signal from a sensor 110 such as a continuous glucose monitor (CGM). Some CGMs generate the glucose level signal at fixed measurement intervals, such as five-minute intervals. The sensor 110 can be operatively connected to a subject in order to generate a glucose level signal that corresponds to a blood glucose estimate or measurement of the subject. The glucose level signal can be used by the controller 202 to generate a dose control signal. The dose control signal can be provided to a pump 212 via a pump interface 306. In some embodiments, the sensor interface 304 connects to the sensor 110 via a short-range wireless connection 308. In some embodiments, the pump interface 306 connects to the pump 212 via a short-range wireless connection 310. In other embodiments, the pump interface 306 connects to the pump 212 via a local data bus, such as when the controller 202, the ECI 306, and the pump 212 are integrated into an AMD 100.

The controller can be configured to generate the dose control signal using a control algorithm that generates at least one of a basal dose, a correction dose, and/or a meal dose. Examples of control algorithms that can be used to generate these doses are disclosed in U.S. Patent Application Publication Nos. 2008/0208113, 2013/0245547, 2016/0331898, and 2018/0220942 (referenced herein as the "Controller Disclosures"), the entire contents of which are incorporated by reference herein and made a part of this specification. The correction dose can include regulatory or counter-regulatory agent and can be generated using a model-predictive control (MPC) algorithm such as the one disclosed in the Controller Disclosures. The basal dose can include regulatory agent and can be generated using a basal control algorithm such as disclosed in the Controller Disclosures. The meal dose can include regulatory agent and can be generated using a meal control algorithm such as disclosed in the Controller Disclosures. Additional aspects and improvements for at least some of these controllers are disclosed herein. The dose control signal can be transmitted to an infusion motor 306 via the ECI 302 or can be transmitted to the infusion motor 306 via an electrical conductor when the controller 202a is integrated in the same housing as the infusion motor 306.

Figure 4A:
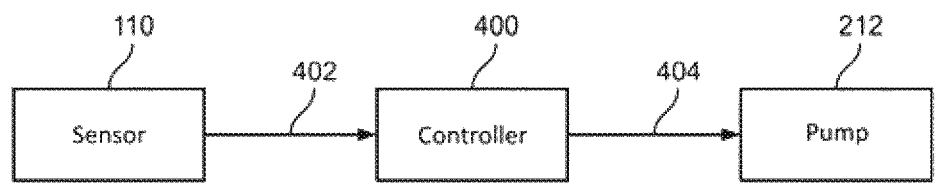
FIG. 4A shows a block diagram of an example blood glucose control system in online operation mode.

As shown in FIG. 4A, the controller 400 can be configured to operate in "online mode" during time periods when the controller receives a glucose level signal 402 from a sensor 110. In online mode, the control algorithm generates a dose control signal 404 that implements regular correction doses based on values of the glucose level signal 402 and control parameters of the control algorithm. The pump 212 is configured to deliver at least correction doses and basal doses to the subject without substantial user intervention while the controller 400 remains in online mode.

Figure 4B:
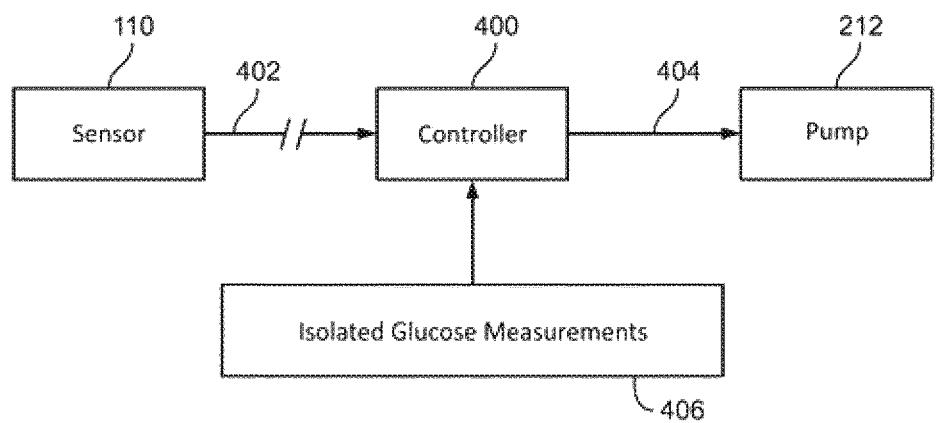
FIG. 4B shows a block diagram of an example blood glucose control system in offline operation mode.

As shown in FIG. 4B, the controller 400 can be configured to operate in "offline mode" during time periods when the controller does not receive a glucose level signal 402 from a sensor 110, at least during periods when the glucose level signal 402 is expected but not received. In offline mode, the control algorithm generates a dose control signal 404 that implements correction doses in response to isolated glucose measurements 406 (such as, for example, measurements obtained from the subject using glucose test strips) and based on control parameters of the control algorithm. The pump 212 is configured to deliver basal doses to the subject without substantial user intervention and can deliver correction doses to the subject in response to isolated glucose measurements 406 while the controller 400 remains in offline mode.

Example Implementation of Glucose Control System

Figure 5:
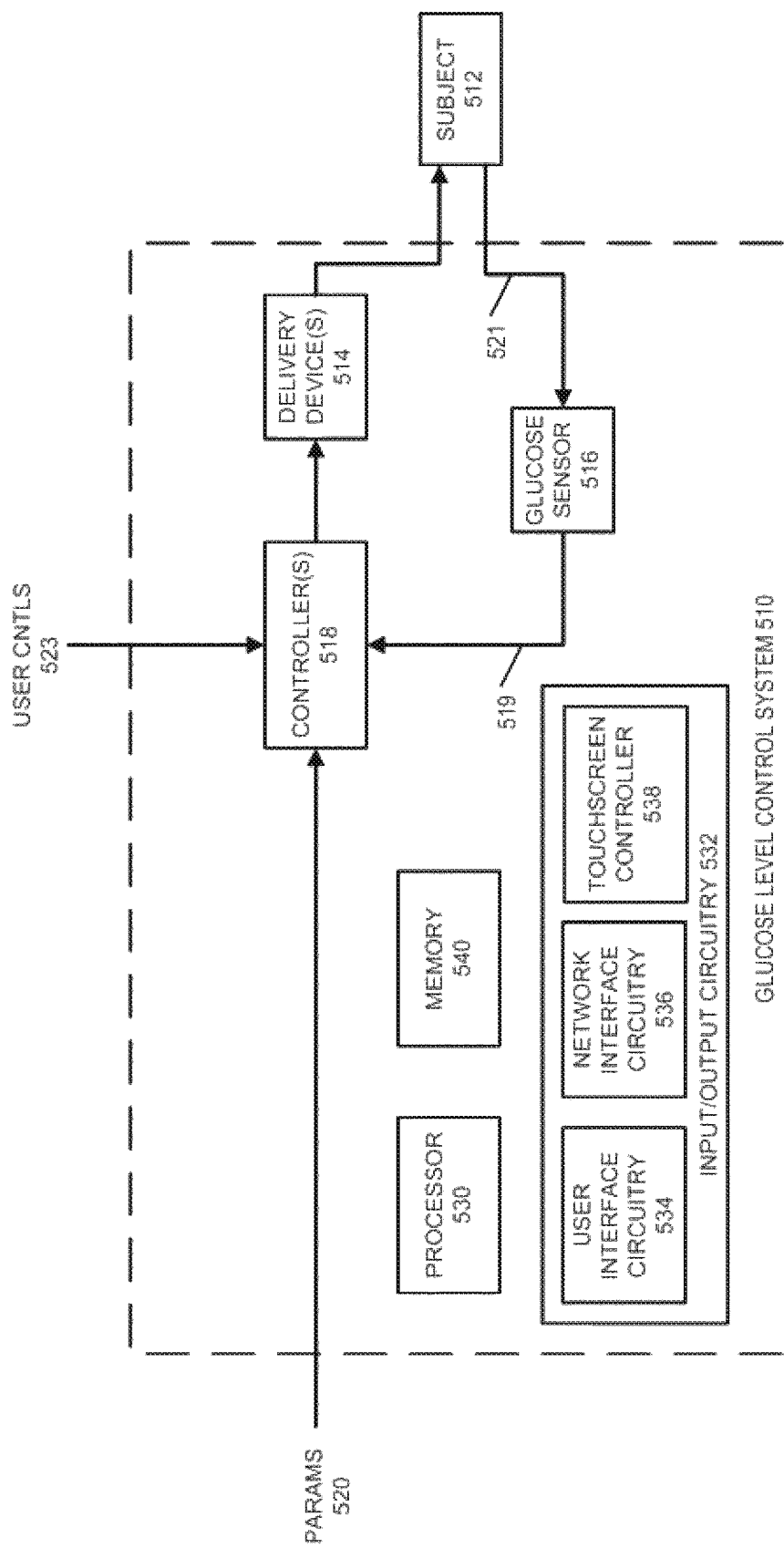
FIG. 5 illustrates a block diagram of a glucose control system in accordance with certain embodiments.

FIG. 5 illustrates an automated glucose control system 510 for regulating the blood glucose level of an animal subject (subject) 512, which may be a human. The automated glucose control system 510 is an example of a medicament infusion system and may include any of the embodiments previously described above with respect to medicament infusion systems.

The subject 512 may receive doses of insulin from one or more delivery devices 514, for example infusion pump(s) coupled by catheter(s) to a subcutaneous space of the subject 512. As described below, the delivery devices 514 may also deliver a counter-regulatory agent or hyperglycemic agent, such as glucagon or dextrose, for control of the blood glucose level under certain circumstances. For the delivery of both insulin and a counter-regulatory agent (e.g., glucagon), the delivery devices 514 may be mechanically driven infusion mechanisms having dual cartridges for insulin and the counter-regulatory agent, respectively. In the present description, reference is made to glucagon specifically, but it is to be understood that this is for convenience only and that other counter-regulatory agents (e.g., dextrose) may be used. Similarly, the term "insulin" herein is to be understood as encompassing all forms of insulin-like substances including natural human or animal insulin as well as synthetic insulin in any of a variety of forms (commonly referred to as "insulin analogs").

For online or autonomous operation, a glucose sensor 516 is operatively coupled to the subject 512 to continually sample a glucose level of the subject 512. In some cases, the glucose sensor 516 may be referred to as a continuous glucose monitoring (CGM) sensor, which may continuously or periodically measure or sense blood glucose levels of the subject 512 for at least a period of time. Sensing may be accomplished in a variety of ways, generally involving some form of physical coupling 521 between the subject 512 and the glucose sensor 516. A controller 518 may control operation of the delivery device(s) 514 as a function of a glucose level signal 519 from the glucose sensor 516 and subject to programmed input parameters (PARAMS) 520 which may be provided by a user such as the subject 512, a parent or guardian of the subject 512, or a healthcare provider (e.g., a clinician or doctor). One input parameter for automatic operation may include the weight of the subject 512. In some cases, the glucose control system 510 can provide effective automated control without receiving explicit information regarding either meals that the subject 512 has ingested or any other "feedforward" information, which is achieved in part by an adaptive aspect to operation of the controller 518. In other cases, the glucose control system 510 can use received information regarding either meals that the subject ingested, or plans to ingest, or other "feedforward" information to modify control of blood glucose and/or delivery of insulin or counter-regulatory agent.

The controller 518 is an electrical device with control circuitry that provides operating functionality as described herein. In one embodiment, the controller 518 may be realized as a computerized device (e.g., a hardware processor) having computer instruction processing circuitry that executes one or more computer programs each including respective sets of computer instructions. In some cases, the processing circuitry will generally include one or more processors 530 along with memory 540 and input/output circuitry 532 coupled to or in communication with the processor(s) 530, where the memory 540 stores computer program instructions and data, and the input/output circuitry 532 can provide interface(s) to external devices such as the glucose sensor 516 and delivery device(s) 514. In some cases, the input/output circuitry 532 may provide a user interface, or may operate with one or more processors (e.g., the controller 518 or a separate processor 530 included in the glucose control system 510 or in a separate computing system, such as a smartphone, a laptop computer, a desktop computer, a smartwatch, and the like) to provide a user interface to a user (e.g., the subject 512, a parent or guardian, or a clinician). In some cases, the input/output circuitry 532 may include a touchscreen and/or a touchscreen controller 538 configured to control a touchscreen (not shown).

In some cases, the controller 518 may perform all of the functionality of the glucose level control system 510. In such cases, the processor 530 may be optional or omitted. In other cases, the controller 518 may perform at least automated blood glucose control of the subject 512, and one or more separate processors 530 may perform one or more additional operations of the blood glucose control system 510 (or medicament pump), such as tracking occurrences of hyperglycemic or hypoglycemic events or risk events, outputting data to a user, controlling or initiating communication with another computing system, regulating access to the glucose level control system 510, or other operations unrelated to operation of a medicament pump or the delivery devices 514.

The input/output circuitry 532 may control communication with one or more other computing systems and/or with a user. In some cases, the input/output circuitry 532 may include one or more separate interface circuits or controllers to facilitate user interaction and/or communication. For example, the input/output circuitry 532 may include user interface circuitry 534, network interface circuitry 536, and/or a touchscreen controller 538.

The user interface circuitry 534 may include any circuitry or processors that may output a user interface to a user and/or receive user input from the user via the user interface. The user interface circuitry 534 may receive one or more signals from a processor 530 corresponding to a user interface. The user interface circuitry 534 may control a display to present the user interface to a user based on the one or more signals received from the processor 530. Further, the user interface circuitry 534 may include any circuitry that can receive a signal corresponding to an interaction by a user with a user interface and can provide the signal to the processor 530 and/or controller 518 for further processing. In some cases, the user interface circuitry may be replaced by a touchscreen controller 538 that can control a touchscreen interface. In other cases, the touchscreen controller 538 may be in addition to the user interface circuitry 534.

The network interface circuitry 536 may include any circuitry that enables communication with a wired or wireless network. The network interface circuitry 536 may include one or more network interface cards and/or wireless radios (e.g., a Bluetooth radio, a Bluetooth Low Energy (BLE) radio, a 4 g LTE radio, a 5G radio, a ND-LTE radio, and the like).

The memory 540 can include non-volatile memory and/or volatile memory. The non-volatile memory may include flash memory or solid-state memory.

The control system 510 is also able to operate in an offline manner in which it is used to provide delivery of insulin (and potentially glucagon as well), independent of or without receipt of glucose levels reported by the sensor 516. For example, in cases where the sensor 516 needs replacing, is not properly connected to the subject 512, or is defective, the glucose control system 510 may operate in an offline manner without input from the sensor 516. Thus, overall operation may be divided between online periods each including a succession of sampling intervals when a glucose signal (level) 519 is available, and offline periods each including a succession of sampling intervals when the glucose signal (level) 519 is either completely or intermittently unavailable. The description below uses the terms "online" and "offline" for these periods. Also, offline operation may be user-selected for some reason even when a glucose level signal 519 is available for use.

User control inputs (USER CNTLs 523) may be provided via a local or remote user interface of some type. In some embodiments, the user interface may resemble that of conventional insulin pumps or similar devices, e.g., by including control buttons for commanding the delivery of a bolus and perhaps a small display. In other embodiments, the system may have a wired or wireless interface to a remote device that may incorporate a fuller-function user interface, such as a smartphone, smartwatch, laptop computer, desktop computer, cloud computing service, or other wearable device or computing device. In some cases, the wireless interface may provide access to a local area network, such as a personal home network, a company network, or otherwise. Alternatively, or in addition, the wireless interface may provide a direct connection between local devices available to a user (e.g., via Bluetooth or other near field communication technologies). In some cases, the wireless interface may provide access to a wide area network, such as, but not limited to, the Internet. For example, the wireless interface may include a cellular interface that permits access to a network via a 4G or 5G cellular connection. In some cases, the cellular interface may be a low power interface, such as narrowband LTE or other Internet of Things (IoT) interfaces.

In offline mode, the glucose sensor 516 may be absent, non-functioning, or not coupled to the subject 512. As such, in offline mode, the blood glucose signal 519 may not be available to control automatic operation. In some cases, a user may provide one or more blood glucose measurements to the control system 510 to facilitate automatic operation of the control system 510. These measurements may be provided over a particular time period. Alternatively, or in addition, the glucose control system 510 may use a therapy history and/or a history of prior blood glucose control measurements to facilitate automatic operation of the control system 510 for at least a particular time period.

The description herein refers to a "user" as the source of the user control inputs 523. The "user" as used herein may be the subject 512, a parent or guardian of the subject 512, a healthcare provider (e.g., a clinician, doctor, or other person who may provide medical care to the subject), or any other user who may be authorized to help manage therapy of the subject 512. In certain implementations, the glucose level control system 510 is a personal device worn by a subject 512 for continual glucose control. In some such implementations, the user and subject 512 may be the same person. In other implementations, there may be another person involved in the care of the subject 512 and providing control input, and in such implementations, that other person has the role of user.

Example Controllers for a Blood Glucose Control System

Figure 6:
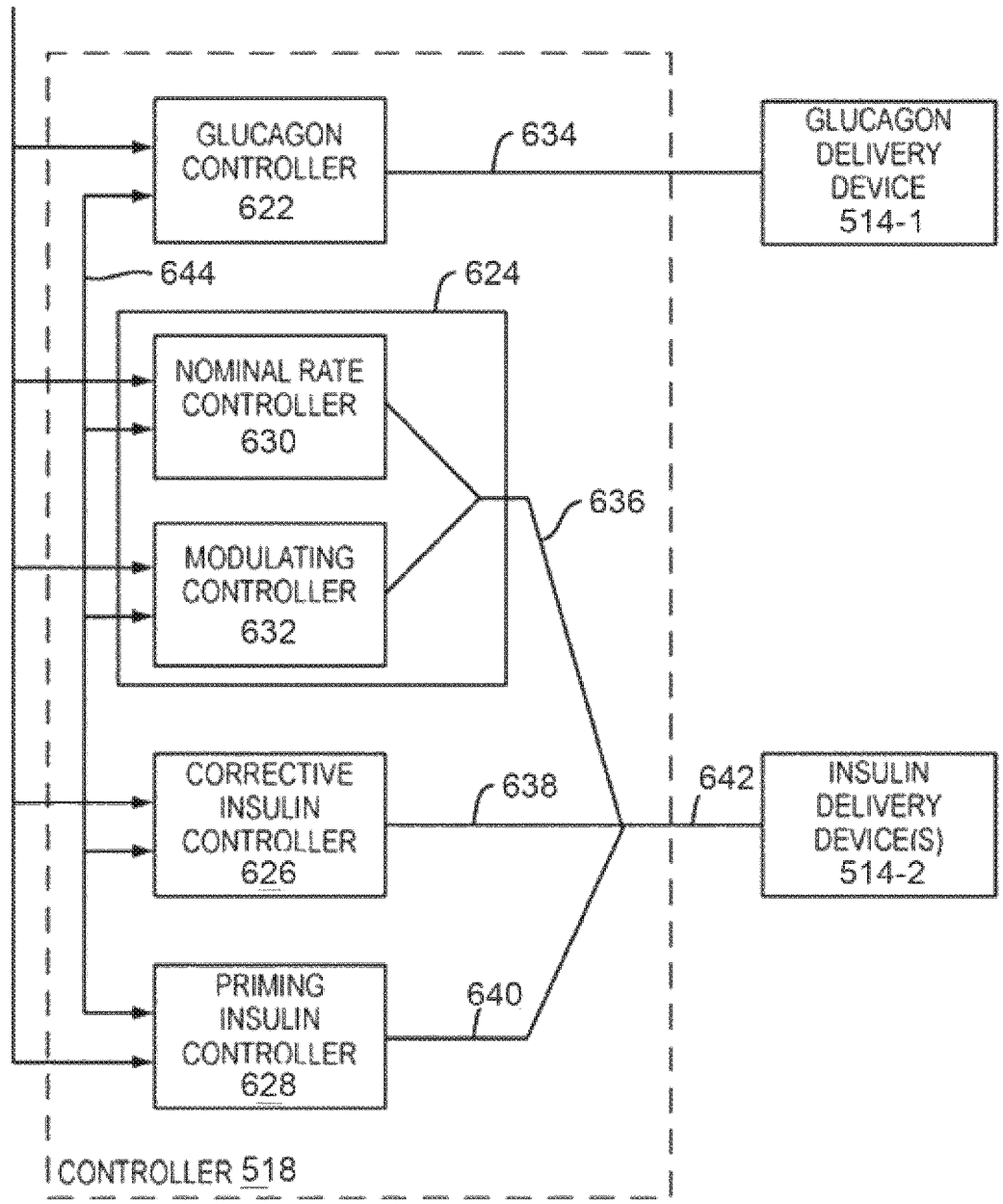
FIG. 6 illustrates a block diagram of a controller system in accordance with certain embodiments.

FIG. 6 shows an example structure of the controller 518 in accordance with certain embodiments. The controller 518 illustrated in FIG. 6 may represent a physical structure with different controllers or processors, or a logical structure that is implemented by one or more physical processors. In other words, a single processor may be used to implement each of the controllers illustrated in FIG. 6, each controller may be implemented by its own processor, or certain processors may implement multiple, but not necessarily all, of the controllers illustrated in FIG. 6 as part of the controller 518. Moreover, although the controllers of FIG. 6 are illustrated as part of the controller 518, in some implementations, one or more of the controllers may be separate from the controller 518.

The controller 518 may include four separate controllers, namely a glucagon (or counter-regulatory agent) controller 622, a basal insulin controller 624, a corrective insulin controller 626, and a priming insulin controller 628. The basal insulin controller 624 includes a nominal rate controller 630 and a modulating controller 632. As shown, the glucagon controller 622 generates a glucagon dose control signal 634 provided to a glucagon delivery device 514-1. Respective outputs 636-640 from the controllers 624-628 may be combined to form an overall insulin dose control signal 642 provided to insulin delivery device(s) 514-2. As shown, the output signal 636 from the basal insulin controller 624 may be formed by a combination of respective outputs of the nominal rate controller 630 and a modulating controller 632. The insulin delivery device(s) 514-2 may include devices tailored to deliver different types and/or quantities of insulin, and the exact configuration may be known to and/or under the control of the controllers 624-628. For ease of description, the collection of one or more insulin delivery devices 514-2 is referred below to in the singular as an insulin delivery device 514-2.

Also shown in FIG. 6 are input/output signals of the various controllers, including the glucose level signal 519, parameters 520 and user inputs 523 as well as a set of inter-controller signals 644. The inter-controller signals 644 enable communication of information from one controller, where the information is developed or generated, to another controller where the information may be used for that controller's control function.

The controllers 622-628 may be operated in either the online/automatic mode or in the offline mode. In the automated mode, the corrective controller 626 regulates glucose level using a control scheme such as described in U.S. Pat. No. 7,806,854, the contents of which are hereby incorporated by reference in its entirety herein. The basal controller 624 and priming insulin controller 628 may perform adaptive automated control as described in International Patent Application Publication WO 2012/058694 A2, the contents of which are hereby incorporated by reference in its entirety herein. The controllers 622-628 generally employ control methods or algorithms that include control parameters that are mathematically combined with reported glucose values to generate an output value that is converted (either directly or via additional conditioning) into the dose control signals 634, 642. For example, the control scheme described in U.S. Pat. No. 7,806,854 includes a generalized predictive control (GPC) method that incorporates a variety of control parameters. The control algorithms are generally adaptive, meaning that control parameters are dynamically adjusted during operation to reflect changing operating circumstances and a "learning" aspect—by monitoring its own operation, the algorithm adjusts its operation to be more specifically tailored to the individual user, enhancing the algorithm's effectiveness and reducing or avoiding a need for additional explicit input information about the user. It should be noted that the input parameters 520 may form part of the control parameters used by the control algorithm. Other control parameters are internal parameters according to the specifics of the algorithm, and selected ones of those internal control parameters are dynamically adjusted to realize the adaptation of the control algorithm.

One feature of operation is the ability of the controllers to learn from recent past periods of online operation and to use that learning during offline operation. U.S. Pat. No. 10,543,313, the contents of which are hereby incorporated by reference in its entirety herein, describes two methods that are usable independently or together in offline operation. A first method automatically calculates the correct size of a correction bolus of insulin at a time of receiving an isolated glucose measurement, the correction bolus then being administered by the system in response to a user control input. A second method automatically calculates the correct size of a meal bolus of insulin and administers it in response to a user control input. Both methods utilize information obtained during past periods of online operation to automatically calculate correct values, freeing the user of a need to make the calculation or provide a correction factor.

Carbohydrate Therapy Equivalence Tracking

Hyperglycemia is a condition that occurs when the levels of sugar or glucose in the blood exceeds a particular level (e.g., 180 mg/dL). This condition may occur in diabetics. To help reduce the occurrence of hyperglycemia, a subject may use an automated blood glucose control system, which may automatically provide insulin to a subject using a medicament pump. The administered insulin may help control the blood glucose level of the subject by consuming glucose in the subject.

Hypoglycemia is a condition that occurs when the levels of sugar or glucose in the blood are below a particular level (e.g., 70 mg/dL). This condition may have adverse consequences including loss of consciousness, seizures, and death. The levels of blood sugar that lead to hyperglycemia and hypoglycemia may vary from patient to patient. To reduce the risk of hypoglycemia, a subject may consume carbohydrates to increase blood sugar. Because of the severe consequences associated with a hypoglycemic event, subjects usually consume carbohydrates that metabolize quickly. These carbohydrates are often unhealthy but are preferable to the occurrence of a hypoglycemic event. For example, the carbohydrates may include candy bars with a lot of refined sugar.

A bihormonal glucose-control system may reduce the risk of occurrence of hypoglycemia by including, in addition to insulin, a counter-regulatory agent (e.g., Glucagon) that can be administered to a subject when the blood glucose level drops too low (e.g., below 50 mg/dL). For subjects who do not have a bihormonal glucose-control system, it may be useful to understand the reduction in carbohydrate therapy, or the consumption of carbohydrates to address hypoglycemic events or potential hypoglycemic events, that can be achieved by switching to a bihormonal glucose-control system. Further, it may be useful for subjects who do have a bihormonal glucose-control system to understand the reduction in carbohydrate therapy obtained by having the bihormonal glucose-control system. For example, understanding the amount of carbohydrate therapy consumed or avoided can be important in monitoring the subject's nutrition intake. While monitoring nutrition in take is important for all people, it is particularly important for diabetics because diabetics must balance eating healthy with ensuring that their blood sugar is maintained in a particular range to avoid both hyperglycemia and hypoglycemia.

The present disclosure relates to a system that can perform a computer-implemented method of generating an indication of total carbohydrate therapy over a time period in a subject using a medicament pump configured to deliver at least insulin therapy to the subject. The system may be an automated blood glucose control system (e.g., the glucose level control system 510) that includes a hardware processor (e.g., controllers 518) for determining dose control signals to provide the medicament pump (e.g., delivery devices 514). In some cases, the medicament pump may be configured to deliver both insulin therapy and counter-regulatory agent (e.g., Glucagon) therapy. Alternatively, the system may be separate from the blood glucose control system but may receive blood glucose information from the blood glucose control system. For example, the system may be personal computing system or a cloud computing system that can received blood glucose information from the blood glucose control system.

The system may receive or determine a glucose level of a subject (e.g., subject 512). The glucose level of the subject may be determined based on a signal (e.g., a glucose level signal) received from a continuous glucose monitoring (CGM) sensor (e.g., glucose sensor 516) that corresponds to the glucose level of the subject. In some cases, the glucose level may be determined from an isolated glucose measurement, such as may be obtained using a glucose measurement kit and/or glucose paper.

Using at least the glucose level of the subject, the system can determine whether a triggering event for raising the subject's blood glucose level has occurred. The triggering event may include a blood glucose level that indicates an occurrence of a hypoglycemic event or a risk of the occurrence of a hypoglycemic event exceeding a risk threshold within a particular period of time. A risk of a hypoglycemic event may be determined when a glucose level of the subject falls below a glucose threshold. This glucose threshold may vary for different subjects and may, in some cases, be specified by the subject or a caregiver (e.g., healthcare provider, parent, or guardian). Thus, in some cases, different triggering events may be defined based on a risk tolerance of a subject to an occurrence of hypoglycemia or to possible different preferences for an amount of blood glucose to be present in the subject. Different subjects may prefer that blood glucose be maintained, or attempt to be maintained, at different levels due, for example, to differences in activity levels or metabolism by different subjects. Determining the risk of the occurrence of a hypoglycemic event may include receiving an indication of a risk of hypoglycemia from a glucose sensor or a prediction of a glucose level at a future time. For example, a determination of an imminent risk of hypoglycemia may comprise a determination that the subject's blood glucose level is expected to be below 60 mg/dl within the next 5-15 minutes.

Responsive to the triggering event, the system may determine an amount of counter-regulatory agent to administer, or an amount of counter-regulatory agent that would be administered if the blood glucose control system included the capability of administering a counter-regulatory agent. In some cases, the counter-regulatory agent is administered by, for example, the automated blood glucose control system. In other cases, the counter-regulatory agent is not administered. For example, the automated blood glucose control system may not be capable of delivering the counter-regulatory agent. As another example, the automated blood glucose control system may be capable of delivering the counter-regulatory agent but may not have a dose of the counter-regulatory agent available.

The system can use the indication of the counter-regulatory agent that is administered or that would be administered to determine a corresponding amount of carbohydrates. The corresponding amount of carbohydrates may be indicative of the amount of carbohydrates that were consumed to prevent the hypoglycemic event, to reduce the risk of the hypoglycemic event, or in response to an occurrence of a hypoglycemic event. Alternatively, or in addition, the corresponding amount of carbohydrates may be indicative of the amount of carbohydrates that would have been consumed if the counter-regulatory agent were not available.

The corresponding amount of carbohydrates may be obtained from a mapping between amounts of a counter-regulatory agent and amounts of carbohydrates. In some cases, the mapping may be based on a measured equivalency between carbohydrates and a counter-regulatory agent. Alternatively, or in addition, the mapping may be between a determined amount of counter-regulatory agent and an amount of carbohydrate a subject indicates he or she normally consumes when determining that a hypoglycemic event may occur.

The mapping may be implemented by a lookup table that maps different amounts of counter-regulatory agent to different corresponding amounts of carbohydrates. In some cases, a single quantity of counter-regulatory agent may map to different amounts of carbohydrates depending on the type of carbohydrate consumed (e.g., simple vs complex carbohydrates, or the type of candy bar consumed, etc.). Alternatively, the mapping may be based on a formula that converts an amount of counter-regulatory agent to an amount of carbohydrates based on a correspondence between the amount of counter-regulatory agent and the amount of carbohydrates. The determination of a relationship between the counter-regulatory agent and carbohydrates may be based on clinical tests comparing carbohydrates to the counter-regulatory agent (e.g., Glucagon, dextrose, etc.). Further, the mapping may be based at least in part on a subject's preferred carbohydrate source and/or characteristics of the subject (e.g., weight).

In some cases, the system can track a number of hypoglycemic events or a number of occurrences of a trigger indicating an impending risk of a hypoglycemic event within a particular time period. The time period may be days, weeks, months, years, or any other period of time over which it is desirable to determine a relationship between carbohydrates consumed or avoided based on the lack of availability or availability of a counter-regulatory agent. In some cases, the tracking of carbohydrate therapy may be based on a number of hypoglycemia events or hypoglycemia risk events instead of or in addition to a time period.

For each occurrence of a hypoglycemic event or occurrence of a trigger indicating an impending risk of a hypoglycemic event, the system can determine an estimate of the carbohydrate therapy saved or that would have been saved by having access to the counter-therapy agent. The system can generate a report for the time period that indicates the total carbohydrate saved or that would have been saved with access to counter-regulatory agent. The report may include an aggregate or sum of the carbohydrate therapy required or saved during the time period. This time period may be days, weeks, months, years, or since a particular time (e.g., since the subject starting using the system). Further, the report may indicate the type of carbohydrates typically consumed by the subject when responding to a hypoglycemic event or a risk of an impending hypoglycemic event. This report can be presented to the subject, a healthcare provider, and/or a parent or guardian of the subject. The healthcare provider can use this report to help care for the subject. For example, the healthcare provider can use the report to generate a nutrition plan for the subject that accounts for the carbohydrates consumed to maintain the blood glucose level within a desired or setpoint range.

The report may include a range of carbohydrate therapy avoided or likely consumed to address the risk of hypoglycemia events. Further, the report may include an amount of calories saved or not consumed, an amount of sugar avoided, an amount of food not consumed, a likely weight gain avoided, etc. based on the use of a counter-regulatory agent in place of carbohydrate therapy.

Carbohydrate Therapy Equivalence Tracking Process

Figure 7:
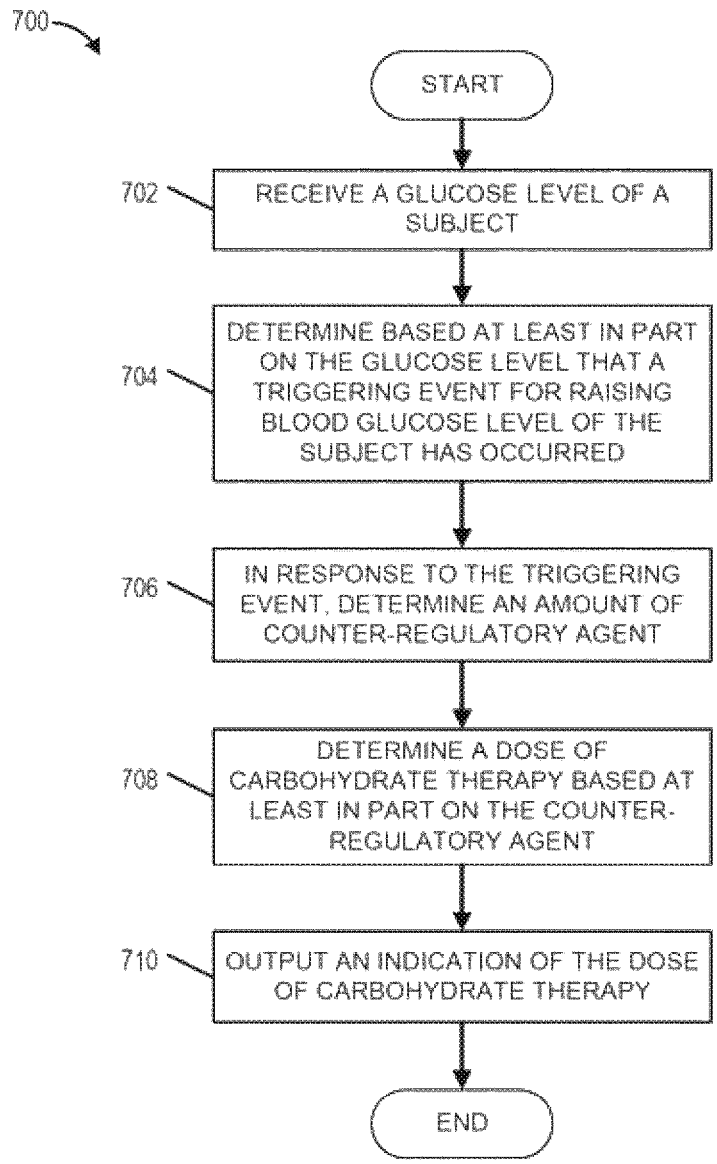
FIG. 7 presents a flowchart of an example carbohydrate therapy equivalence tracking process in accordance with certain embodiments.

FIG. 7 presents a flowchart of an example carbohydrate therapy equivalence tracking process 700 in accordance with certain embodiments. The process 700 may be performed by any system that can track the glucose level of a subject over time and identify hypoglycemic events, or occurrences when a risk of a hypoglycemic event satisfies a threshold (e.g., when the risk of the hypoglycemic event matches or is above a particular probability). For example, the process 700 may be performed by one or more elements of the glucose level control system 510. In some cases, at least certain operations of the process 700 may be performed by a separate computing system that receives indications of blood glucose levels of the subject 512 from the glucose level control system 510 and/or indications of hypoglycemic events (or identified above threshold hypoglycemic risk events). Although one or more different systems may perform one or more operations of the process 700, to simplify discussions and not to limit the present disclosure, the process 700 is described with respect to particular systems.

The process 700 begins at block 702 where the glucose level control system 510 receives a glucose level of a subject 512. Receiving the glucose level may include receiving a glucose level signal corresponding to a glucose level of the subject. The glucose level signal may be received from the glucose sensor 516 (e.g., a CGM sensor). Alternatively, or in addition, the glucose level may be received from a user that provides the glucose level to the glucose level control system 510 via a user interface, such as a user interface generated by the processor 530 that may be output on a touchscreen by the touchscreen controller 538. The glucose level received from the user may be a glucose level measured using an alternative sensor or measurement mechanism (e.g., diabetes measurement strips) that may be used in place of the glucose sensor 516.

At bock 704, the glucose level control system 510 determines based at least in part on the glucose level that a triggering event for raising the blood glucose level of the subject 512 has occurred. The triggering event may include a determination that a hypoglycemic event or an episode of hypoglycemia is present or is occurring in the subject 512. Alternatively, or in addition, the triggering event may include a determination that there is an impending risk of hypoglycemia in the subject 512, or an impending risk that a hypoglycemic event will occur within a particular amount of time in the subject 512. The determination of the hypoglycemic event or the risk of a hypoglycemic event occurring may be determined by comparing the glucose level of the subject to a glucose threshold. Alternatively, or in addition, the determination of the hypoglycemic event or the risk of a hypoglycemic event occurring may be determined by comparing a trend and/or rate of change (e.g., rate of decrease) in the glucose level to a threshold. In some cases, the particular blood glucose level and the trend in the blood glucose level may be combined to determine a risk of hypoglycemia. For example, if the glucose level is low (e.g., below a particular threshold, such as 60 mg/dL), but a determined trend in the glucose level is upwards, then a risk of hypoglycemia may be lower than if the glucose level is above the threshold, but the determined trend in the glucose level is downwards towards a threshold. In some cases, the threshold(s) used to determine whether a hypoglycemic event is occurring or to determine that there is an above threshold risk of hypoglycemia occurring may vary based on physiological characteristics of the subject 512. The physiological characteristics may be based on physiological characteristics associated or shared among groups of patients (e.g., gender, age, weight) or may be specific to the particular subject 512. For example, thresholds associated with a risk of hypoglycemia may be determined based on determined glucose levels of the subject 512 during prior occurrences of hypoglycemia as determined by the glucose level control system 510 or based on clinical data specific to the subject 512.

In response to the triggering event at the block 704, the glucose level control system 510 determines an amount of counter-regulatory agent at block 706. The glucose level control system 510 may determine the amount of counter-regulatory agent based at least in part on the blood glucose level of the subject 512, the amount or percentage of risk of hypoglycemia occurring (e.g., a 99% risk or probability of hypoglycemia may trigger a larger counter-regulatory agent dose than a 75% risk or probability of hypoglycemia), physiological characteristics of the subject 512, a trend in the blood glucose level of the subject 512, or a type of counter-regulatory agent.

In some cases, the glucose level control system 510 may use a delivery device 514-1 to deliver the determined amount of counter-regulatory agent to the subject 512. The counter-regulatory agent may be delivered to the subject 512 in response to the impending risk of hypoglycemia or the episode of hypoglycemia, and/or in response to the glucose level satisfying or falling below a threshold glucose level. The threshold glucose level or the determination of whether to deliver the counter-regulatory agent may be based on physiological characteristics of the subject 512 and/or the risk tolerance of the subject 512 to a hypoglycemic event. It should be understood that, in the present context, risk tolerance generally does not refer to a user's subjective propensity for risk. Instead, the risk tolerance is typically an objective determination of how likely the subject 512 is to have a hypoglycemic event, or for symptoms of hypoglycemia to occur, when the blood glucose level of the subject 512 is at a particular level. This risk tolerance may be determined based on a history of hypoglycemia, or lack thereof, in the subject 512 at particular blood glucose levels and/or based on clinical data obtained for the subject 512.

In other cases, the glucose level control system 510 may not deliver counter-regulatory agent to the subject 512 because, for example, the glucose control system 510 may not be capable of delivering counter-regulatory agent or because the cartridge holding the counter-regulatory agent may be empty or have less than a threshold amount of counter-regulatory agent remaining.

At block 708, the glucose level control system 510 determines a dose of carbohydrate therapy based at least in part on the counter-regulatory agent. The carbohydrate therapy may refer to carbohydrates consumed to prevent or respond to an occurrence of hypoglycemia. The carbohydrates may include any type of carbohydrate that the subject 512 may consume to prevent or respond to an occurrence of hypoglycemia, and typically includes fast-acting carbohydrates, which may include sugary foods that are easily converted into sugars in the human body. For example, the carbohydrate may be a candy bar, soda, fruit juice, or other foods that may have a lot of sugar or refined sugars.

Determining the dose of carbohydrate therapy may include accessing a mapping between the counter-regulatory agent and carbohydrates. This mapping may be stored in, and accessed from, the memory 540 and/or may be accessed from another computing device. The glucose level control system 510 may determine the dose of carbohydrate therapy based at least in part on the mapping and the amount of the counter-regulatory agent. In some cases, the mapping may vary based on the type of counter-regulatory agent and/or the type of carbohydrates. The type of counter-regulatory agent may be identified by a user or may automatically be determined based on a medicament cartridge installed or inserted into the glucose level control system 510. Further, the type of carbohydrates may be specified by a user and may include an identity of the type of carbohydrates usually consumed by the subject 512 when responding to an occurrence or a risk of an occurrence of hypoglycemia. For example, the user may specify, via a user interface, whether the subject usually consumes a candy bar or fruit juice, or the size of the carbohydrate usually consumed when responding to an occurrence or a risk of an occurrence of hypoglycemia.

In some cases, the mapping between the counter-regulatory agent and carbohydrates may be generated based on a clinical comparison of the counter-regulatory agent to the carbohydrates. Alternatively, or in addition, the mapping may be based at least in part on a physiological characteristic of the subject 512.

The mapping may be stored in a lookup table or other data structure that can store relationships between different carbohydrates and counter-regulatory agents. The mapping may be between different quantities and/or types of carbohydrates and different quantities and/or types of counter-regulatory agent. Alternatively, or in addition, the mapping may be a formula that relates the carbohydrates to the counter-regulatory agent or vice versa. For example, the glucose level control system 510 may use the determined amount of counter-regulatory agent as an index to a lookup table to determine a corresponding quantity of carbohydrates. Alternatively, the glucose control system 510 may apply the determined amount of counter-regulatory agent to a formula to calculate a corresponding quantity of carbohydrates. This formula may be generated based on the type of counter-regulatory agent and/or carbohydrates, physiological characteristics of the user, and/or clinical data.

In some cases, the mapping may vary based on the glucose level control system 510. For example, the glucose level control system 510 may include a first mapping when the glucose level control system 510 (or medicament pump thereof) is a bi-hormonal pump configured to deliver insulin and counter-regulatory agent therapy to the subject, and may include a second mapping when the glucose level control system 510 is not configured to deliver the counter-regulatory agent therapy to the subject 512. In some cases, the glucose level control system 510 may store both mappings in the memory 540. For example, the glucose level control system 510 may use the first mapping when counter-regulatory agent is available and may use the second mapping when counter-regulatory agent is not available. The mappings may vary for a number of reasons including because a bi-hormonal glucose level control system 510 may more precisely control the occurrence of hypoglycemic events due to the availability of counter-regulatory agent, which may therefore alter the frequency and type of carbohydrates that a subject may consume.

At block 710, the glucose level control system 510 outputs an indication of the dose of carbohydrate therapy. Outputting the indication of the dose of carbohydrate therapy may include outputting an indication of the dose of carbohydrate therapy on a display for presentation to a user. Further, the indication of the dose of carbohydrate therapy may be transmitted to another computing system for display or aggregation with other therapy data associated with the subject 512, such as therapy data used by a clinician to help manager the subject's 512 care. In some cases, the indication of the dose of carbohydrate therapy may be included in a report corresponding to care of the subject 512.

In certain embodiments, the operations of the process 700 are performed or repeated over a period of time. For example, the operations associated with the block 702-708 may be repeated one or more times over the period of time. In such cases, the determined doses of carbohydrate therapy may be aggregated for the period of time to determine a total carbohydrate therapy for the period of time. Further, the block 710 may include outputting an indication of the dose of carbohydrate therapy for each individual time that a dose of carbohydrate therapy is determined and/or the aggregated determined doses of carbohydrate therapy for the period of time. The period of time may be any time period. For example, the period of time may be a day, week, month, year, since the subject 512 began using the glucose level control system 510, since a user obtained or ceased obtaining access to a counter-regulatory agent, or any other period of time. In some cases, the period of time is defined by the occurrences of hypoglycemic events or occurrences of the risk of hypoglycemia satisfying a threshold. For example, the period of time may be the time associated with 5, 10, 15, 100, or any other number of hypoglycemic events or occurrences of the risk of hypoglycemia satisfying a threshold.

The indication of total carbohydrate therapy may correspond to a reduction in carbohydrates consumed by the subject 512 because, for example, of the availability of counter-regulatory agent to the glucose level control system 510, and consequently, the subject 514. Thus, the indication of total carbohydrate therapy may correspond to a reduction in carbohydrates achievable by an availability to the subject 512 of the counter-regulatory agent. Further, the indication of total carbohydrate therapy may correspond to an amount of counter-regulatory agent provided or that can be provided to the subject as a substitute for carbohydrates.

The particular carbohydrates consumed, or the amount of carbohydrates consumed by each subject or during each hypoglycemic event, may vary. For example, a subject 512 may consume a particular candy bar when the subject's 512 measured blood sugar level is too low or when the subject feels that the blood sugar level is likely low (e.g., begins to feel some hypoglycemic effects). The subject may consume the whole candy bar or may consume a portion. Some of the candy bar may be lost to the subject (e.g., fall on the ground). In other cases, the subject may have different candy bars available, or other refined sugar sources, during different hypoglycemic events. Thus, even though there may be an objective mapping between carbohydrates and counter-regulatory agent, the amount of carbohydrates consumed or avoided due to the availability of counter-regulatory agent may vary for each hypoglycemic event. Accordingly, the indication of total carbohydrate therapy avoided, or that could be avoided if counter-regulatory agent were available, may indicate a range of carbohydrates that may potentially be replaced by the availability of counter-regulatory agent.

In some cases, the indication of carbohydrate therapy or total carbohydrate therapy may include one or more of an indication of calories, an indication of carbohydrates, an indication of a measure of sugar, an indication of a quantity of food, or an indication of weight of the subject attributable to the carbohydrate therapy. The indications may be associated with what is consumed due to a lack of counter-regulatory agent, or what is avoided based on the availability of counter-regulatory agent. For example, the indication of calories may be the number of calories not consumed because of the presence of the counter-regulatory agent. Advantageously, the availability of therapy information relating to the carbohydrate therapy or avoided carbohydrate therapy can assist in patient care. For example, a subject can reduce refined sugar consumption that can have a number of health consequences. Further, a healthcare provider can better help a subject control his or her weight based on the carbohydrate information.

The indication of carbohydrate therapy may be presented to a user in any presentable form. For example, the indication of carbohydrate therapy may be presented as a table, a chart, a graph, a histogram, or other data presentation tool for indicating the reduction in carbohydrates over time that is achieved by the presence of counter-regulatory agent or that could be achieved by the use of counter-regulatory agent for the particular subject 512. It should be understood that the indication of carbohydrate therapy data may vary for different users due to differences in physiological characteristics of the users, differences in the diabetes of each user, differences in lifestyle of each user, among other factors. Advantageously, by using the glucose level control system 510 to track the carbohydrate therapy of the subject 512 or to determine the carbohydrate therapy avoided or avoidable associated with counter-regulatory agent, management of the subject's 512 blood glucose level can be personalized.

Additional Carbohydrate Therapy Equivalence Tracking Embodiments

People with diabetes often consume oral carbohydrates for the purpose of treating or preventing hypoglycemia. Such extra carbohydrates can have unhealthy consequences, contributing to weight gain being one of them. Having a bihormonal glucose-control system that infuses a counter-regulatory agent (e.g., Glucagon) to reduce the frequency, extent, and duration of hypoglycemia can significantly reduce the amount of oral carbohydrates that are needed "medicinally" to treat or prevent hypoglycemia Certain embodiments of the present disclosure relate to a method for translating an amount of online counter-regulatory dosing (e.g. glucagon) computed by an autonomous glucose-control system to an amount of carbohydrates that the user is estimated to have been spared from needing by virtue of the counter-regulatory dosing, or that the user would be spaced from needing if the user had access to the counter-regulatory agent. In a bihormonal autonomous glucose-control system that infuses both insulin and a counter-regulatory agent/hormone, the method may include a mapping between the online counter-regulatory dosing, which was delivered to treat or prevent low glucose levels, and oral carbohydrates that are estimated to have otherwise been required to achieve a comparable safe control situation (had the counter-regulatory dosing not been delivered). In an insulin-only autonomous glucose-control system, where doses of a counter-regulatory agent/hormone are not delivered, but are still computed online, the method may include a mapping between the computed online counter-regulatory dosing and an estimated amount of oral carbohydrates that the subject will likely have been spared from needing to consume to treat or prevent low glucose levels had the counter-regulatory agent been available and its doses actually delivered.

Without loss of generality, embodiments disclosed herein include an autonomous glucose-control system where the counter-regulatory agent is glucagon. However, other medicaments and/or counter-regulatory agents may be utilized. The method may include relating computed online glucagon dosing with consumed oral carbohydrates for the treatment or prevention of low glucose levels ("treatment carbs") as observed in real use (e.g., during clinical studies) in the insulin-only configuration, and relating the relationship between the counter-regulatory agent and carbohydrates to a similar relationship between delivered online glucagon doses (or other counter-regulatory agent) and similarly consumed oral carbohydrates in the bihormonal (insulin-glucagon) configuration.

Using data gathered from real use (e.g., clinical studies), a relationship between the consumed treatment carbs in an insulin-only configuration, $C_{io}$, and the online computed (but not delivered) glucagon dosing, Gc, can be described by the relationship $C_{io}=R_{io}(x)*Gc$, where $R_{io}(x)$ may be a relating factor that can be a function of several dependencies that are included in vector x. Such dependencies can include the specific insulin and/or glucagon being used (e.g., their clinical properties), and/or the pharmacokinetic settings assumed by the control system in relation to insulin and/or glucagon. The dependencies can also include the user's body mass and the glucose target used by the glucose-control system. In some embodiments, Rio(x) may be a constant, or Rio(x)=Rio, for a system exhibiting limited variation in the relationship between $C_{io}$ and $G_c$ (e.g., due to limited effect, or limited or no variation in the associated dependencies).

Similar to the insulin-only configuration, from real-use data, a relationship between the consumed treatment carbs in a bihormonal (insulin-glucagon) configuration, $C_{bh}$, and the online delivered glucagon dosing, $G_d$, can be described by the relationship $C_{bh}=R_{bh}(x)*G_d$, where $R_{bh}(x)$ may be described in a similar fashion to $R_{io}(x)$ above. In some cases, the quantities $C_{io}$, $G_c$, $C_{bh}$, and $G_d$ can refer to daily amounts, as averaged over some period of use (e.g., a week). In some cases, the quantities $C_{io}$, $G_c$, $C_{bh}$, and $G_d$ can refer to average daily amounts per body mass of the user, in which case dependency on body mass can be eliminated from x.

In cases where $G_c$ is computed, but no glucagon is actually delivered in an insulin-only system, $G_c$ has no effect on glucose insofar as treating or preventing low glucose levels, which in turn is generally expected to invoke further computed glucagon dosing (e.g., goes towards increasing the magnitude of $G_d$ for a given situation). By contrast, since $G_d$ is delivered in a bihormonal system, it is expected to have an effect in preventing or reducing the frequency, extent, or duration of low glucose levels, which in turn is expected to limit the overall magnitude of glucagon dosing (e.g., limits $G_d$ for a given situation). As such, for a given set of dependencies, it is generally expected that $G_c>G_d$ between the two system configurations. Likewise, since $G_c$ has no effect in combating low glucose levels while $G_d$ does have such an effect, it is expected that treatment carbohydrates $C_{io}>C_{bh}$, when comparing the two system configurations.

If one can ideally relate, for a given real-use case of an insulin-only system with $G_c$, what the corresponding $C_{io}$ would have been for the same real-use scenario, had the computed online glucagon dosing actually been delivered as $G_d$, one can project an estimate that the user would have required "$C_{io}-C_{bh}$" less treatment carbs (e.g., would have saved that much), had they instead been using a bihormonal system (with the same insulin controller), where glucagon would have been delivered. Conversely, if one can ideally relate, for a given real-use case of a bihormonal system with $G_d$, what the corresponding $C_{bh}$ would have been for the same real-use scenario, had the delivered online glucagon dosing not been delivered but only computed as $G_c$, one can project an estimate that the user had actually avoided the need to take "$C_{io}-C_{bh}$" additional treatment carbs, had they been instead using an insulin-only system (with the same insulin controller), where glucagon would not have been delivered. It should be understood that the above calculations are an estimate in an ideal situation as, in practice, it is not possible to have a re-run of a past real-use scenario to obtain such ideal relationships.

For practical implementation, real-use cases where the insulin-only system is used can be re-simulated while assuming a bihormonal system is available, where glucagon is assumed to be delivered. Since the control system may take delivered doses into account when issuing subsequent nearby glucagon doses, the simulated glucagon dosing may exhibit a reduction relative to the original $G_c$ of the insulin-only system. With the glucose profile kept unaltered in a simulation, the simulation may lack reflecting any resulting glucose excursions in response to the assumed delivered glucagon dosing. The simulation in turn may lack reflecting the full reduction in glucagon dosing down to $G_d$ that may have been observed if the glucose excursions had in fact benefited from glucagon being delivered. Thus, the reduced glucagon dosing that is observed in the simulation, pseudo delivered glucagon $\hat{G}_d$, may arguably be exaggerated in magnitude relative to what would have been the "real $G_d$". As described above, based on prior analyses $G_c$ can be mapped to a corresponding amount Cm in the insulin-only configuration, and $\hat{G}_d$ can be mapped to a corresponding amount $\hat{C}_{bh}$ in the bihormonal configuration. The simulation results, therefore, can map the reduction "$G_c-\hat{G}_d$" to an estimate "$C_{io}-\hat{C}_{bh}$" of treatment carbs that the user would spare had they been using the bihormonal system. The estimates may be conservative estimates. Repeating the simulation analyses across a variety of real-use cases that span the range of $G_c$ observed in practice provides a global mapping between them and the associated range of (in some cases, conservative) estimates "$C_{io}-\hat{C}_{bh}$" of treatment carbs that the user would likely not need to consume had they been using the bihormonal system. Conversely, the mapping can be utilized when a bihormonal system is being used, where the observed dosing $G_d$ is mapped back to a pseudo computed glucagon $\hat{G}_c$ and the resulting associated difference "$\hat{C}_{io}-C_{bh}$" provides a (in some cases, conservative) estimate of the treatment carbs that the user had likely saved by virtue of being on the bihormonal system.

Certain embodiments includes a system that comprises a controller for automatic control of a blood glucose level of a subject. The controller may be operative to generate an insulin dose control signal based on time-varying glucose levels of the subject as represented by a glucose level signal over time. The glucose level signal can be generated by a glucose sensor operative to continually sense a glucose level of the subject. The insulin dose control signal may control the delivery of doses of insulin by a delivery device. Further, the controller can operate at a regular frequency to generate an insulin dose control signal to regulate the glucose levels in the subject. During online operation, the controller can employ a control algorithm that generates a glucagon dosing signal, which may be mapped to an associated amount of oral carbohydrates.

The oral carbohydrates may be associated with the prevention or treatment of low glucose levels. Further, the mapping between the glucagon dosing signal and the oral carbohydrates may be derived from analysis of clinical data.

The glucagon dosing signal may be computed, but not delivered in an insulin-only system configuration. In contrast, the glucagon dosing signal can be computed, and glucagon can be delivered in an insulin-glucagon system configuration. The computed glucagon dosing in an insulin-only system configuration can be mapped to an amount of oral carbohydrates that is estimated to have been saved had glucagon dosing been delivered if an insulin-glucagon system configuration had instead been used. The delivered glucagon dosing in an insulin-glucagon system configuration can be mapped to an amount of oral carbohydrates that is estimated to have been saved if an insulin-only system configuration had instead been used. The mapping may be dependent on the clinical properties of the insulin and glucagon being used, and settings in the control system related to the action and effect of insulin and glucagon. Further, the mapping may be dependent on the subject's body mass.

Backup Therapy Protocol Generation

An ambulatory medicament device, such as a blood glucose control system (e.g., an insulin pump or a combined insulin and counter-regulatory agent (e.g., Glucagon) pump), can provide personalized therapy to a subject. In other words, the ambulatory medicament device may provide medicament that is specific to a subject's physiology, condition, activity, and the like. Further, some ambulatory medicament device's monitor a condition of the subject to determine when to provide therapy, what type of therapy to provide (e.g., insulin or counter-regulatory agent therapy), and/or how much therapy to provide. The therapy provided by the ambulatory medicament device may be ongoing and, in some cases, lifesaving. Thus, it is important that ambulatory medicament device function uninterrupted.

Despite best efforts, sometimes therapy by the ambulatory medicament device is interrupted. For example, the ambulatory medicament device may break, a subject may run out of or not have access to a necessary disposable (e.g., a replacement insulin cartridge, a site kit for changing the site of the ambulatory medicament device, a replacement battery, and the like), or the subject may forget to charge a battery of the ambulatory medicament device or not be in a location where a power source is available to charge the ambulatory medicament device. Thus, there are occasions when the ambulatory medicament device may not be available or may need replacing.

When the ambulatory medicament device is not available, or when a replacement (temporary or permanent) ambulatory medicament device is being used, it may be desirable to have an indication of the therapy settings from the ambulatory medicament device. For example, if a user (e.g., a subject, healthcare provider, parent, or guardian) is providing alternative therapy (e.g., injection therapy) while the ambulatory medicament device, it may be necessary to know the quantity of therapy to provide under particular circumstances or at particular times.

In some cases, a healthcare provider may have access to therapy information that may have been previously determined, for example, via clinical testing. This therapy information may include any type of information that can be used to determine therapy to provide to a subject at a particular time or under particular conditions. For example, the therapy information may indicate a setpoint insulin range for the subject, a quantity of insulin to provide to the user to adjust glucose levels, an amount of time for insulin to reach max concentration in the subject, or any other information that might impact the timing or amount of dosing of a medicament.

The therapy information available to the healthcare provider may be insufficient. For example, the subject may not be able to reach the healthcare provider to obtain the therapy information at a point in time when the information is needed. Further, in some cases the information may be outdated because, for example, the ambulatory medicament device may have refined the therapy over time. If the refinements have occurred recently, it is possible that the outdated values of the healthcare provider may be sufficient until a replacement ambulatory medicament device can repeat the refinement process of the original ambulatory medicament device. In other cases, the outdated therapy information may be insufficient because, for example, the refinements were significant or the subject may have had physiological changes (e.g., weight gain or weight loss, or metabolism changes) since the last time a clinical test was performed. Using outdated therapy information may be less effective and may cause discomfort or harm to a subject.

Certain embodiments of a system disclosed herein can generate backup therapy data. Using the backup therapy data, a subject (or user) can perform injection therapy or configure a replacement ambulatory medicament device if the subject's current device malfunctions. By using the backup therapy data, the subject can maintain a level of therapy care that matches or more closely matches what was being provided by the ambulatory medicament device than clinical data, which may be outdated if available at all.

The system can include an automated blood glucose control system (e.g., the glucose level control system 510) configured to generate a backup therapy protocol comprising insulin therapy instructions derived from autonomously determined doses of insulin. During normal operation, the system may receive glucose level signals from a sensor operatively configured to determine glucose levels in a subject. The sensor can include any type of sensor that can determine glucose levels. For example, the sensor may be a Continuous Glucose Monitoring (CGM) sensor.

Using the determined glucose levels, the system may autonomously determine and/or generate a dose control signal using a control algorithm. The determination and/or generation of the dose control system may be performed without any user action or interaction with the blood glucose control signal. In some cases, the lack of user action or interaction with the blood glucose control system refers to conscious action and may exclude sensor measurements of physiological characteristics of the subject. The control algorithm may autonomously determine doses of insulin to be infused into the subject for the purpose of controlling blood glucose of the subject based at least in part on the glucose level signal. The control algorithm may include any type of control algorithm.

For example, the control algorithm may be a biexponential pharmacokinetic (PK) model that models the accumulation of insulin doses in the blood plasma of the subject. The automated blood glucose system may control delivery or administering of insulin or a counter-regulatory agent based on the bi-exponential PK model and one or more blood glucose measurements of the subject. The bi-exponential PK model may model the absorption of subcutaneously administered insulin into blood and/or a rate of diminishing glucose in the blood. The bi-exponential PK model over time may be represented by the following equation:

$$p(t)=KU_0(e^{-\alpha_1 t}-e^{-\alpha_2 t}) \quad (1)$$

where $U_0$ is the subcutaneous dose in units (U), K is a scaling constant, and $\alpha_1$ and $\alpha_2$ are time constants.

As an alternative example, the control algorithm may include a linear algorithm that models diminishing glucose or the accumulation of glucose in the subject based on a linear reduction rate. For example, the control algorithm may determine that a particular dose, D, of insulin is to be administered to the subject. The control algorithm may then estimate that 0.25*D of the insulin is absorbed into the blood plasma per hour over 4 hours. Similarly, the control algorithm may estimate that the insulin diminishes at a rate of 0.33*D per hour over three hours upon the insulin reaching maximum concentration within the blood plasma.

Regardless of the control algorithm used, the automated blood glucose control system may administer insulin and, in some cases, a counter-regulatory agent one or more times over a particular time period. There may be multiple reasons and/or triggers that cause the automated blood glucose control system to supply insulin. For example, the automated blood glucose control system may provide a basal does of insulin on a periodic basis in an attempt to maintain a steady blood glucose level in the blood plasma of the subject. As another example, the automated blood glucose control system may supply mealtime boluses of insulin to account for an expected amount of glucose to be consumed as part of a meal. The mealtime bolus may be an amount specified by a user or may be an amount of insulin administered in response to an indication of meal size by the subject. This indication of meal size may be subjective. In some cases, the size of the bolus of insulin for an identified meal size may be a fixed or constant value. In some other cases, the size of the bolus of insulin for an identified meal size may vary over time as the automated blood glucose control system learns or refines the amount of insulin to administer to a subject to keep the subject's blood glucose within a target setpoint. The automated blood glucose control system may learn or refine the optimal insulin to administer based on a comparison of expected blood glucose level measurements to actual blood glucose level measurements when the subject (or other user) makes a subjective identification of meal size. In addition to basal and mealtime boluses of insulin, the automated blood glucose control system may also supply correction doses of insulin to the subject based on the glucose level signal. The correction doses of insulin may be supplied in response to a model predictive controller (MPC) determining or estimating that a user's level of insulin is expected to fall below a threshold in some future period of time based on blood glucose level readings. The MPC may execute a control algorithm that can regulate glucose concentration to a reference setpoint while simultaneously minimizing both the control signal aggressiveness and local insulin accumulation. A mathematical formulation describing the subcutaneous accumulation of administered insulin may be derived based on nominal temporal values pertaining to the pharmacokinetics of insulin in the subject. The mathematical formulation may be in terms of the insulin absorption rate, peak insulin absorption time, and/or overall time of action for the insulin (or another medicament). Examples of an MPC controller that may be used with embodiments of the present disclosure are described in U.S. Pat. No. 7,806,854, issued on Oct. 5, 2010, the disclosure of which is hereby incorporated by reference in its entirety herein for all purposes.

The automated blood glucose control system may track insulin therapy administered to the subject over a tracking period. Although the tracking period is not limited in length and may generally be any period of time, typically the tracking period is at least a minimum period of time sufficient for the automated blood glucose control system to learn or refine the amount of medicament (e.g., insulin) to administer to the subject under particular conditions (e.g., when particular blood glucose levels are detected or when particular meal sizes are identified). For example, the automated blood glucose control system may initially administer 6 units of insulin for lunch and 10 units of insulin for dinner. These initial values may be set be a healthcare provider and/or a subject based, for example, on clinical data for the subject. However, over time (e.g., 3-5 days), the automated blood glucose control system may determine that providing 7 units of insulin for lunch and 8 units of insulin for dinner maintains the subject's blood glucose level closer to the median of the setpoint range than did the initial configuration. Although not limited as such, generally each unit of insulin is $\frac{1}{100}^{th}$ of a milliliter of insulin.

As indicated, the tracking period can be any length of time. For example, the tracking period could be 1 day, 3 days, 5 days, 7 days, anything in between, or more. Typically, the tracking period is at least long enough to provide sufficient time to learn or refine initial settings of the automated blood glucose control system for the subject. In some cases, the tracking period may be 1 or 2 days. In other cases, the tracking period may be from a particular time period until a current time period. For example, the tracking period may be from the start of therapy until a current point in time. In other cases, the tracking period may be a moving or shifting window. For example, the tracking period may be the least week, two weeks, month, or year. Further, for non-blood glucose systems, the tracking period may differ based on the amount of time sufficient to determine or refine medicament control values for the subject. In some cases, the tracking period may a window of a particular length. This window may be a moving window. For example, the window may be the previous 7 days. As time passes, the window moves to continue to encompass the previous 7 days.

Tracking the insulin therapy may include storing the autonomously determined doses of insulin delivered to the subject. These autonomously determined doses of insulin may include one or more of basal insulin doses, mealtime insulin boluses, or correction insulin doses. Moreover, tracking the insulin therapy may including tracking the type of insulin used. The type of insulin may include any type of insulin, such as fast-acting insulin (e.g., Lispro, Aspro, or Glulisin), regular or short-acting insulin (e.g., Humulin R, Novolin R, or Velosulin R), intermediate-acting insulin (e.g., Humulin N, Novolin N, ReliOn), long-acting insulin (e.g., detemir (Levemir), and glargine (Basaglar, Lantus)), or Ultra long-acting insulin (e.g., degludec (Tresiba), glargine u-300 (Toujeo)). Further, tracking the insulin therapy may include tracking counter-regulatory agent (e.g., Glucagon) therapy.

In some cases, tracking the insulin therapy may include calculating average therapy provided over a period of time (e.g., over the tracking window). For example, the tracking the insulin therapy may include determining a moving average of the past 7 days of nominal basal doses during each dosing interval. Assuming basal therapy is provided every five minutes, the moving average may be calculated based on the previous 288 doses (e.g., over 1 day) or 2016 doses (e.g., over 7 days). This calculation can be used to obtain a basal rate profile for backup therapy. In some cases, the time period may be broken up into different time segments that may be associated with different rates of therapy. For example, there may be 4 basal therapy periods (e.g., 10 pm-4 am, 4 am-10 am, 10 am-4 pm, and 4 pm-10 pm). Thus, a separate moving average may be calculated for each of the basal therapy periods over a day, or over some other time period (e.g., 7 days). The calculated averages may be used to calculate a backup basal rate that can be used to program an automated glucose control system. Further, the basal rate profile may include aggregating the doses across the day to determine a dose of long-acting insulin that can be used for injection therapy.

Similar to the basal therapy, a moving average of correction doses can be calculated to determine a correction bolus of insulin to supply via a pump or injection therapy. Alternatively, or in addition, the moving average of correction doses in combination with measurements of blood glucose of the subject over time may be used to determine a rate of change of blood glucose from a unit of insulin provided during correction therapy.

Mealtime boluses may also be calculated using a moving average. Further, a separate moving average may be calculated for each meal (e.g., breakfast, lunch, and dinner) dose over some period of time (e.g., 7 previous days of mealtimes). In some cases, each of the moving averages may be calculated using different windowing functions. For example, the moving average may be calculated using a Hann window or a Hamming window. In some cases, different levels of dosing may be determined for different meal sizes and different doses may be determined for different meals. In some cases, different meals (e.g., breakfast vs lunch) may have different dosing despite similarity in size due, for example, to differences in the subject's blood glucose levels when they wake up versus when they usually have lunch, or because differences in types of foods consumed at breakfast versus lunch. Further, in some cases, differences in metabolisms of different subjects may result in different mealtime boluses.

The insulin therapy may be stored in a therapy log, or any other type of data structure. Further, the insulin therapy may be stored in a memory of the automated blood glucose system, on a companion device, on a computing device of the subject or user (e.g., a laptop or desktop), in a cloud computing environment, or in any other storage system capable of receiving the insulin therapy information from the automated blood glucose control system.

Using the therapy log or tracked insulin data, the automated blood glucose system, or a computing system with access to the therapy log or tracked insulin data, may generate a backup insulin therapy protocol. The backup insulin therapy protocol may include a backup injection therapy protocol or a backup pump therapy protocol. The backup injection therapy protocol may include one or more amounts of insulin (or other medicament) to administer using injection therapy (e.g., manually provided shots) at one or more times to help maintain the subject's condition within a normal or desired physiological range or condition. The backup pump therapy protocol may include data and/or instructions for a replacement medicament pump of the same type or of a different type to supply therapy to the subject. The replacement medicament pump may be a permanent replacement or a temporary replacement.

The backup pump therapy protocol may be the same as and/or include the same type of information as the backup injection therapy protocol. Alternatively, or in addition, the backup pump therapy protocol may include different values than the backup injection therapy protocol. For example, the backup pump therapy protocol may include an indication of basal therapy to provide periodically on relatively short increments (e.g., every 5 minutes, every half hour, every hour, etc.). Because an insulin pump may automatically administer insulin, it is possible to provide a steady or periodic drip of insulin. It may be impractical for a subject using injection therapy to administer insulin manually on similar short increments. Instead, a user might administer therapy on a less regular basis (e.g., once every roughly 4-5 hours or 6-8 hours, prior to mealtimes, after waking, and/or before sleeping, etc.). Accordingly, the backup therapy protocol for a pump and for injection may differ. Further, the type of insulin used or identified in the backup protocol may differ. For example, the backup protocol may call for use of long-acting insulin, such as, for example, insulin glargine, or intermediate-acting insulin, such as, for example human recombinant insulin.

In some cases, the backup pump therapy protocol may be used to manually refine pump settings for a replacement blood glucose control system to be used by the subject. In other cases, the replacement blood glucose control system may automatically configure itself based on the backup therapy protocol. For example, a user may cause the backup therapy protocol to be provided to the replacement blood glucose control system, which may use the information to self-calibrate.

Regardless of whether a backup protocol is generated or needed, collecting and analyzing therapy data for therapy provided by the automated blood glucose control system can be useful for helping to manage a subject's condition. For example, therapy data may be useful in determining whether the subject is satisfied with therapy provided by the automated blood glucose control system or whether the blood glucose control system is configured in a way that best matches the subject's lifestyle or therapy preferences (subjective or otherwise). One way to determine whether the blood glucose control system is providing desired therapy, or therapy at a desired rate, is to determine the frequency and/or magnitude of modifications made by the subject, or other user that may help manage a subject's therapy, to therapy provided by the automated blood glucose control system.

The automated blood glucose control system disclosed herein can track user modifications to a control parameter over a tracking period. The tracking period may include any time period described above for tracking therapy to generate a backup protocol. Further, the control parameter may include any type of control parameter that may affect the administering of therapy. For example, the control parameter may relate to a quantity of therapy, a timing of delivered therapy, a rate that therapy is delivered, or a trigger of when or whether to deliver therapy, among other control parameters. Moreover, the control parameters may directly affect the delivery of therapy (e.g., specify a time to deliver the medicament or a quantity of medicament to deliver) or may indirectly affect therapy (e.g., adjust a setpoint range to maintain blood glucose or a rate of insulin accumulation in the subject, which may be used to modify a control algorithm for administering therapy).

The user modifications may include any change to the control parameter or settings of the automated blood glucose control system. For example, the automated blood glucose control system may track each instance and/or the rate or percentage of times a user reduces or increases a control parameter (e.g., an amount of administered insulin). Further, tracking changes to the control parameter may including tracking how often a user pauses therapy or temporarily adjusted a target blood glucose range, or other control parameter. In addition, tracking changes to the control parameter may include tracking when a user makes changes to the control parameter. For example, the user may generally modify the control parameter at night, but leave the daytime parameter unchanged, or vice versa. In some cases, the automated blood glucose control system may track a subject's weight over time. The weight may be provided by a user and may affect the blood glucose control (e.g., an amount of insulin administered may be related to a subject's weight).

The automated blood glucose control system may generate a report that tracks user modifications to the control parameter. The report may comprise a measure of the frequency of increases and decreases from the stored control parameter value. Further, the report may include an indicator of a percentage of times a user modified a control parameter higher or lower than the stored control parameter value of the automated blood glucose control system over the tracking period. In some cases, the report indicates the number of times that the infusion of insulin is paused over the tracking period, or the speed (e.g., aggressiveness) that insulin is delivered to the subject.

Using this report, a clinician or other healthcare provider can determine whether modifications should be made to a control parameter to better manage a subject's therapy. For example, if it is determined that a subject is raising a blood glucose target level 4-5 times a week during an evening time or nighttime, the clinician may determine that the target setpoint for the evening should be adjusted to reduce the number of occurrences that a user manually adjusts therapy, or control parameter settings for therapy, provided by the automated blood glucose control system. In some cases, the subject may be adjusted therapy based on subjective reasons. In some such cases, the therapy report may enable the clinician or healthcare provider to train the subject on controlling his or her disease. In other cases, the clinician may determine that the subject has a different tolerance for blood glucose than initially determined or than an average subject and may adjust one or more control parameters of the automated blood glucose control system accordingly.

In some implementations, the automated blood glucose control system may automatically adjust one or more control parameters over time based on the report. For example, if the automated blood glucose control system determines that over a course of a month the subject adjusted lower a daytime target glucose range 20 out of 30 days, the automated blood glucose control system may modify a control parameter to have a lower setpoint range. In some cases, the automated blood glucose control system may communicate the change to a user, such as the subject, a parent or guardian, or a healthcare provider.

Example Backup Therapy Protocol Generation Process

Figure 8:
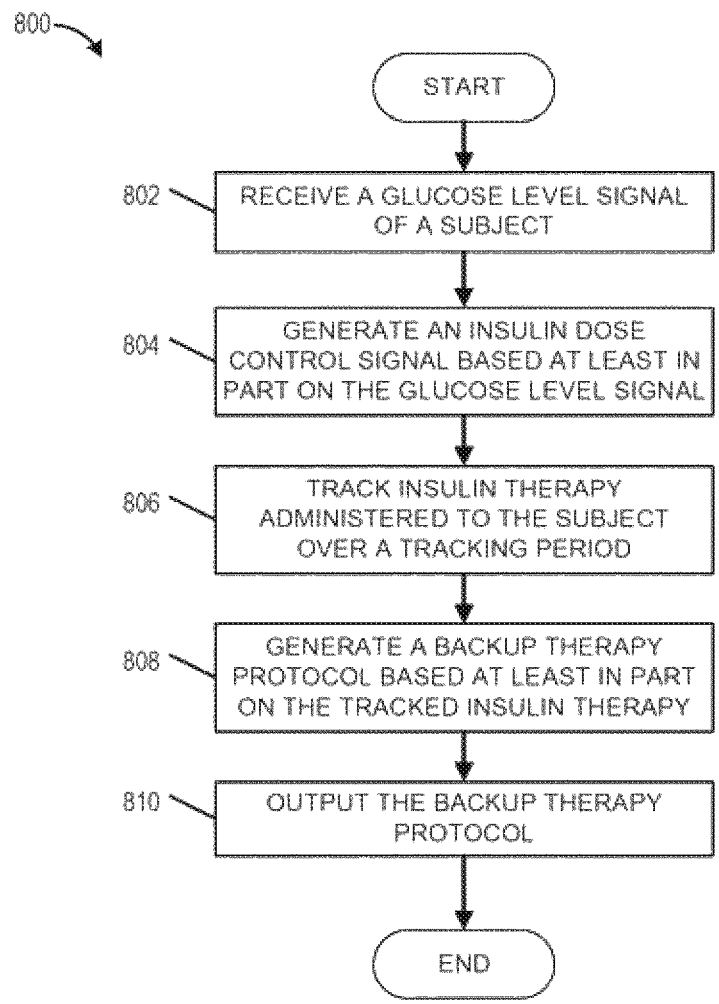
FIG. 8 presents a flowchart of an example backup therapy protocol generation process in accordance with certain embodiments.

FIG. 8 presents a flowchart of an example backup therapy protocol generation process 800 in accordance with certain embodiments. The process 800 may be performed by any system that can track medicament therapy (e.g., insulin therapy) provided to a subject over time and generate a backup therapy protocol that may be used if a glucose level control system 510 becomes unavailable. For example, the process 800 may be performed by one or more elements of the glucose level control system 510. In some cases, at least certain operations of the process 800 may be performed by a separate computing system that receives indications of medicament therapy provided to the subject 512 from the glucose level control system 510. Although one or more different systems may perform one or more operations of the process 800, to simplify discussions and not to limit the present disclosure, the process 800 is described with respect to particular systems.

The process 800 begins at block 802 where the glucose level control system 510 receives a glucose level of a subject 512. Receiving the glucose level may include receiving and/or determining a glucose level signal corresponding to a glucose level of the subject. The glucose level signal may be received from the glucose sensor 516 (e.g., a CGM sensor). Alternatively, or in addition, the glucose level may be received from a user that provides the glucose level to the glucose level control system 510 via a user interface, such as a user interface generated by the processor 530 that may be output on a touchscreen by the touchscreen controller 538. The glucose level received from the user may be a glucose level measured using an alternative sensor or measurement mechanism (e.g., diabetes measurement strips) that may be used in place of the glucose sensor 516.

At block 804, the glucose level control system 510 generates an insulin dose control signal based at least in part on the glucose level signal. In some cases, the insulin dose control signal may be a medicament control signal configured to control a medicament pump to administer medicament (e.g., insulin, counter-regulatory agent, or other medicament) to a subject 512. The dose control signal may be generated using a control algorithm configured to autonomously determine doses of insulin to be administered to or infused into the subject for the purpose of controlling blood glucose of the subject based at least in part on the glucose level or glucose level signal determined at the block 802.

At block 806, the glucose level control system 510 tracks insulin therapy administered to the subject 512 over a tracking period. The tracking period is typically at least one day and may be longer. For example, the tracking period may be 1 day, 2 days, a week, a month, several months, a year, any length of time between the foregoing examples, or even longer. In some cases, the tracking period may be continuous from a point in time when tracking begins. For example, the tracking period may encompass the entire usage lifetime of the glucose level control system 510 by the subject 512. In cases where the tracking period is set for a defined period of time (which may be modified for different iterations of the process 800), the process 800 may be repeated periodically, upon request, or upon a triggering event using a new tracking period, of equal or different length. The triggering event may include any event that may render a prior generated backup therapy protocol potentially out-of-date. For example, the triggering event may include a change in medicament type (e.g., different insulin or counter-regulatory agent formulations), a change in physiological characteristics of the subject 512 (e.g., a change in weight, or sensitivity to different glucose levels or medicament), or a change in average activity level of the subject 512.

Although the tracking period is typically at least one day enabling the glucose level control system 510 to determine a backup protocol based on data from a full cycle (e.g., waking and sleeping hours) of glucose level control system 510 use, in some cases, the tracking period may at least initially be less than a day. For example, an initial backup therapy protocol may be generated after a half-day's activity. This initial backup therapy protocol may be updated as more data becomes available throughout the day's (and, in some cases, subsequent day's) use of the glucose level control system 510.

In some cases, the tracking period may be defined by or based on a particular number of insulin administering events. For example, the tracking period may be defined by at least ten instances of generating an insulin dose based on a glucose level signal. As another example, the tracking period may be defined by a minimum number of meal events, correction dose events, and/or basal dose events. For instance, the tracking period may require 3 meals, or 3 meals of each meal type to occur, 2 correction doses, and/or 100 basal doses. It should be understood that the aforementioned number of doses is just an example, and the tracking period may include more or fewer dose amounts. Moreover, the tracking period may be defined or specified as a combination of time and occurrences of a particular number of doses of insulin.

In some cases, the tracking period may be variable. For example, if the glucose level control system 510 determines that the insulin dose therapy is inconsistent or erratic over the tracking period (e.g., due to inconsistent exercise or eating habits), the tracking period may be extended.

Tracking the insulin therapy may include storing the insulin dose control signal generated based at least in part on the glucose level signal at the block 804. Alternatively, or in addition, tracking the insulin therapy may include storing an indication of a quantity of insulin (or other medicament) corresponding to the insulin (or another medicament) dose control signal. The insulin dose control signal and/or the indication of the quantity of insulin may correspond to a dose of insulin delivered to the subject 512 as a basal insulin dose, a correction bolus of insulin, and/or as a mealtime bolus of insulin.

Storing the insulin dose control signal and/or the indication of the quantity of insulin may include storing the insulin dose control signal and/or the indication of the quantity of insulin in a therapy log or any other type of data structure in the memory 540 of the glucose level control system 510. Alternatively, or in addition, the glucose level control system 510 may store the insulin dose control signal and/or the indication of the quantity of insulin at a remote data store. This remote data store may be a local computing system with which the glucose level control system 510 may communicate (e.g., a laptop, desktop, smartphone, or other computing device of the subject 512 or a user). The glucose control system 510 may provide the insulin dose control signal data or the indication of the quantity of insulin to the local computing system via Bluetooth® or other near field communication services, or via a local network. Alternatively, or in addition, the remote data store may be a remote computing system that the glucose level control system 510 may communicate with over a wide area network, such as a wireless area network, a cellular network using IoT based communication technology, cellular communication technology, or any other communication network. In some cases, the wide area network may include the Internet. The glucose level control system 510 may include a wireless radio that enables it to communicate with the local or remote computing system. Further, the remote computing system may be a computing system of a data center or a cloud computing environment.

Whether a local or remote computing system, the glucose level control system 510 may establish a communication channel with the computing system. This communication channel may be an encrypted channel. Further the communication channel may be a direct end-to-end connection between the glucose level control system 510 and the computing system. Once the communication channel is established, the glucose level control system 510 may transmit the insulin dose control signal data or the indication of the quantity of insulin to the computing system.

Generally, the operations associated with the blocks 802-806 may be repeated multiple times throughout the course of the tracking period. For example, in some cases, an insulin dose control system associated with basal insulin may be generated up to 288 times a day. Accordingly, tracking the insulin therapy may include storing insulin does control signals and/or corresponding indications of quantities of insulin for a plurality of autonomously determined doses of insulin infused into the subject 512 throughout the tracking period.

Generally, counter-regulatory agent therapy includes administering a counter-regulatory agent (e.g., glucagon) when there is a risk or occurrence of hypoglycemia. Usually, the counter-regulatory agent is not supplied on periodic or daily basis. However, it can be useful to understand the amount and frequency that counter-regulatory agent is administered to the subject 512. For example, it may help a healthcare worker or user guide or adjust care for the subject 512. Further, tracking counter-regulatory agent use may help determine a minimum quantity of counter-regulatory agent that should be accessible to the subject 512, either in a bi-hormonal pump or for use in injection therapy. In some cases, the block 806 may include tracking the counter-regulatory agent administered during the tracking period. Tracking the counter-regulatory agent therapy may include storing an indication of autonomously determined doses of counter-regulatory agent delivered to the subject 512 responsive to the glucose level signal obtained at the block 802.

At block 808, the glucose level control system 510 generates a backup therapy protocol based at least in part on the tracked insulin therapy. The backup therapy protocol may be determined based on an average quantity or rate of insulin administered to the user over the tracking period, over different portions (e.g., breakfast, lunch, and dinner, or waking and sleeping hours, etc.) of the tracking period, or in response to particular events (e.g., when eating, when blood glucose level exceeds a threshold level, etc.). The backup therapy protocol may include a backup injection protocol and/or a backup pump therapy protocol. The backup injection protocol may provide a user (e.g., the subject 512, a parent or guardian, or other caretaker for the subject 512) with quantities of insulin that may be administered to the subject 512 via injection. Further, the backup injection therapy may indicate times that the insulin may be administered. For example, the backup injection therapy may indicate quantities of insulin to be administered at particular mealtimes. Further, the backup injection therapy may indicate an effect that a unit of insulin may have no the subject 512 enabling a user to calculate how much insulin to administer to the subject 512 when a blood glucose reading indicates that the glucose level of the subject 512 is too high (e.g., above a desired setpoint range).

Similar to the backup injection therapy protocol, the backup pump therapy protocol may provide a user (e.g., the subject 512, a parent or guardian, or other caretaker for the subject 512) with quantities of insulin that may be administered to the subject 512 via a medicament pump. Using the backup pump therapy protocol, a user may configure the medicament pump to administer the quantities of insulin identified. The backup pump therapy protocol may be used to configure the medicament pump when access to a CGM sensor is unavailable (e.g., the subject 512 does not possess a CGM sensor, or the medicament pump or CGM sensor has a fault, etc.). Further, the backup pump therapy protocol may be useful for providing an initial configuration to a replacement glucose level control system.

In some cases, the backup injection therapy protocol and the backup pump therapy protocol may be the same. However, often at least the recommended basal therapy settings may differ. It is generally not practicable for insulin to be administered to a subject 512 more than a few times a day via injection therapy. Thus, the backup injection therapy protocol may identify long acting insulin units or doses that may be administered on a limited basis (e.g., once or twice a day). However, the medicament pump may more easily administer insulin on a more than limited basis (e.g., every hour, every half hour, every 5 minutes, etc.). Thus, the backup pump therapy protocol may identify a basal rate of insulin that may be administered once every time unit (e.g., once per hour or once per 15 minutes, or once per five minutes), or continuously at a particular rate (e.g., 0.5 or 0.6 units) per time unit (e.g., per hour). Moreover, the backup pump therapy protocol may identity different rates for different portions of a day (e.g., one rate each half of the day, one rate each quarter of the day, or one rate during typical waking hours and one rate during typical sleeping hours for the subject, etc.).

In some cases, an initial backup therapy protocol may be generated at the block 808. The initial backup therapy protocol may be updated over time as additional insulin therapy data is obtained.

Generating the backup therapy protocol may include determining a number of long acting insulin units based at least in part on an average total basal insulin provided to the subject 512 per day over the tracking period. The averaged total basal insulin provided per day may be included in a backup injection therapy protocol as a single dose of long acting insulin that is configured to help maintain the basal insulin level of the subject 512 throughout the day. In some cases, the averaged total basal insulin provided per day may be included in a backup injection therapy protocol as multiple doses of insulin (e.g., 2 or 3 doses throughout the day).

Alternatively, or in addition, the basal insulin may be included in the backup therapy protocol, such as in a backup pump therapy protocol, as a dosage rate that may be supplied to a pump to provide a rate of basal insulin throughout the day. Further, in some cases, each day of the tracking period may be divided into a plurality of sub-periods. For example, each day of the tracking period may be divided into two, three, four, or more time periods, or equal or different length. In some such cases, generating the backup therapy protocol may include determining an hourly basal rate for each sub-period of the plurality of sub-periods. This hourly basal rate may be determined by averaging the corresponding sub-periods for each day of the tracking period. For example, if each day of the tracking period is divided into two sub-periods (e.g., noon to midnight, and midnight to noon), the basal rate supplied during the first sub-period throughout the tracking period may be averaged and the basal rate supplied during the second sub-period throughout the tracking period may be averaged to determine two basal rates for inclusion in the backup therapy protocol. The basal rate may be determined on an hourly rate or based on any other time period. Alternatively, the basal rate may be determined based on an amount of time that a particular quantity (e.g., one unit) of insulin is recommended to be administered to the subject 512 as part of the backup therapy protocol. For example, if the glucose level control system 510 determines that the subject 512 is receiving one unit of insulin every 1.125 hours, the backup therapy protocol may indicate the basal rate to be one unit every 1.125 hours. Alternatively, or in addition, the backup therapy protocol may indicate a basal rate of 0.89 units per hour.

In addition, generating the backup therapy protocol may include determining an average correction bolus provided to the subject per day over the tracking period. The average correction bolus may be determined by adding the total amount of correction doses administered each data and dividing by the number of days in the tracking period. The average correction bolus may be included in the backup therapy protocol as guidance for the user. However, generally, the correction bolus is supplied in response to a determination that a subject's blood glucose level is spiking or exceeding a threshold, and not necessarily as a daily dose of insulin. Accordingly, the average correction bolus may be included as part of the backup therapy protocol to facilitate the user understanding an amount of insulin that is likely to be required during an average day, which may be useful for the user (e.g., the subject) to determine how much insulin to have accessible to use, for example, in injection therapy. In some cases, one or more days, or time periods, of the tracking period may be omitted when determining the average correction bolus because, for example, the one or more days or time periods may be determined to be outliers. The outliers may be omitted to provide a more accurate understanding of average insulin needs or consumption.

In some implementations, the glucose level control system 510 may determine an average change in blood glucose at least partially attributable to a unit of insulin provided as a correction bolus to the subject during the tracking period. In some cases, the glucose level control system 510 may correlate each correction bolus applied during the tracking period to a change in the blood glucose level of the subject 512.

Generating the backup therapy protocol may include determining, for each mealtime of a plurality of mealtimes per day, an average mealtime bolus of insulin provided to the subject over the tracking period. In some cases, the average mealtime bolus may be determined for particular meals (e.g., breakfast, lunch, and dinner), while other periods of food intake (e.g., snacks or teatime) may be omitted or ignored. Further, the average mealtime boluses may be associated with particular meal sizes as identified by a user. For example, the glucose level control system 510 may determine an average mealtime bolus for a small and a large meal, or for a small, a medium, and a large meal. The average mealtime bolus may be determined by averaging an amount of insulin the glucose level control system 510 determines should be administered to the subject 512 using a control algorithm of the glucose level control system 510 for each mealtime and identified meal size.

In some cases, the backup therapy protocol may include data relating to the administering of counter-regulatory agent. For example, the backup therapy protocol may include an indication of total counter-regulatory agent and/or daily counter-regulatory agent provided to the subject over the tracking period.

At block 810, the glucose level control system 510 outputs the backup therapy protocol. Outputting the backup therapy protocol may include displaying the backup therapy protocol on a display enabling a user to implement the backup therapy protocol. Alternatively, or in addition, outputting the backup therapy protocol may include transmitting the backup therapy protocol to a computing device of a user for display and/or storage. In some cases, the backup therapy protocol may be stored at the glucose level control system 510 and may be accessed in response to a user interaction with a user interface of the glucose level control system 510.

In some cases, the process 800 can be combined at least in part with the process 900 described below. Thus, in some cases, the backup therapy protocol may further include a record of user modifications to one or more control parameters used by the control algorithm of the glucose level control system 510 to autonomously determine doses of insulin to be infused into or administered to the subject. This record of user modifications may include an identity of instances of user modification to the control parameter and/or a percentage of times a user modified the control parameter during each day of the tracking period and/or during the entire tracking period.

Figure 9:
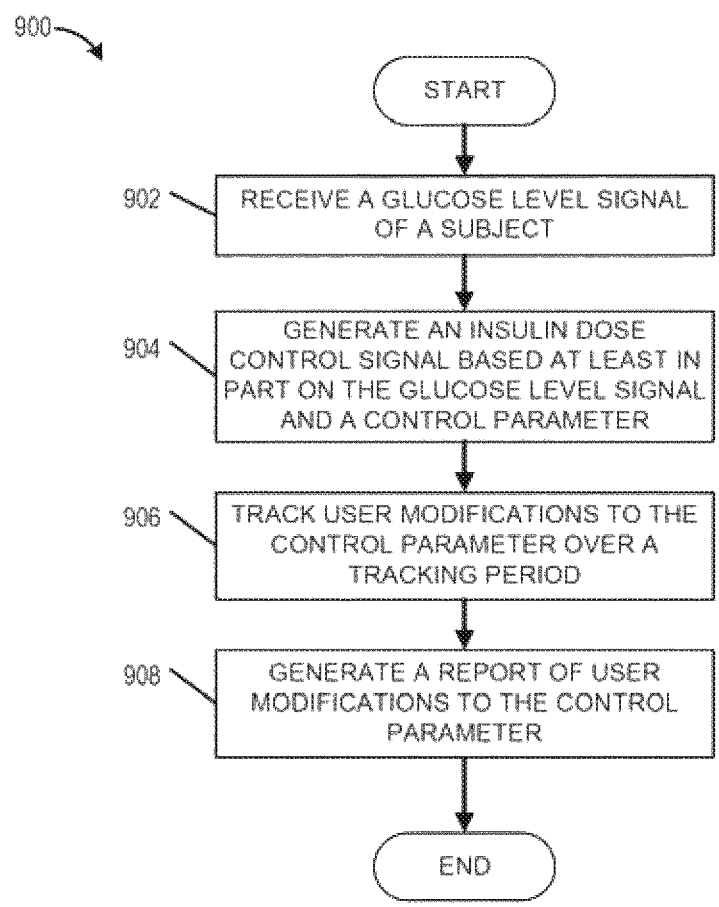
FIG. 9 presents a flowchart of an example control parameter modification tracking process in accordance with certain embodiments.

FIG. 9 presents a flowchart of an example control parameter modification tracking process 900 in accordance with certain embodiments. The process 900 may be performed by any system that can track user interactivity with glucose level control system 510, and more specifically, occurrences of a user modifying a control parameter used by the glucose level control system 510 to help control medicament delivery to the subject 512. For example, the process 900 may be performed by one or more elements of the glucose level control system 510. In some cases, at least certain operations of the process 900 may be performed by a separate computing system that receives indications of changes to control parameter settings of the glucose level control system 510 from the glucose level control system 510 and/or from user interaction with a user interface at the separate computing system prior to transmitting the modification to the glucose level control system 510. Although one or more different systems may perform one or more operations of the process 900, to simplify discussions and not to limit the present disclosure, the process 900 is described with respect to particular systems.

The process 900 begins at block 902 where the glucose level control system 510 receives a glucose level of a subject 512. The block 902 can include one or more of the embodiments previously described with respect to the block 802.

At block 904, the glucose level control system 510 generates an insulin dose control signal based at least in part on the glucose level signal and a control parameter. The insulin dose control signal may be generated based on a control algorithm that enables the glucose level control system 510 to autonomously determine doses of insulin to be infused into or administered to the subject to control the blood glucose level of the subject. The control algorithm may determine the doses of insulin based at least in part on the control parameter. The control parameter may include any parameter that can affect the operation or output of the control algorithm, or the operation of the glucose level control system 510, and that is modifiable by a user (e.g., the subject 512 or a user that is at least partially responsible for care of the subject 512 (e.g., a parent or guardian)). In some cases, the control parameter may be, or may correspond to, a target setpoint for the glucose level of the subject 512. In other cases, the control parameter may correspond to whether the glucose level control system 510 is to generate the insulin dose control signal for at least a period of time. For example, the control parameter may relate to whether at least some operation of the glucose level control system 510 is paused or active. The block 904 can include one or more of the embodiments previously described with respect to the block 804.

At block 906, the glucose level control system 510 tracks one or more user modifications to the control parameter over a tracking period. The tracking period may be one day, less than a day, or it may be longer than one day (e.g., 2 days, 3 days, a week, a month, etc.). Further, the tracking period may include one or more periods of time as previously described with respect to the process 800. The user may be the subject 512 or any other user (e.g., a parent or guardian, or a healthcare provider) that may be permitted to modify a control parameter of the glucose level control system 510.

The user may modify the control parameter using a user interface that may be generated and/or output by the glucose level control system 510. Alternatively, or in addition, the user interface may be generated and/or output by a computing system that can communicate with and/or modify the control parameter at the glucose level control system 510. For example, the computing system may be a smartphone, a smartwatch, a laptop, or desktop computer, or any other type of computing device that may be used to configure the glucose level control system 510. The user interface may be output on a touchscreen with which the user may interface to modify the control parameter. The user may interact with a control parameter selection element or other user interface element to select and/or modify the control parameter. In some cases, the user may provide the control parameter with any value supported by the glucose level control system 510. In other cases, the user may be limited to selecting particular values for the control parameter, which may be less than the supported capability of the glucose level control system 510 or less than what other users are permitted to select. For example, a clinician may be granted a greater modification range than a parent for modifying the control parameter.

Tracking the one or more user modifications may include storing in the one or more user modifications in a therapy log, database, or other data structure. Further, tracking the one or more user modifications may include tracking or storing whether each of the user modifications comprises an increase or a decrease in the control parameter. The determination of whether the control parameter has been increased or decreased may be determined based on whether a value for the control parameter has been increased or decreased relative to a reference value. The reference value may include a current value of the control parameter, a default value, a clinical value supplied to the glucose level control system 510, and/or a value determined by the glucose level control system 510. Further, tracking the one or more user modifications may include storing a time and/or one or more conditions under which the control parameter is modified. For example, the glucose level control system 510 may store a time of day, an activity level of the subject 512 as determined from one or more physiological sensors and/or as identified by a user, a meal being consumed or not consumed, and the like. Moreover, tracking the insulin therapy may include storing an indication of the autonomously determined doses of insulin delivered or administered to the subject 512.

In some cases, the tracking period may be divided into a plurality of sub-periods. The sub-periods may correspond to different portions of a day within the tracking period. For example, each day of the tracking period may be divided into two equal halves corresponding roughly to day and night, or into 3 or 4 different periods corresponding to a particular number of hours in the day. The sub-periods may be of equal or unequal length. Tracking the one or more user modifications may include tracking the occurrence of modifications to the control parameter within the sub-periods of the tracking period. Further, the occurrence of modifications within a sub-period of a day within the tracking period may be combined with the occurrence of modifications within a corresponding sub-period of another day within the tracking period. In other words, each occurrence of a modification of a control parameter in a sub-period defined from 9:00-21:00 may be aggregated across days of the tracking period.

In some cases, a different reference value may be determined for each control parameter for each sub-period. In some such cases, tracking the one or more user modifications may include tracking modifications to the control parameter value with respect to the reference value for the sub-period.

At block 908, the glucose level control system 510 generates a report of user modifications to the control parameter. Alternatively, or in addition, the repot may be generated by another computing system, such as a cloud computing system or a computing system of a healthcare provider based on data (e.g., occurrences of user modification of the control parameter value) received from the glucose level control system 510.

The report may include a measure of frequency of increases and decreases from the stored control parameter value. Further, the report may indicate a number of times that operation of one or more features of the glucose level control system 510 has been paused or suspended, or a percentage of the tracking period that operation of one or more features of the glucose level control system 510 has been paused or suspended. Moreover, the report may indicate a magnitude of the modification to each control parameter for each occurrence, in total, and/or on average. In some cases, the report may indicate a percentage of user modifications that are higher or lower than the reference value over the tracking period. Further, cases where the tracking period, or each day of the tracking period, is divided into a sub-period, the report may include a measure of frequency of increases and decreases from a reference value for the control parameter for each sub-period of the tracking period. In some cases, the report may include an identity of user activity that occurred when, or within a threshold time period, of a user modification to a value of the control parameter. For example, the report may identify whether a user was exercising (e.g., swimming, running, dancing, etc.) when a user modification to the control parameter value was made.

In some embodiments, the block 908 may include storing the generated report at the glucose level control system 510 (e.g., in the memory 540) and/or at a storage of another computing device. In some cases, the computing device may be a computing device of the subject 512 (or parent or guardian). Further, the computing device can be a computing device of a healthcare provider. In some cases, the computing device may be a computing device of a cloud computing service.

The report may be obtained from the glucose level control system 510 by a wired connection (e.g., a USB cable). Alternatively, or in addition, the report may be obtained via a wireless connection to the glucose level control system 510. For example, the glucose level control system 510 may establish an encrypted connection to a computing system of a healthcare provider, which may receive the report from the glucose level control system 510. Alternatively, or in addition, the glucose level control system 510 may establish an encrypted communication channel with a cloud computing provider, which can receive the report from the glucose level control system 510. This report may then be accessed by any authorized users.

Advantageously, in certain embodiments, a healthcare provider can use the report to help manage care of the subject 512. For example, if the healthcare provider determines that a user is modifying the control parameter more than a threshold number of times or during particular time periods, the healthcare provider may use this information to modify the care being provided to the subject 512 and/or to educate the subject 512 on optimal care. For example, the rate of therapy may need to be modified or the amount of insulin may be too low for the subject's comfort. For example, in some cases, a subject 512 may have a different tolerance to a blood glucose level than the average user leading the user to modify a setpoint range. Understanding this information can help the healthcare provider manage care of the subject 512 (e.g., adjusting the initial setpoint range, or modifying a type of insulin prescribed).

Further, as indicated above, the process 900 may be combined with the process 800. In other words, a report may be generated that includes both backup therapy protocols and a record of the number of times a user may a modification to one or more control parameters of the glucose level control system 510. In other cases, the processes 800 and 900 may be triggered and/or performed independently.

Example Backup Therapy Reports

FIGS. 10-12 illustrate one non-limiting example of a backup therapy report, or a set of reports, that may be generated using one or more of the embodiments disclosed herein. In other words, the reports of FIGS. 10-12 may be portions of a single report generated by the glucose level control system 510, or may be separate reports that are concurrently generated or that are generated based on different data and/or over different tracking periods. The report may be generated by the automated blood glucose control system 510, or by another computing system that may receive therapy data from the automated blood glucose control system. Further, FIGS. 10-12 represent just one non-limiting example of a report or set of reports that may be generated. It is possible for other reports to be generated that include more or less data. For example, the backup injection therapy protocol and the backup pump therapy protocol illustrated in FIG. 10 may be separated into two separate reports that may be separately generated and/or accessed.

FIG. 10 illustrates an example backup therapy protocol report 1000 in accordance with certain embodiments. The amount of insulin recommended under different ties and/or conditions may be displayed in units. In some cases, the report 1000 may identify the quantity of insulin included in a unit and/or the type of insulin. Further, in some cases, the report 1000 may be an interactive report that enables a user to modify a type of insulin or a unit size of insulin. In some such cases, the table 1002 may update the recommended number of units of insulin to administer under particular times or conditions based on the type of insulin and or unit size of insulin selected.

The report 1000 may identify the length of the tracking period 1006 used to determine the backup therapy protocol. Further, the report 1000 may identify the time or date range 1008 during which the tracking period 1006 occurred. Advantageously, knowing the tracking period 1006 may help determine an amount of trust to place in the recommendations included in the backup therapy protocols. The longer the tracking period, the more likely that the recommendations are accurate. A shorter tracking period is more susceptible to less accurate recommendations because, for example, the tracking period may encompass more days that are outliers for the subject's typical condition or activity level. For example, a tracking period of one day that occurs on a day when a subject consumed larger than normal meals or exercised significantly more than normal may result in backup therapy recommendations that do not match the subject's typical lifestyle. Further, knowing when the tracking period occurred may be useful to determine how current the recommendations are and whether they are a reliable indicator of an amount of insulin a subject should administer. For example, if the date range 1008 of the tracking period 1006 is a year old, and the subject has gained or lost significant weight over the year, the backup therapy protocol may no longer be a reliable indication of recommended injection therapy. In such cases, a user may adjust the recommendation and/or trigger a new occurrence of the process 800.

The table 1002 illustrates an example backup injection therapy protocol, which may indicate various insulin doses that may be administered to the subject 512 at various times or under various conditions using injection therapy. The table 1002 identifies an amount of insulin the subject 512 may inject when consuming a usual-sized meal for breakfast, lunch, or dinner. The usual-sized meal may refer to the size of a meal that the particular subject 512 usually consumes or has been advised to consume by a healthcare provider. The units of insulin specified may refer to an amount of insulin that the automated blood glucose control system 510 provides the subject 512 on average when the user consumes the identified usual size meal. In some cases, the table 1002 may further include recommended insulin doses for different size meals. For example, each breakfast may illustrate three different values (e.g., 5 units, 6 units, and 8 units) corresponding to light or smaller than usual breakfast, usual size breakfast, and heavy or larger than usual size breakfast.

It should be understood that the amount of insulin delivered may vary over time and/or based on the condition of the patient at a particular time. Thus, as indicated at the top of the report 1000, the recommendations in the backup therapy protocols are suggested for temporary use for a particular quantity of time (e.g., up to 72 hours in the illustrated example). The quantity of time for which the recommendations are valid may vary based on the subject 512, the amount of historical data collected (e.g., the size of the tracking period), the amount of daily variation in the subject's blood glucose level, or any number of other factors that may affect the amount of time that the backup therapy protocol can be safely followed.

As illustrated by table 1002, the backup injection therapy protocol may further identify an amount of long-lasting insulin a subject 512 is recommended to administer each day (or at certain times throughout the day). This long-lasting insulin may be used in place of the basal insulin that the glucose level control system 510 may provide on a periodic basis.

In addition, the table 1002 identifies the reduction in glucose level attributable to one unit of insulin. For example, as illustrated in the table 1002, the automated blood glucose control system 510 has determined that one unit of insulin (e.g., $\frac{1}{100}^{th}$ of a milliliter of insulin) may reduce a subject's 512 blood glucose level by 9 mg/dL. Accordingly, a user implementing injection therapy may measure a subject's 512 blood glucose level, determine a difference between the measured blood glucose level and a desired setpoint or threshold glucose level, and divide the difference by 9 to determine a number of units of insulin to inject in response to a determination that a correction dose is warranted (e.g., that blood glucose is outside of a desired setpoint range).

The table 1004 of the report 1000 provides an example of a backup pump therapy protocol. As illustrated, the backup pump therapy protocol may have the same therapy information as the backup injection therapy protocol for meal times and for the correction factor. However, because a pump may be capable of providing periodic basal therapy, the long acting insulin units of the injection therapy may be replaced with a basal rate indicating a rate at which the backup or replacement pump should administer insulin to the subject. As illustrated, the basal rate may vary over time. In the illustrated example, a basal rate is supplied for four different time periods constituting a 24-hour day. However, the basal rate may be divided into a fewer (e.g., 2 twelve-hour blocks) or greater (e.g., every four hours) number of periods, with each time period potentially having a different basal rate as determined based on the historical therapy data provided by an automated blood glucose control system.

In some cases, the report 1000 may include additional data that may be tracked over the tracking period. This additional data may include any data that may facilitate care of the subject 512 and/or maintenance of the automated glucose level control system 510. Some non-limiting examples of additional data that may be tracked and included in a report using, for example, the process 800 or 900 are illustrated in chart 1010 of the report 1000. For example, as illustrated in the chart 1010, the report may include the average blood glucose level of the subject 512 over the tracking period and/or the corresponding estimated A1C percentage. Further, the report 1000 may indicate the amount or percentage of time that the subject's blood glucose level is within a desired setpoint range and/or is above the desired setpoint range. Similarly, the report 1000 may indicate the amount or percentage of time that the subject's blood glucose level is below a threshold blood glucose level.

In addition, the report 1000 may indicate the average number of meal announcements per day. As illustrated in the chart 1010, the subject 512 from which the example report 1000 was generated made an average of 4.2 meal announcements indicating that on average, the subject consumed more than 3 meals a day. In some cases, the report may further indicate the types of meals announced (e.g., two breakfasts, one lunch, and one dinner). The second breakfast may be a large snack that is roughly equivalent in size to a small breakfast for the subject. Thus, the subject may have made an additional breakfast meal announcement. In some cases, the automated glucose level control system 510 may support a separate snack or other meal announcement option.

The report 1000 may further include the total amount of insulin administered to the subject per day, and/or the total amount of counter-regulatory agent (e.g., glucagon) administered to the subject per day. In addition, the report 1000 may indicate the amount of percentage of time that the automated glucose level control system 510 is able to connect or communicate with the CGM sensor over the tracking period, which may correspond to the amount of time that the automated glucose level control system 510 functions in an online mode during the tracking period.

FIG. 11 illustrates an example control parameter modification report 1100 in accordance with certain embodiments. As previously stated, the report 1100 may be a separate report generated using, for example, the process 900. Or the report 1100 may be included as a second within the report 1000.

The report 1100 may generally provide an indication of the number or percentage of times that a user modified one or more control parameters of the automated glucose level control system 510 during a tracking period. Further, as with the report 1000, the report 1100 may identify the time or date range 1008 during which the tracking period 1006 occurred.

In some cases, a user may interact with the report 1100 to determine the number of percentage of times that the user modified one or more control parameters during a subset of the tracking period. Similarly, the user may filter or narrow the date range to view other data described herein for a subset (e.g., a selected data range) of the tracking period.

The report 1100 may include a graph 1102 that illustrates the subject's blood glucose level with respect to the desired target setpoint range over the course of a day during the tracking period. This day can be an average of the values obtained for each day over the tracking period, or it can illustrate a particular selected day.

Further, the report 1100 may include a table 1104 that indicates the percentage of times that a user modified the blood glucose target during specific time periods. In the table 1102 of the non-limiting example report 1100 indicates two time-periods, daytime and nighttime. However, it should be understood that the table 1104 may indicate fewer or more time periods. Further, the time periods may indicate specific times (e.g., from 9:00 to 21:00 and from 21:00 to 9:00) for the time periods.

As illustrated, the table 1104 may indicate the percentage of times that a user increased or decreased glucose target setpoints. In addition, the report may indicate the percentage of times that the user did not modify, or left as usual, the glucose target setpoint. This target setpoint indicated in the table 1104 may refer to a single target value (e.g., 110 mg/dL, 125 mg/dL, 130 mg/dL, etc.), or may refer to a target setpoint range (e.g., 70-180 mg/dL).

In addition, the report 1100 may indicate the number of times that a user set a temporary glucose target during the tracking period (the temporary target count 1106) or a selected data range. The report may also indicate a number of times that the user paused therapy during the tracking period (e.g., the paused insulin therapy count 1108) and/or the selected date range.

The blood glucose of a subject may be affected by a subject's weight. Accordingly, the subject may provide updates of weight to the automated blood glucose control system. In some such cases, the report may indicate a change in weight and when the weight parameter was modified (e.g., body weight data 1110). In some cases, the report 1100 may be filtered to show data before and after a weight change separately. The body weight data may be helpful for the healthcare provider to, for example, determine whether weight change may at least in part have been a basis for user modifications to target glucose levels. Generally, the automated glucose level control system 510 (e.g., using blood glucose readings) will automatically account for the effect weight changes may have on blood glucose control. However, the subject 512 may feel differently. The ability to collect the modification data relating to a user's modification of the automated glucose level control system 510 and to correlate the data with weight changes can assist a healthcare provider in better treating the subject 512 by, for example, adjusting settings of the automated glucose level control system 510, changing insulin prescriptions, educating the subject 512, or any other action that may improve care of the subject 512.

In some cases, the report may omit changes to blood glucose target settings that are below a threshold. In other words, minor changes that may be statistical noise may be ignored. Further, in some cases, the report may indicate when control parameters (e.g., at bedtime, with respect to a particular meal, such as dinner, etc.) are modified. In some cases, the report may also indicate the duration of the change to the glucose target setpoint, or other control parameter.

FIG. 12 illustrates an example meal selection report 1200 that may be included as part of some implementations of the control parameter modification report 1100 of FIG. 11 in accordance with certain embodiments. The report 1200 may include a table 1202 identifying the average number of times per day that a user (e.g., the subject 512) announces each meal type. Typically, a user will announce a meal 0 or 1 times a day. However, in some cases, a user may announce a particular mealtime more than 1 time to account, for example, for large snacks that may be similar in size to a particular meal. Smaller snacks often may be handled by the control algorithm of the automated glucose level control system 510 (e.g., by the corrective insulin controller 626) without a meal announcement.

Further, the table 1202 may identify the number of times over the tracking period, or selected time period within the tracking period, that meals of particular sizes are announced by a user. For example, the table 102 may indicate the number of times that a usual size meal is announced, a smaller than usual size meal is announce, or a larger than usual size meal is announced.

Automated Blood Glucose Control Refinement

An ambulatory medical device (AMD) may include a control system that autonomously provides therapy to a subject, for example, based on a health condition of a subject (e.g., determined based on one or more measured physiological indicators or parameters of the subject). In some examples, the control system may determine the therapy time and/or the intensity of the therapy during each therapy delivery based on one or more measured physiological parameters (e.g., using one or more subject sensors, such as a CGM sensor) and according to a predictive model that may include one or more control parameters. In some examples, the predictive model may be used to estimate a physiological effect of the therapy in order to adjust the therapy delivery according to an intended physiological effect. It is desirable to adaptively adjust the values of the control parameters to optimize the therapy delivery to a subject in the presence of time varying and subject specific factors that may influence the physiological effects of a therapy delivery on the subject. In some cases, the AMD may be an ambulatory medicament device that regulates the level of an analyte in subject's blood. An example of such ambulatory medicament device is an automated blood glucose control system (e.g., the glucose level control system 510) that may automatically provide insulin and/or a counter-regulatory agent (e.g., Glucagon) to a subject 512 to help control the blood glucose level (BGL) of the subject 512. Generally, a control algorithm may be implemented by the automated blood level glucose control system 510 to determine when to deliver insulin and/or how much insulin to provide to the subject 512. Further, the control algorithm may control both an ongoing or periodic delivery of insulin (e.g., a basal dose), and a correction bolus that may be provided to adjust a subject's blood glucose level to within a desired range. The control algorithm may use blood glucose level readings obtained from a subject sensor (e.g., a sensor measuring one or more physiological parameters of the subject in real time), such as a continuous glucose monitoring (CGM) sensor, that obtains automated blood glucose measurements from the subject. Moreover, in some cases, the control algorithm may deliver a bolus of insulin in response to an indication of a meal to be consumed or being consumed by the subject 512.

Insulin may be administered subcutaneously into blood of a subject 512. For example, the glucose control system may subcutaneously deliver a medicament (e.g., insulin, glucagon) via an infusion set connected to a site on subject's body.

There is often a delay, referred to as pharmacokinetic (PK) delay, between when the insulin is provided and when the amount of insulin in the subject's blood plasma reaches a particular concentration level, such as maximum concentration. This amount of time may vary based on the type of insulin and/or on the physiology of the particular subject. For example, with a fast-acting insulin, it may take approximately 65 minutes for a bolus of insulin to reach maximum concentration in the blood plasma of one subject, but 60, 64, or 70 minutes for another subject. For some other types of insulin, it may take anywhere from 3-5 hours to reach maximum concentration in the blood plasma of the subject. Additionally, there might be a delay, referred to as pharmacodynamic (PD) delay, between variation of the amount of insulin in the subject's blood plasma and the resulting variation of glucose level in the subject's blood. In some examples, the value of pharmacodynamic (PD) delay may be used to estimate BGL based on an estimated concentration of insulin in patient's blood.

In some cases, the blood glucose control system may implement a predictive algorithm based on a pharmacokinetic (PK) model to estimate the accumulation of insulin in the blood plasma of the subject over time, following the subcutaneous administration of insulin to a subject. In some examples, the PK delay may be subject specific and/or change overtime. Accordingly, in these examples, the PK model may include one or more parameters, referred to as control parameters, that may be subject specific and/or change overtime. Examples of factors and parameters that may influence the PK delay and/or the control parameters of the PK model may include, type of insulin, blood glucose level (e.g., at the insulin administration time), physiological characteristics of the subject, health condition of the subject, one or more physiological parameters of the subject, time of the administration, location at which the infusion set is placed, the amount of insulin administered and the like. The physiological characteristics may include characteristics shared among large portions of the population (e.g., weight, gender, age, etc.) as well as characteristics that may be unique or specific to the subject, or shared among few people (e.g., characteristics related to genetics). Differences between the physiologies of different subjects may result in differences in the optimal blood glucose range for each subject, or some subset of subjects. Further, the differences in physiologies may also affect the absorption of insulin into the blood plasma. In other words, different physiologies of different subjects may result in insulin absorption taking different amounts of time for different subjects. Thus, while the maximum concentration of glucose in blood plasma may occur 65 minutes after delivery of a bolus of fast-acting insulin for one subject, it may be 60 minutes or 70 minutes for another subject.

Accordingly, in some such examples, the blood glucose level control system 510 (e.g., the blood glucose control system of an AMD) may implement a method to adaptively change the one or more control parameters in of the PK model used in its control algorithm to modify its predictions, in order to maintain the BGL within a desired range. For example, the blood glucose control system may use readings from one or more subject sensors (e.g., a CGM) and/or information received from the subject (e.g., using a user interface of the AMD), to modify one or more control parameters.

As indicated above, a blood glucose system, such as an automated blood glucose level control system 510, may control delivery or administering of insulin, or a counter-regulatory agent, based on a PK model and one or more blood glucose level measurements of the subject. In some examples, the PK model can be a bi-exponential PK model that may be used to estimate or determine the absorption or accumulation of subcutaneously administered insulin into blood and/or a decay rate of the insulin level in the subject's blood for a given value of delivered dose of insulin. In some examples, the absorption of insulin over time according to a bi-exponential PK model may be represented by the following equation:

$$p(t) = KU_0(e^{-\alpha_1 t} - e^{-\alpha_2 t}) \qquad (2)$$

where $U_0$ is the subcutaneous dose in units (U), K is a scaling constant, and $\alpha_1$ and $\alpha_2$ are time constants that may be used as the control parameters of the model. In some examples, the peak time of absorption of insulin, starting from the time that subcutaneous dose ($U_0$) is administered, may be referred to as Tmax and can be determined based on the following equation:

$$\log\log\frac{\left(\frac{\alpha_2}{\alpha_1}\right)}{(\alpha_2 - \alpha_1)} \qquad (3)$$

In some examples, $\alpha_1$ and $\alpha_2$ can be related (e.g., through an equation such as $\alpha_2 = 1.5\,\alpha_1$ or any other linear or nonlinear mathematical relations). In some such examples, Tmax alone may be used as the control parameter of the bi-exponential PK model. In some cases, Tmax may be referred to the time at which the concentration of insulin in subject's blood reaches a maximum level (e.g., starting from the time that subcutaneous dose is administered). In some other examples, the bi-exponential PK model may be used to estimate or determine the accumulation of counter-regulatory agent or hormone (e.g., glucagon) in subject's blood. Equation 2 may be used to calculate the pending effect of the accumulated amount of insulin in the subcutaneously administered dose, as that can be taken to be the difference between the total area $$\left(\int_0^\infty p(t)dt,\right.$$

which can describe a measure of the total amount of hormone (e.g., insulin) that can be absorbed due to a dose $U_0$) and $$\int_0^t p(t)dt,$$

which can represent a measure of the expended portion of $U_0$ at time.

Often, the blood glucose control system is configured to maintain a subject's blood glucose within a particular range (e.g., a normal range). As blood glucose rises or falls, the blood glucose control system may administer particular amounts of insulin or counter-regulatory agent to the subject to bring the blood glucose level of the subject back to within a desired range or closer to a desired setpoint. As explained above, it may take some non-infinitesimal amount of time for the medicament to be absorbed into the subject's blood stream. Thus, a PK model (e.g., the bi-exponential PK model), may be used to determine how much insulin or counter-regulatory agent should be provided to the subject in order to maintain the subject's blood glucose within a particular range. In some examples, the PK model (e.g., the bi-exponential PK model) may be used to predict the concentration of insulin blood glucose level of the subject over time as insulin or counter-regulatory agent is administered. In some cases, the control parameter values of the PK model may be set by a healthcare provider based on default values obtained through clinical trials and/or based an individualized treatment plan for the subject as may be determined based on clinical tests of the subject and/or on the healthcare provider's evaluation of the subject, which may be determined based on tests of the subject.

However, as previously indicated, the pharmacokinetic delay and the control parameters of the PK model, may be subject specific and/or change overtime due to various factors. Thus, although clinical data may determine optimal or recommended values of the control parameters for an average subject through one or more trials, the determined data may not be optimal for a particular subject. Moreover, individualized treatment plans are typically based on point-in-time measurements. These point-in-time measurements may provide a good guideline for treatment, but the optimal values of the control parameters for a subject may vary at different times of day, due to different activities, due to changes in the subject over his or her lifetime, or for any other number of reasons.

The glucose level control system 510 of the present disclosure can implement a method or process to autonomously and/or automatically modify one or more control parameters of a control algorithm, or the model used by the control algorithm, to modify therapy provided to the subject using the glucose level control system 510. The method may be performed by a hardware processor 530 and/or a controller 518 that controls the administering of therapy. The system can provide therapy (e.g., insulin) to a subject in response to a determination of a blood glucose level of the subject. The blood glucose level may be determined based at least in part on a glucose level signal obtained from a glucose level sensor that is operatively connected to a subject. The determination of the therapy (e.g., an amount of insulin or counter-regulatory agent) may be based at least in part on the blood glucose level and/or the bi-exponential model. Moreover, the determination of therapy may be based at least in part on a value or setting of one or more control parameters of the blood glucose control system. The one or more control parameters may be, or may correspond to, one or more parameters of the bi-exponential PK model, or any other model or control algorithm used to control the administering of therapy to the subject.

As mentioned above, the system 510 may provide the therapy based on the value or setting of the one or more control parameters. The value or setting of the one or more control parameters may be based on an initial configuration of the blood glucose control system 510 by a healthcare provider, subject, or other user. Further, the initial configuration may be based on clinical data or data obtained that is specific to the subject. In some cases, a control parameter may be a time constant used by a control algorithm of the blood glucose control system (e.g., Tmax in a bi-exponential PK model). This time constant may be used in a calculation of an accumulation of insulin in the subject by the control algorithm. Further, the control parameter may be used to control an insulin dosing response of the control algorithm to a blood glucose excursion in the subject as indicated by a glucose level signal obtained from a glucose level sensor. In some cases, the control parameter may be, or may be related to, Tmax (e.g., defined by equation 2). For example, the control parameter may be an estimate of Tmax or a fraction (e.g., 0.5) of Tmax. As previously explained, Tmax may be the peak time of absorption of insulin, or the amount of time until the concentration of insulin from an insulin dose reaches maximum concentration in the blood of the subject.

Moreover, the control parameter may be associated with a setpoint or target blood glucose level, or a blood glucose range. For example, the control parameter could relate to a point in time when an estimated amount of "insulin on board" (e.g., an amount of insulin in the subject as determined by a model of insulin accumulation and/or utilization in the subject) falls below a threshold value. As another example, the control parameter can be a clearance time for insulin boluses (e.g., an estimate of an amount of time for an administered bolus of insulin to be utilized by the subject). In some cases, the control parameter may relate to $T\frac{1}{2}$, which corresponds to a time when the concentration of insulin in the blood plasma reaches half of the maximum concentration in the blood plasma. In some cases, the control parameter may be a parameter that can be used to calculate Tmax or $T\frac{1}{2}$.

In some examples, the system 510 may determine an effect of the supplied therapy (herein referred to as therapy effect or effect). For example, the therapy effect may be determined by analyzing a glycemic control of blood glucose (e.g., variation of BGL or supplied therapy over a measurement period) in the subject's blood as indicated by the glucose level signal received from the glucose sensor (e.g., a CGM sensor). In some cases, the control system may measure or determine the effect of the supplied therapy over time. In some such cases, the therapy effect may be determined based on variation of BGL and/or the amount of therapy delivered over time. Moreover, in some cases, the system may continue to supply therapy to the subject over several therapy delivery times or instances and may average or otherwise aggregate the measured or determined effects of the therapy over the several therapy delivery times or instances. In some other examples, the system 510 may determine the therapy effect based at least in part on an input received from the subject. The input received from the subject may include a subjective or objective effect. The input received from the subject may include manual blood glucose level measurements obtained using, for example, test strips. Another example of input may be an indication of light-headedness, difficulty breathing, headaches, or any other objective or subjective effect identified by the subject.

Based at least in part on the provided therapy and the measured or determined effects of the therapy (e.g., the changes in blood glucose level attributed to the therapy), the control system 510 may autonomously determine a modification to one or more control parameters. For example, the control system may modify Tmax value used by the control algorithm (or the PK model used in the control algorithm), for example, to improve the effect of a subsequent therapy that may be provided to the subject. As such, the directional modification (e.g., increase or decrease) of a control parameter value may depend on the measured or determined effect of the therapy provided based on the initial or prior value of a control parameter. Moreover, the directional modification of the control parameter value may depend on a difference between the determined or measured effect of the blood glucose therapy and an expected effect of the blood glucose therapy (e.g., calculated based on PK model). In some examples, the directional modification of a control parameter may be determined based on the amount of therapy doses provided and/or measured BGL of the subject, during and between one or more previous therapy deliveries.

In some examples, the pharmacodynamic delay for a subject may be a known value. In these examples, the amount of absorbed insulin in the subject's blood may be estimated based on the measured value of BGL received from a glucose sensor. In some such examples, the directional modification may depend on the difference between calculated value of absorbed insulin based on a PK model (e.g., bi-exponential PK model) with a selected value of Tmax, and the estimated value of the absorbed insulin based on the measured value of BGL received from a glucose sensor.

Using the modified control parameter, the system 510 may determine therapy to deliver to the subject 512 at a therapy delivery time. As with the initial control parameter, therapy may be delivered during one or more therapy delivery times based on the modified control parameter. The system may determine the effect of the therapy delivered based on the modified control parameter using one or more of the embodiments previously described with respect to the therapy delivered using the initial control parameter.

In some examples, the control system can compare the measured, determined or reported effects (e.g., physiological effects) from the therapy delivered using the initial value of a control parameter and those from the therapy delivered using the modified value of the control parameter. Based on the comparison, the control system may determine which values of the control parameter is preferable for the subject. In some examples, the comparison may be performed in real-time, or substantially in real-time. Further, the comparison may be performed by the system 510 without user interaction. The comparison may be performed using a comparison method and based on one or more comparison criteria.

The comparison method may be based on finite number of therapy effects determined or measured at discrete times or based on continuous temporal variations of an effect over a period. In some examples the comparison method may involve statistical analysis of the measured or determined effects resulting from usage of the initial value and modified value of the control parameter. The comparison criterion may be based on the effects or based on the temporal variations of the effects over a period. For example, the preferable control parameter value can be a value that causes the blood glucose level of the subject to stay within a desired range or closer to a setpoint level for the subject. Accordingly, the system can set or maintain the control parameter to have the value that generated blood glucose levels that are closer to the desired range or setpoint for the subject for subsequent therapy.

In some cases, the system 510 may repeat the process for different control parameter values enabling the system to refine the blood glucose control for the subject over time. In subsequent performances of the process, the initial control parameter value may not be an initial value but may be the most recent selected value for the control parameter based on the determined effects of the control parameter.

In some cases, the determination of a second or modified value for a control parameter, or the modification of the control parameter may be triggered based on a glucose level of the subject not satisfying a threshold. Alternatively, or in addition, a process of modifying a control parameter value may be triggered based on a difference between an expected glucose value of a subject and an expected glucose value of a subject after the administering of therapy exceeding a threshold.

Using the embodiments described herein, the value of a control parameter may be autonomously modified without interaction by a subject or user with the blood glucose control system. In other words, the blood glucose control system can automatically adjust and/or refine a control parameter used by a control algorithm for glycemic control of the subject.

As previously described, the blood glucose control system may provide both insulin therapy and counter-regulatory agent therapy to a subject. In some cases, the blood glucose control system may only provide insulin therapy. In some such cases, the blood glucose control system may output an indication of an amount of counter-regulatory agent that may or should be administered to the subject based on a detected condition of the subject.

The active control parameter value used by the control parameter may remain active until a subsequent occurrence of the therapy modification process. In some cases, performance of the therapy modification process is continuously performed with the control parameter value being modified based at least in part on a determined effect of the prior control parameter value. In other cases, the therapy modification process is performed until the determined effect of the therapy satisfies a desired threshold (e.g., when the detected blood glucose level is within a threshold of a setpoint or median setpoint value). In some cases, the therapy modification process is performed a set amount of times and the control parameter value that provides the best outcome (e.g., closes to desired blood glucose level) is set as the active control parameter for subsequent therapy. In some cases, providing therapy at different sites on the subject's body (e.g., back, stomach, leg, or arm) may result in different blood glucose absorption rates (associated with different PK delays). Thus, in some such cases, the therapy modification process may be performed each time the infusion set used to deliver the therapy is moved to a different site on the subject.

Example Automated Blood Glucose Control Refinement Process

Figure 13:
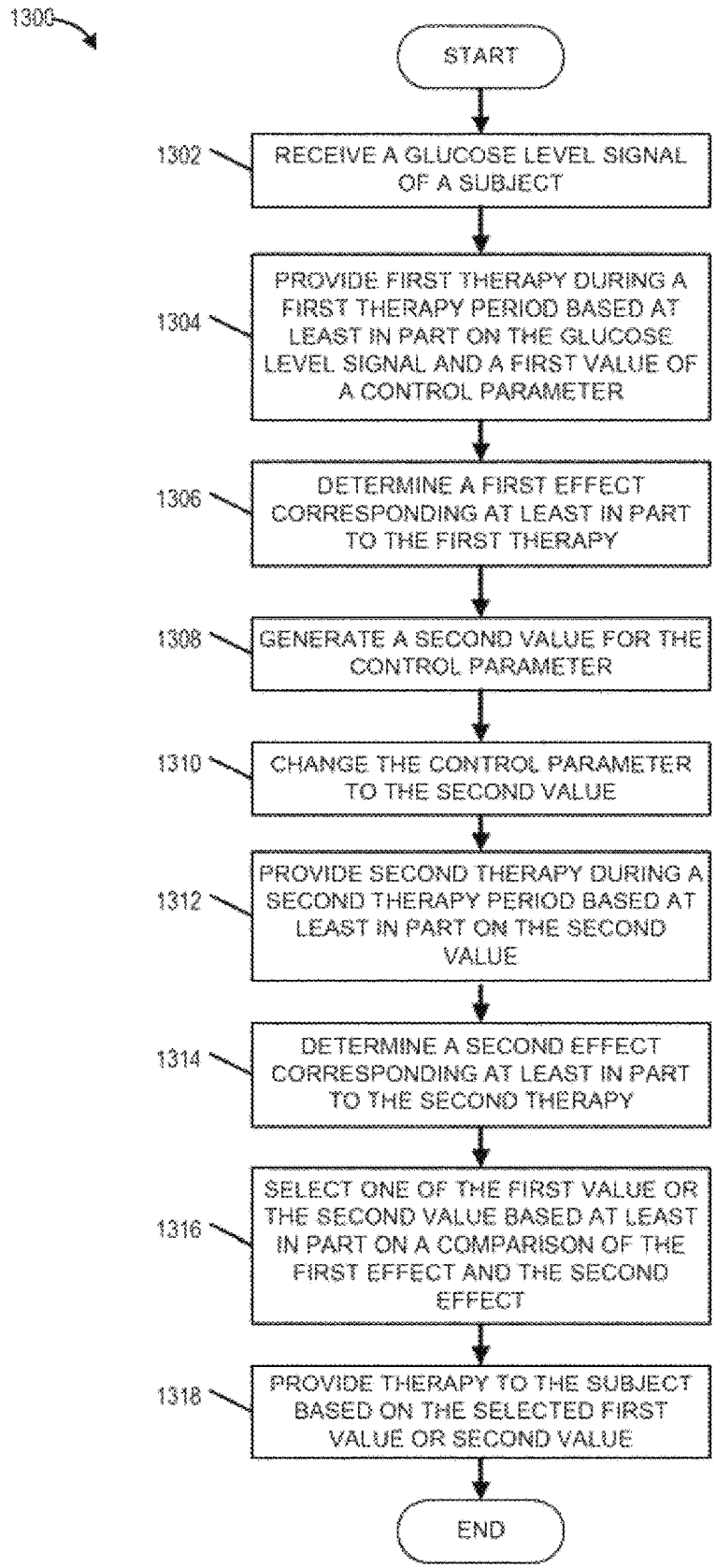
FIG. 13 presents a flowchart of an example automated blood glucose control refinement process in accordance with certain embodiments.

FIG. 13 presents a flowchart of an example automated blood glucose control refinement process in accordance with certain embodiments. The process 1300 may be performed by any system that can autonomously and/or automatically modify a control algorithm and/or a control parameter that affects execution of the control algorithm based on feedback (e.g., from a blood glucose signal) relating to therapy administered to a subject 512. For example, the process 1300 may be performed by one or more elements of the glucose level control system 510. In some cases, at least certain operations of the process 1300 may be performed by a separate computing system that receives blood glucose data from the glucose level control system 510. Although one or more different systems may perform one or more operations of the process 1300, to simplify discussions and not to limit the present disclosure, the process 1300 is described with respect to particular systems.

The process 1300 may be performed automatically and without user interaction. In some cases, a user may trigger the process 1300 via a command or interaction with a user interface. However, once the process 1300 is triggered, the process 1300 may be performed automatically. Further, the process 1300 may be performed continuously, periodically, or in response to a trigger. The trigger may be time based and/or based on a measurement of the glucose level of the subject. For example, the trigger may correspond to a determination that a glucose level of a subject differs by more than a threshold from a predicted glucose level that is predicted by a glucose level control algorithm based on the administering of medicament. Further, the trigger may be based on the activation or first time use of the glucose level control system 510 by the subject 512.

The process 1300 begins at block 1302 where the glucose level control system 510 receives a glucose level signal corresponding to the glucose level of a subject 512. The glucose level signal may be received from a glucose sensor capable of measuring the level of glucose in the blood of the subject. For example, the sensor may be a continuous glucose monitoring (CGM) sensor. The block 1302 can include one or more of the embodiments previously described with respect to the block 802 or 902.

At block 1304, the glucose level control system 510 provides a first therapy during a first therapy period to the subject 512. The first therapy may be based at least in part on the glucose level signal and a first value of a control parameter. The control parameter may include any control parameter that affects operation of the glucose level control system 510 and/or performance of a control algorithm of the glucose level control system 510. The control algorithm may include any control algorithm used to determine a dose of medicament (e.g., insulin) to administer to the subject 512. In other words, the controller 518 or the processor 530 may use the control algorithm to generate a dose control signal based at least in part on a value (e.g., the first value of the block 1304) of the control parameter to cause the delivery device 514 to administer a dose of insulin or other medicament.

In some cases, the control algorithm may be based on the PK model (equation 2). Further, in some cases, the control parameter may be Tmax, which may be calculated using equation 3. In other cases, the control parameter may be T½, which may relate to the amount of time for the dose of insulin in the blood stream to drop to ½ of the maximum concentration in the blood attributable to the dose administered to the subject 512. In some cases, the control parameter corresponds to a time until insulin within blood plasma of the subject reaches a particular concentration level subsequent to administration of an insulin dose. Moreover, in some cases, the control parameter may be a parameter that affects the determination of Tmax, such as one or more of the time constants α1 and α2. In some implementations, the control parameter may be used by the control algorithm to account for and/or determine an accumulation of insulin (or other medicament) in the subject 512 and/or a rate of diminishment of the insulin (or other medicament) in the subject 512. In some cases, the control parameter may be used to control an insulin dosing response of the control algorithm to a blood glucose excursion in the subject as indicated by the glucose level signal received at the block 1302.

In some instances, the control parameter may relate to at least one time constant used in a calculation of an accumulation of insulin in the subject by the control algorithm, such as one or more of the time constants $\alpha_1$ and $\alpha_2$ that may be used in the calculation of Tmax. In some cases, the control parameter may correspond to a rate of insulin diminishment in the subject 512. In some cases, the control parameter may relate to a target setpoint or a target setpoint range for maintaining or attempting to maintain the subject's 512 blood glucose level.

The first therapy may correspond to a single administering of insulin to the subject 512. This single administering of insulin may be any type of insulin administered for any reason. For example, the insulin dose may be a basal insulin dose, a priming dose, a dose supplied in response to a meal announcement, or a correction dose of insulin. Moreover, the first therapy may be medicament other than insulin, such as counter-regulatory agent (e.g., glucagon). In some cases, the first therapy may be a plurality of medicament (e.g., insulin and/or counter-regulatory agent) doses supplied or administered to the subject 512 over the first therapy period. Further, the plurality of medicament doses may include a variety of types of medicament doses, such as one or more basal doses, one or more meal doses associated with one or more meal announcements, one or more corrective doses, etc.

The first therapy period may be a time period that corresponds to a single medicament dose. Alternatively, the first therapy period may be a time period that encompasses a plurality of medicament doses. Further, the time first therapy period may be a time period associated with a defined length of time. Alternatively, or in addition, the first therapy period may be defined based on a number of medicament delivery periods. In other words, the time period may vary based on the amount of time it takes to deliver or administer a specified number of doses of medicament (of any type or of a particular type).

The first value may be selected based on a prior therapy or a prior performance of the process 1300. In some cases, the first value is selected based on a baseline value. The baseline value may be associated with clinical data, or it may be determined based on initial operation of the glucose level control system 510 for some period of time before performance of the process 1300. Alternatively, or in addition, the first value may be selected based on clinical data or a particular prescription for the subject 512. In some cases, the first value may be based on clinical data for average users or average users that share certain physiological data with the subject 512. In some cases, the first value is determined based on a healthcare provider's assessment of the subject 512. Further, the first value may be determined based on an infusion site (e.g., back, stomach, leg, etc.) for the glucose level control system 510. In some cases, the first value may be selected based on demographics or characteristics of the subject 512. For example, the first value may be based on the subject's 512 gender, weight, body mass, or age.

At block 1306, the glucose level control system 510 determines a first effect corresponding, or attributable, at least in part to the first therapy. Determining the first effect may include receiving a glucose level signal from the glucose level sensor operatively connected to the subject. This glucose level signal may be a subsequent or updated glucose reading that is more recent than the glucose level signal received at the block 1302. The glucose level signal received at the block 1302 may be used to determine therapy to administer to the subject 512 and the glucose level signal received at the block 1306 may be used to determine a result of the administered therapy. It should be understood that glucose level signals may be received continuously or periodically and can be used to both determine therapy to administer and to determine the effect of the administered therapy.

In some cases, determining the first effect may include analyzing glycemic control of blood glucose in the subject as indicated by the glucose level signal. Analyzing the glycemic control of the blood glucose in the subject may include tracking the blood glucose level of the subject 512 over time. Further, analyzing the glycemic control of the blood glucose in the subject may include comparing the blood glucose level of the subject 512 over time to a predicted blood glucose for the subject 512 over time as predicted based on the PK model used in the control algorithm using the selected value for the control parameter. As mentioned above, in some examples, the measured blood glucose level of the subject 512 over time may be used to calculate the accumulation and/or diminishment of the insulin level in subject's blood. In these examples, analyzing the glycemic control of the blood glucose in the subject may include determining whether, or to what degree, the calculated accumulation and/or diminishment of insulin (or other medicament) using the PK model (e.g., bi-exponential PK model) and the control parameter values used in the control algorithm matches the accumulation or diminishment of insulin (or other medicament) estimated based on the measured blood glucose level (e.g., obtained from the CGM sensor). In some cases, the first effect may, at least partially, be determined by analyzing one or more signals received from one or more subject sensors that measure one or more physiological parameters of the subject (e.g., heart rate, temperature and the like).

In yet other examples, the first effect may be determined based on an input received from the subject (e.g., using a user interface of the AMD). In some cases, the first effect may be determined based at least in part on an assessment or input provided by the subject 512 (e.g., using a user interface) with respect to the first value or the first effect. For example, if the subject 512 feels woozy, dizzy, lightheaded, nauseous, or otherwise uncomfortable during the first therapy period, the subject 512 may, via, for example, a touchscreen display of the AMD, indicate how the subject 512 is feeling.

At block 1308, the glucose level control system 510 obtains a second value for the control parameter. This second value may be autonomously determined. Further, in some cases, the second value may be automatically determined. In some cases, the second value is determined based at least in part on a user triggering the blood glucose control refinement process 1300. In some such cases the control system may determine the second value and present it to the user via a user interface 534 of the control system 510.

In some other examples, the second value may be obtained from a user interface 534 of the blood glucose control system 510 (e.g., in response to a user interaction with the user interface). In some examples, the second value may be obtained from a computing system that is connected to or otherwise in communication with the glucose control system. The communication connection may be a wired or wireless connection. Further, the wireless connection may be a direct connection (e.g., via Bluetooth or other near-field communication technologies) or a connection over a network (e.g., a local area network, a wide area network, a cellular network, etc.).

The second value may be an increase or decrease of the control parameter compared to the first value. The second value may be limited to a particular maximum change from the first value. Further, the second value may be selected based at least in part on the first effect. For example, if the first effect corresponding to the first value results in blood glucose being near an upper range of the setpoint range, the second value may be selected in an attempt to being the blood glucose level closer to the middle of the setpoint range. Further, the second value may be selected based at least in part on characteristics of the subject 512, such as age, weight, gender, or any other characteristics that may affect blood glucose management. In some examples, the second value may be selected based at least in part on the first effect determined based on an assessment provided by the subject 512, in an attempt to reduce the symptoms felt by the subject 512.

In some cases, the second value of the control parameter may be generated based at least in part on a baseline value of the control parameter and an output of a function defined based on glycemic control of the subject. In some examples, the glycemic control of the subject may include the measured value of the glucose level in subject's blood (e.g., provided by the CGM) and/or the amount of therapy (e.g., dose of insulin or counter-regulatory hormone) provided during the first therapy period. The baseline value of the control parameter may correspond to the first value used to provide therapy at the block 1304. This baseline value may be a last known optimal value for the subject prior to any changes to the subject (e.g., change in weight, insulin type, or metabolism changes, etc.). Alternatively, or in addition, the baseline value may be a value determined by a healthcare provider. In some cases, the second value of the control parameter is based at least in part on glycemic control indicated by the glucose level signal.

In some cases, the second value may be a modification to Tmax or $T_{1/2}$. It should be understood that Tmax and/or $T_{1/2}$ may, at least in part, be based on the physiology or biochemistry of the subject 512. Thus, the setting of either Tmax or $T_{1/2}$ for the setting of the first value and the second value may refer to setting a parameter of the control algorithm or the PK model used by the control algorithm, representative of or corresponding to Tmax and/or $T_{1/2}$. For example, the setting of the first value and the second value may include setting one or more control parameters that may be used to determined or estimate Tmax and/or $T_{1/2}$ for the subject 512. However, the set value may differ from the actual value of Tmax and/or $T_{1/2}$ for the subject 512. Further, as Tmax and/or $T_{1/2}$ may vary for different subjects, it is not always possible to explicitly set or determine Tmax and/or $T_{1/2}$ for a subject. Instead, Tmax and/or $T_{1/2}$ may be estimated or determined by comparing the effects and/or blood glucose levels determined for different control parameter values that correspond, at least in part, to Tmax and/or $T_{1/2}$. Using the process 1300, the control parameter may iteratively approach the actual Tmax and/or $T_{1/2}$ for the subject 512, or within a threshold of the actual Tmax and/or $T_{1/2}$ for the subject 512. Alternatively, using the process 1300, the control parameter (such as one or more of the time constants $\alpha_1$ and $\alpha_2$) may iteratively approach a value that corresponds to the actual Tmax and/or $T_{1/2}$ for the subject 512.

At block 1310, the glucose level control system 510 changes the control parameter to the second value. Changing the control parameter to the second value causes a change in the operation or execution of the control algorithm. This change in the execution of the control algorithm may result in a change in one or more factors associated with the provisioning of therapy to the subject 512. For example, the changing in the execution of the control algorithm may result in a change in an amount of medicament delivered, a timing of the delivery of the medicament, a rate at which a dose of medicament is delivered to the subject 512, a target setpoint or target range for the blood glucose of the subject, a threshold used in determining whether to deliver medicament (e.g., a threshold difference from the target setpoint), or any other factor that may affect therapy delivered to the subject 512.

At block 1312, the glucose level control system 510 provides second therapy during a second therapy period to the subject 512. The second therapy is based at least in part on the updated control parameter that is updated to the second value at the block 1310. As with the first therapy, the second therapy may refer to one or a plurality of medicament doses. Further, the second therapy period may refer to a specific amount of time, an amount of time to deliver a particular number of medicament doses, or a particular number of medicament doses. In some cases, the block 1312 may include one or more of the embodiments described with respect to the block 1304 but using the second value for the control parameter over the second therapy period. In some examples, the duration of the second therapy period may be equal to the duration of the first period. In some other examples, the number of therapies delivered during the second therapy period may be equal to the number of therapies delivered during the first second therapy period.

At block 1314, the glucose level control system 510 determines a second effect corresponding at least in part to the second therapy. The block 1314 may include one or more of the embodiments described with respect to the block 1306, but with respect to the second therapy.

At block 1316, the glucose level control system 510 selects one of the first value or the second value based at least in part on a comparison of the first effect and the second effect. The comparison of the first effect and the second effect may be performed autonomously without action by a user. The glucose level control system 510 may select the one of the first value or the second value to be a current or active value for the control parameter based on whether the first effect or the second effect results in improved care (e.g., closer to a desired setpoint for a greater period of time, or less volatility in blood glucose values, or any other factor that a healthcare provider may use to evaluate the success of diabetes management) for the subject 512. In some cases, the glucose level control system 510 selects a third value to the current or active value for the control parameter. The third value may be selected based on the comparison of the first effect and the second effect. For example, if it is determined that the first effect is preferable to the second effect, the third value may be selected based on a change to the first value in the opposite direction as the change made to the first value to obtain the second value. For instance, if in the prior example, where it is determined that the first effect is preferable to the second effect, the first value corresponded to a Tmax of 60 minutes, and the second value was selected to correspond to a Tmax of a longer time period (e.g., 65 or 70 minutes), the third value may be selected to correspond to a Tmax of a shorter time period (e.g., 50 or 55 minutes).

Comparing the first effect and the second effect may include determining whether the first value or the second value brought the subject's 512 glucose level closer to a target setpoint and/or maintained the subject's 512 glucose level within a target range for a longer period of time. In some cases, comparing the first effect and the second effect may include determining whether the first value or the second value resulted in a more stable blood glucose level for the subject 512 or less volatility in the blood glucose level of the subject 512. In some cases, comparing the first effect and the second effect may include determining whether the first value or the second value resulted in more and/or greater excursions of the subject's 512 blood glucose level from a target blood glucose range.

Comparison of the first effect and the second effect may be performed in real-time or substantially in real-time accounting for the processing speed of the hardware processor 530 or the glucose level control system 510. Thus, in some cases, the comparison of the first effect and the second effect may be performed upon determination of the second effect.

In some embodiments, the comparison of the first effect and the second effect may include a statistical comparison or statistical analysis of the first effect and the second effect. In some cases, the comparison of the first and second effects may include determining whether the second therapy produced a statistically significant improvement in therapy (e.g., glycemic control) compared to the first therapy. A statistically significant improvement may vary depending on the subject or the condition of the subject. The comparison can also include a determination of whether there was a statistically significant increase in risk factors (e.g., hypoglycemia) during the second therapy period compared to the first therapy period. In some embodiments, a statistically significant improvement may be an improvement determined based on a first statistical analysis of a set of data associated with the first effect and a second statistical analysis associated with the second set of data associated with the second effect. For examples, the first and second statistical analysis may include calculating the mean and variance of the blood glucose levels measured during the first and second therapy periods, respectively. In some examples, an improvement may be determined by comparing the mean value and the variance of the blood glucose levels measured during the first and second therapy periods. In some examples, an improvement may be determined by comparing the mean value and the variance of the blood glucose levels measured during the first and second therapy periods with one or more reference values. The reference values may be values provided by a health care provider or a user and may be stored in the memory 540 of the glucose level control system 510. In some examples, the first and second therapy period may be long enough to include a plurality of therapy deliveries (e.g., infusion of glucose and/or glucagon) during each period. In some embodiments, an improvement may be determined by comparing by other statistical quantities calculated at least in part based on the blood glucose levels measured during the first and second therapy periods. In some such embodiments the statistical quantities may be specific statistical quantities defined for comparing the effects of a therapy (e.g., medicament delivery for controlling the blood glucose level in a subject).

In some cases, the first and/or second may be output to user (e.g., the subject or a parent) via a user interface of the glucose control system and/or a computing system (e.g., a smartphone, laptop, personal computer, or the like). In some examples, the user may use the determined effect to adjust the value of a control parameter.

In some cases, the value that better manages the subject's 512 blood glucose may be output to a user (e.g., the subject or a parent). The user may then configure the glucose level control system 510 based on the selected control parameter value. Alternatively, or in addition, the glucose level control system 510 may automatically modify the value of the control parameter. In some cases, the user may be provided with an opportunity to confirm the modification. In other cases, the modification may occur automatically without confirmation. However, the modification may be presented to the user (e.g., the subject or a healthcare provider) and/or logged in a therapy log.

In some cases, the comparison is performed by another computing system that is in communication with the glucose level control system 510. For example, the glucose level control system 510 may transmit the glucose level signal, data determined from the glucose level signal, and/or the assessment received from the subject, indicative of the effect of the blood glucose control, to another computing system, such as a local computing system, a smartphone, or a cloud-based computing system. Further, the glucose level control system 510 may transmit data associated with the control parameters values and the administering of medicament to the subject 512 to the computing system. The computing system may determine the value of the control parameter that better manages the subject's 512 blood glucose level. The computing system may configure the glucose level control system 510 with the selected value. Alternatively, or in addition, the selected value may be output to a user who can configure the glucose level control system 510 with the selected value.

At block 1318, the glucose level control system 510 provides therapy to the subject 512 based on the selected value for the control parameter that is selected at the block 1316. The therapy provided at the block 1318 may be provided during a third therapy period that is at some point after the first and second therapy periods. Thus, during the first two time periods, the first and second values may be used, respectively, for the control parameter to determine the value that results in the better outcome or improved care for the subject 512. During subsequent time periods, the value that resulted in the better outcome for the subject 512 may be used to provide future care for the subject 512. Alternatively, a new value that is neither the first or second value may be used to provide subsequent care in an attempt to find a value for the control parameter that may provide a better or improved level of care (e.g., closer to a desired target glucose level for a longer period of time) for the subject 512.

In some examples, providing therapy to the subject, may include generating a dose control signal to a delivery devices 514 (e.g., infusion pump coupled by catheter to a subcutaneous space of the subject 512) that delivers an amount of a medicament (e.g., insulin or a counter-regulatory agent) to the subject wherein the amount may be determined by the dose signal.

Providing therapy to the subject 512 based on the selected value may include configuring the glucose level control system 510 to provide therapy to the subject 512 during a third therapy period based at least in part on the active control parameter value. In some cases, configuring the glucose level control system 510 to provide therapy to the subject 512 based at least in part on the active control parameter value may end the process 1300. In other cases, the process 1300 may be repeated. Repeating the process 1300 may include using the selected value (e.g., the first or second value from a prior iteration of the process 1300) as the first value when performing the operations associated with the block 1304. The second value generated at the block 1308 may be a new value not used during the prior iteration of the process 1300.

The process 1300 may be repeated until a difference between the first effect and the second effect is less than a threshold difference. Alternatively, or in addition, the process 1300 may be repeated a particular number of iterations, periodically, in response to a command, or in response to determining that the subject's 512 blood glucose does not satisfy a particular threshold for a particular amount of time.

In some examples, the process 1300 may be used to modify more than one control parameters of a glucose system (or a control algorithm used by the control system). In some such examples, the process 1300 may be used to adjust a first control parameter during a first modification period starting from block 1302 and ending at block 1318, and to adjust a second control parameter during a second modification period again starting from block 1302 and ending at block 1318. The second modification period may be immediately after the first modification period or delayed by a particular time. In some example, the control system may determine when a second control parameter should be modified following the modification of a first parameter. In some examples, the delay may be determined at least in part based on the measured glycemic control based on the glucose signal (e.g., received from a CGM sensor). In some other examples, the delay may be determined based on input received from a user. In some examples, the modification of the second control parameter may be at least partially determined based on the determined modification of the first control parameter.

In some examples, a third control parameter may be adjusted during a third time period after adjusting the first and the second control parameters. The adjustment of the third control parameter may immediately follow the adjustment of the second control parameter or may occur after a delay. The delay may be determined at least in part based on the glycemic control of the subject after the second control parameter is adjusted. In some examples, the glucose control system may be configured to sequentially adjust the first and second, or the first, second and third control parameters when the glycemic control of the subject satisfies one or more threshold conditions. In some examples, the duration of the time period during which a control parameter is adjusted may defer from that of the other parameters.

In some embodiments, a modified version of the process 1300 may be used to determine a value (e.g., an optimal value) of a control parameter. In some such examples, after determining the second effect at block 1314, the control system may skip block 1316 and block 1318, and instead obtain a third value for the control parameter. In some examples, this third value may be determined at least in part based on the determined second effect at block 1314. In some examples, this third value may be autonomously determined. Further, in some cases, the third value may be automatically determined. In some cases, the third value is determined based at least in part on a user triggering the blood glucose control refinement process 1300. In some such cases the control system may determine the third value and present it to the user via a user interface 534 of the control system 510. In some examples, the third value may be provided by a user via a user interface 534 of the control system 510. In some examples, after obtaining the third value, the system may provide therapy to the subject based on the third value. This modified version of process 1300 may be repeated several times. In some examples, this modified version may be repeated until a difference between the last two subsequent effects is less than a threshold difference. Alternatively, or in addition, the modified version of the process 1300 may be repeated a particular number of iterations, periodically, in response to a command, or in response to determining that the subject's 512 blood glucose does not satisfy a particular threshold for a particular amount of time.

As described, the process 1300 may be used to modify one or more control parameters that affect the delivery of insulin. However, the process 1300 is not limited as such and may be used to modify one or more control parameters that affect the delivery of other medicaments, such as counter-regulatory agent (e.g., glucagon, dextrose, etc.). In some cases, the process 1300 may be used to recommend a change in insulin and/or counter-regulatory agent delivery without modifying the delivery. This can be advantageous for generating recommendations regarding counter-regulatory agent in a single hormone glucose level control system 510 that does not support counter-regulatory agent, or that supports the use of counter-regulatory agent, but does not have the counter-regulatory agent available.

Moreover, in cases where the process 1300 is used to modify multiple control parameters, the at least two or more of the control parameters may be related to each other. For example, if the control parameters include the time constants α1 and α2, there may be a relationship between $\alpha_1$ and $\alpha_2$ such that modifying α1 may cause a modification to α2. For instance, $\alpha_2$ may equal 1.5 times $\alpha_1$ The value for the control parameter set as the active parameter (e.g., the first value or the second value) at the block 1316 may be used by the control algorithm to provide therapy to the subject 512 for a particular period of time or until the process 1300 is repeated. As previously explained, in some cases, the process 1300 is repeated periodically and/or in response to a trigger, such as a blood glucose value or an average blood glucose value over a time period, or an indicate of a site change for the connection of the glucose level control system 510 to the subject 512 (e.g., a change in the location of the infusion set used to provide the subcutaneous dose).

Hypothetical Example

As previously described, the peak time of absorption of insulin may be referred to as Tmax. Different types of insulin may result in different amounts of time until peak absorption into the subject's blood or for different subjects. For example, in one hypothetical example, the aggregate Tmax among subjects for the fast-acting insulin lispro and insulin aspart may be determined to be approximately 65 minutes, while the aggregate Tmax among subjects using ultra-fast-acting insulin, such as, for example, the insulin aspart injection marketed under the Fiasp brand, which has a formulation to decrease time to peak absorption, may be determined to be approximately 40 minutes. When using an automated blood glucose level control system (such as the glucose level control system 510) with a control parameter corresponding to Tmax set to 65 minutes, there may be no statistically significant improvement in the average glucose level or the frequency of hypoglycemia when using the ultra-fast-acting insulin compared to using the fast-acting insulin. In this comparison, Tmax is held constant while varying the type of insulin used.

When adjusting the value of the control parameter for the automated blood glucose level control system to use different Tmax settings, in a hypothetical example, mean glucose drops when Tmax is lowered when using the ultra-fast acting insulin. In this example, three cohorts of subjects employ control algorithms that use modified Tmax values when using a blood glucose control system with ultra-fast-acting insulin such as Fiasp. The first cohort uses a blood glucose level control system configured with a Tmax of 65 minutes for a first week of therapy and a lower Tmax (such as, for example, 50 minutes) for a subsequent week of therapy. The second cohort uses the blood glucose level control system configured with a Tmax of 65 minutes for the first week of therapy and an even lower Tmax (such as, for example, 40 minutes) for a subsequent week of therapy. The third cohort uses the blood glucose level control system configured with a Tmax of 65 minutes for the first week of therapy and a sharply lower Tmax (such as, for example, 30 minutes) for a subsequent week of therapy. Comparison of the change in Tmax within each cohort and across cohorts demonstrates that the mean glucose level drops when Tmax is lowered, and there is no statistically significant increase or decrease in hypoglycemia.

When Tmax is shorter than physiological insulin absorption peak time, there is an increased risk of hypoglycemia because the blood glucose level control system may stack or administer multiple doses of insulin within a time period. This may occur because the blood glucose level control system may incorrectly identify a lower blood glucose concentration as a maximum blood glucose level concentration when Tmax is set below the actual peak insulin absorption time.

By using the process 1300 to compare the effect of different Tmax settings, it is possible to optimize the Tmax setting for a subject and/or a particular type of insulin. In some examples the comparison may be based on one or more statistical methods. For example, using the glucose concentration data collected during a therapy period (e.g., using a CGM sensor), the control system may determine whether there is a statistically significant difference in mean glucose level during a later period using a different Tmax value compared to an earlier evaluation period. If the subsequent or newer value used for Tmax results in an improved effect, Tmax or a control parameter of the blood glucose level control system 510 corresponding to Tmax may be set to the newer value, where the change in the control parameter value may occur automatically upon determination of a statistically significant improvement or may occur after generating a notification of the potential improvement and receiving confirmation that the change in control parameter value should occur. After collecting glucose signals of the subject 512 for a period of time at a default or prior value for Tmax, the value for Tmax may be lowered by a significant amount from the initial Tmax. For example, the control algorithm may automatically change Tmax or an associated time constant to reflect a Tmax reduction of at least 10 minutes, at least 5 minutes, at least 2 minutes, no more than 15 minutes, no more than 20 minutes, no more than 30 minutes, or by a change within a range spanning between any two of the preceding values in this sentence, where the preceding values are included in the range. The system can perform a statistical analysis between the prior data set associated with the higher Tmax, and the current data set associated with the lower Tmax. If the controller of the blood glucose level control system determines that there is a significant or statistically significant improvement (e.g., more than a threshold improvement) in the mean glucose level for the subject with little or no increase in hypoglycemia events or risk events, the system can adopt or recommend the lower Tmax value as the preferred Tmax. This process can be repeated using additional reductions in Tmax. In some cases, each reduction in Tmax may be smaller than the previous reduction. Moreover, if it is determined that there is a not an improvement in the mean glucose level for the subject and/or if there is an increase in hypoglycemia or hypoglycemia risk events, the system may use the prior Tmax or may select a Tmax between the new Tmax and the prior Tmax. Thus, using the process 1300, the system can iteratively modify Tmax to find an optimal value for the subject and/or the selected insulin type.

Moreover, by performing real-time analysis and optimization of one or more control parameters, maintenance of the subject's diabetes can be improved faster and more accurately compared to delayed analysis that may occur during clinical testing. Clinical testing may be less accurate as physiological changes in the subject may not be captured in real time.

In some cases, the real-time process and statistical analysis described above can be used to analyze other types of biomedical data obtained by one or more subject sensors (e.g., measuring one or more physiological parameters). In some such cases, the additional biomedical data, such as data may be received from a smartwatch (e.g., blood pressure, heart rate), from a weight sensor, or any other type of biomedical sensor. By adapting the process 1300 to perform statistical analysis of the additional biomedical data, it is possible to perform a quantitatively objective analysis of biometric data, which can be used by a healthcare provider to care for a subject.

Further, the outcomes of the comparative analysis described above may be used to make additional recommendations to the subject. For example, if it is determined that the actual Tmax for a particular type of insulin is higher than expected for the subject, it may be recommended that the subject modify his or her diet in a particular manner while using that particular type of insulin.

Example Simulations

Embodiments of an automated glucose level control system 510 that can be adapted for use with embodiments of the present disclosure are described in International Publication No. WO 2015/116524, published on Aug. 6, 2015; U.S. Pat. No. 9,833,570, issued on Dec. 5, 2017; and U.S. Pat. No. 7,806,854, issued on Oct. 5, 2010, the disclosures of each of which are hereby incorporated by reference in their entirety for all purposes.

The automated glucose level control system 510 can autonomously administer insulin doses and account for online accumulation of insulin doses ("insulin on board") due to the finite rate of utilization of the insulin. The rate the insulin absorption, and in turn accumulation, of insulin doses may be modeled by a pharmacokinetic (PK) model (e.g., the bi-exponential PK model represented by equation 2 with preset values of time constants α1 and α2). Of significant clinical significance in relation to the PK model is the time it takes for an insulin dose (e.g., administered subcutaneously) to be absorbed in subject's blood. In some examples, the peak time for insulin absorption in blood is referred to as Tmax. In some other examples, Tmax may be the time at which the concentration of insulin reaches its maximum value following the delivery of a specific dose of insulin. In some such examples, Tmax may be measured from the time that insulin is provided to the subject (e.g., subcutaneously using an infusion set).

In some examples, setting the time constants in the PK model (e.g., $\alpha_1$ and $\alpha_2$ in equation 2) may be equivalent to setting Tmax that is inherently assumed by the model; conversely, setting Tmax may set the time constants of the PK model. Since the values of the time constants may be used to determine the online calculation of the accumulation of insulin by a control system, the value of the time constants may consequently control the control system's insulin dosing response to a given blood glucose level excursion. Thus, varying Tmax or time constants associated with Tmax controls the aggressiveness of the control system's insulin doses.

In certain embodiments, the control system implements a method to adapt the control system's PK model's Tmax (hence time constants) setting online. This method may be performed either by the control system periodically making online assessments and calculations that produce recommendations of modifications in Tmax or by the control system autonomously modulating Tmax online. In either case, the calculations may be based on the control system's performance over some time period. In some cases, adaptations to Tmax online, whether autonomously occurring or issued as recommendations can be based on the glucose-control performance by the control system over some time interval, including trends in glucose level, mean glucose level, or extent and/or duration of low glucose level (hypoglycemia) and/or high glucose level (hyperglycemia) occurrence. Alternatively, the calculation can be based on the usage of a counter-regulatory agent, the otherwise intended usage of a counter-regulatory agent had it been available (e.g., in insulin-only systems or in cases where the counter-regulatory agent or its delivery channel are temporarily unavailable). The method can impose upper and/or lower (static or dynamic) bounds for the range over which the Tmax can vary. The degree of adaptation in Tmax for a given situation can be different depending, for example, on the specific insulin being administered by the control system.

In certain embodiments, the described method may be applicable regardless of whether the continuous glucose monitor (which can provide the input glucose signal to the control system) is online or offline. For example, the method disclosed herein can be applied to system described in International Publication No. WO 2015/116524. Further, the described method can coexist with other aspects of the system being activated or not, such as, but not limited to, having a glucose target that is adapted automatically by the system, e.g., as in the system described in International Publication No. WO 2017/027459, published on Feb. 16, 2017, which is hereby incorporated by reference herein for all purposes.

As previously described, the absorption of subcutaneously administered insulin into blood may be governed by the bi-exponential PK model of equation 2. Setting the time constants in the PK model may set a measure of the pending effect of the accumulated amount of insulin in the subcutaneously administered dose, as that can be taken to be the difference between the total area ( $$\left( \int_0^\infty p(t)dt, \right.$$

which can describe a measure of the total action over time due to a dose U0) and $$\int_0^t p(t)dt,$$

which can represent a measure of the expended portion of U0. The peak time, Tmax, of the absorption of insulin doses into blood may be given by equation 3. Thus, setting Tmax may set the PK model time constants, which can directly govern the magnitude (e.g., aggressive or conservative) of the control system's online insulin dosing response to a given glucose profile. Although not limited as such, for simplicity, assume that $\alpha_1$ and $\alpha_2$ are related, e.g. $\alpha_2 = 1.5\, \alpha_1$.

Figure 14A:
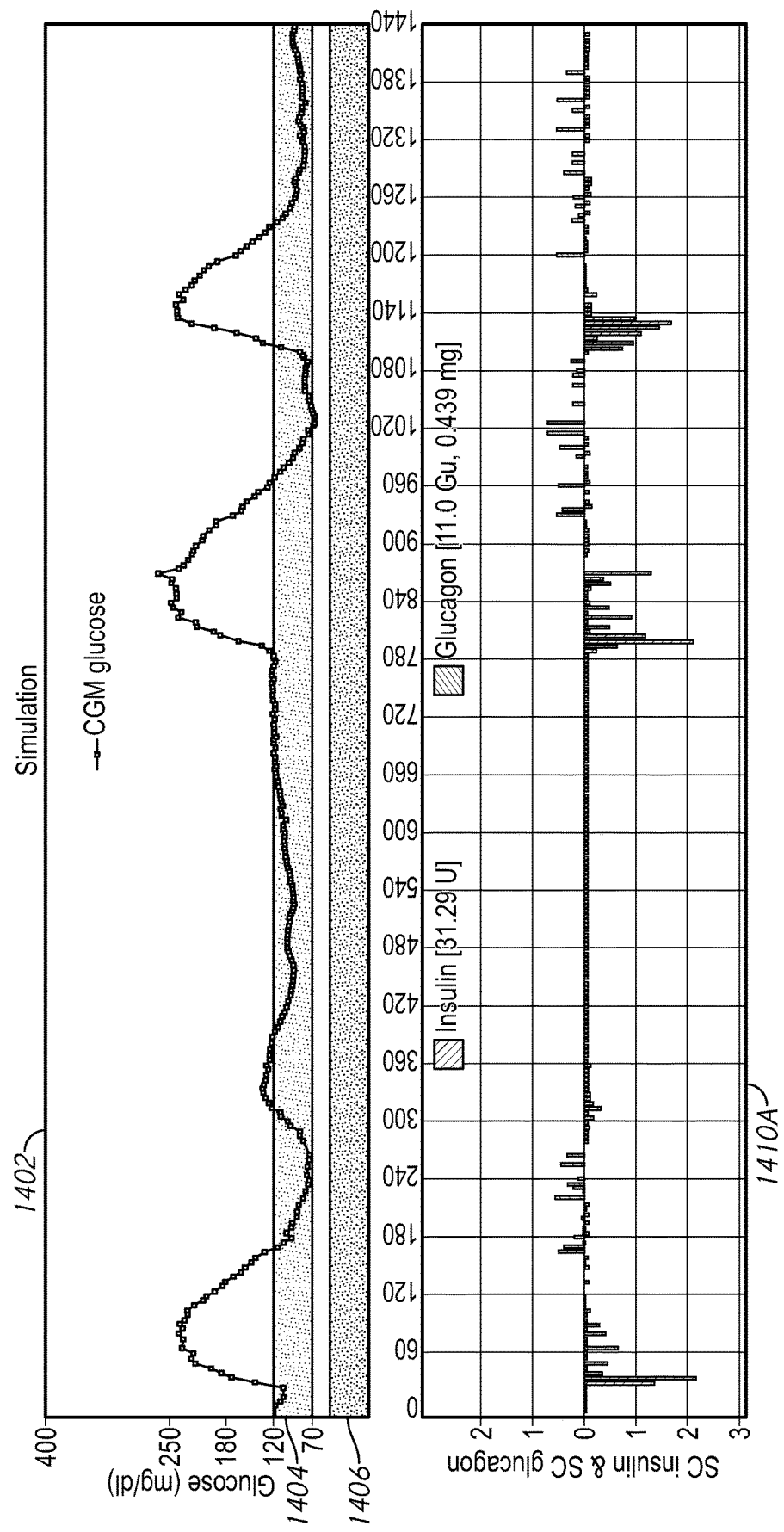
FIG. 14A illustrates a simulation of blood glucose control of a subject with Tmax set to 65 minutes.
Figure 14B:
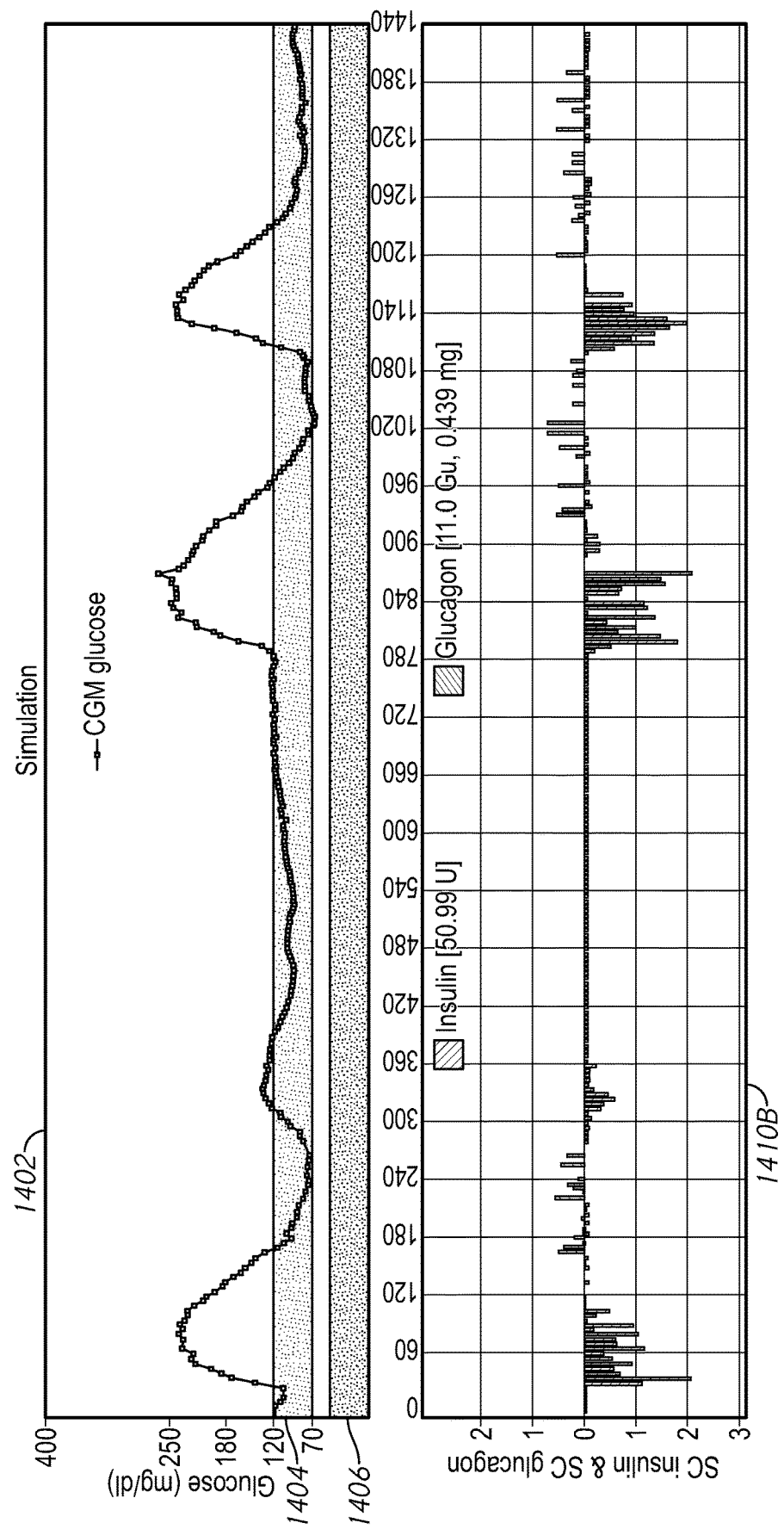
FIG. 14B illustrates a simulation of blood glucose control of a subject with Tmax set to 15 minutes.
Figure 14C:
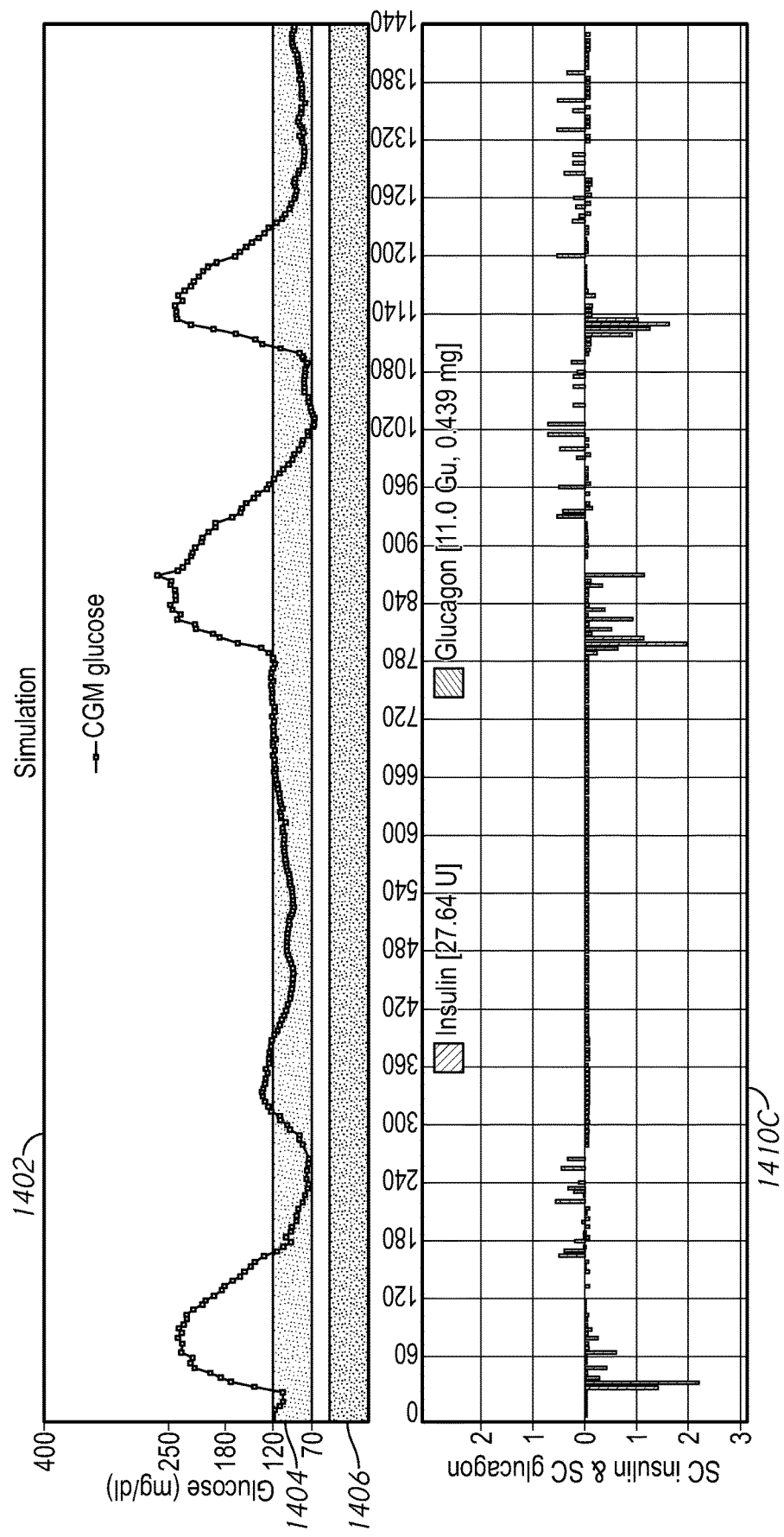
FIG. 14C illustrates a simulation of blood glucose control of a subject with Tmax set to 130 minutes.

The bi-exponential PK model may be used to simulate the relation between a glucose profile and the medicament (e.g., insulin or glucagon) doses delivered to a subject. FIGS. 14A-14C illustrate a simulation demonstrating an effect that increasing or decreasing the Tmax setting, or value for a control parameter corresponding to Tmax, may have on the glucose level control system's 510 online insulin and glucagon dosing response to a given glucose profile (e.g., temporal variation of blood glucose level over 24 hours).

FIG. 14A illustrates a simulation of blood glucose control of a subject with Tmax set to 65 minutes. The graph 1402 illustrates the variation of blood glucose level (BGL) of a subject over 24 hours. The range 1404 indicates the desired target setpoint range (e.g., between 70 and 120 mg/dL) for the subject's blood glucose level. Further, the range 1406 indicates the range in glucose level (e.g., below 60 mg/dL) for the subject that is associated with hypoglycemia or a risk of hypoglycemia. The graph 1410A illustrates the administering of medicament (insulin or glucagon) to the subject over the same 24-hour time period as graph 1402 based at least in part on the blood glucose level variation illustrated in the graph 1402.

FIG. 14B illustrates a simulation of blood glucose control of a subject with Tmax set to 15 minutes. The graph 1410B corresponds to the graph 1410A, but with Tmax set to 15 minutes instead of 65 minutes. As illustrated by comparing the graph 1410B to 1410A, reducing Tmax to 15 minutes may result in an increase in insulin dosing required to maintain the given glucose profile 1400.

FIG. 14C illustrates a simulation of blood glucose control of a subject with Tmax set to 130 minutes. The graph and 1410C corresponds to the graph 1410A, but with Tmax set to 130 minutes instead of 65 minutes. As illustrated by comparing the graph 1410C to 1410A, increasing Tmax to 130 minutes may result in a decrease in insulin dosing required to maintain the given glucose profile 1400.

Even if the glucose profile of a subject is unchanged, increasing or decreasing insulin (or counter-regulatory agent) dosing may affect care of the subject 512. For example, the subject may experience different degrees of symptoms (e.g., dizziness, nausea, etc.) attributable to maintenance of the subject's diabetes. Advantageously, autonomous optimization of one or more control parameters of a glucose control system, may reduce the amount and/or frequency of the medicament doses required to maintain a normal glucose profile.

The simulations illustrated in FIGS. 14A-14C illustrate one non-limiting example of the impact of modifying a control parameter of a glucose control system. In some cases, different dosing may subsequently lead to different blood glucose excursions which in turn may vary the determined insulin-glucagon doses subsequently. Nonetheless, the simulations shown in FIGS. 14A-14C, demonstrate the correlation between Tmax as a control parameter and the determined medicament doses by the glucose level control system 510 for each therapy. Further these simulations demonstrate that the determined therapy doses may be used as a feedback to adjust Tmax as descried below.

Example Automated Blood Glucose Control Refinement Process

In some implementations, the value of Tmax can be varied automatically online based on glycemic control in a receding time period. For example, Tmax can be described using the following the equation:

$$T_{max}(k) = T_{max}^{\circ} + f(y_k, g_k), \quad (4)$$

where $T_{max}^{\circ}$ is a baseline value of Tmax, $f(y_k, g_k)$ is a parameter control adjustment function (herein referred to as adjustment function), based on glycemic control of the glucose signal, $y_k$, and/or the amount of counter-regulatory dosing, $g_k$, that is computed by the control system (whether delivered or not). Evaluation off $(y_k, g_k)$ could be over a time period (e.g., one week, two weeks, four weeks or other time intervals). For example, $$f(y_k, g_k) = \sum_{k-N}^{k} f(y_n, g_n).$$

In some examples, k may represent a current therapy period and N may indicate a receding time period that may include one or more therapy periods.

The parameter control adjustment function $f(y_k, g_k)$ can cause an increase in $T_{max}(k)$ relative to $T_{max}^{\circ}$ for an increase in hypoglycemia (in severity and/or duration) or impending hypoglycemia in glycemic control of the glucose signal, $y_k$, over the receding time period (that may include one or more therapy periods) and, conversely, can cause a decrease in $T_{max}(k)$ relative to $T_{max}^{\circ}$ for an increase in hyperglycemia (in severity and/or duration) in glycemic control of the glucose signal, $y_k$, over the receding time period. Moreover, $f(y_k, g_k)$ can cause an increase or decrease in $T_{max}(k)$ relative to $T_{max}^{\circ}$ respectively for an increase or decrease in amount of counter-regulatory dosing, $g_k$, over the receding time period. The adjustment $f(y_k, g_k)$ to $T_{max}(k)$ can be evaluated and effected at discrete times, which can be at scheduled periodic intervals (e.g., once every 24 hours, once every three days, once a week, etc.), in response to a user command, or based on a physiological measurement of the subject. Alternatively, or in addition, adjustments can be evaluated and effected online when some metric satisfies a threshold or meets certain criteria within the current computation window (e.g., a week, a month, etc.). This criterion can include when hypoglycemia in $y_k$ reaches or crosses a certain threshold or the level of counter-regulatory dosing in $g_k$ reaches or crosses a certain threshold. Alternatively, or in addition, the adjustment can be effected after some evaluation related to the glucose signal $y_k$ (e.g., mean value) in the current computation window has attained a statistically significant difference from its evaluation in a preceding computation window (e.g., the week before). These described implementations allow for having dynamic instances that are mathematically determined online as to when $T_{max}(k)$ gets adjusted and/or the magnitude by which it is adjusted.

In some examples, therapy periods can be scheduled regular or periodic time intervals (e.g., 24 hour periods, two day periods, one week periods, etc.), based on a user command, or based on a physiological measurement of the subject. In some other examples, therapy periods may be defined as the time interval between two subsequent therapy deliveries, and each therapy period may be identified based on the therapy delivery time that marks the beginning of the therapy period. In either case, $f(y_k, g_k)$ may be the adjustment to $T_{max}$ for the $k^{th}$ therapy period and $f(y_k, g_k)$ may be evaluated based on the $$f(y_k, g_k) = \sum_{k-N}^{k} f(y_n, g_n)$$

wherein $y_n$ is the glucose signal measured during the $n^{th}$ therapy period, $g_n$ is the computed dose of a counter-regulatory hormone for the $n^{th}$ therapy period and N indicates the receding time period that may include one or more therapy periods. In some examples, N may be the number of the therapy periods receding the $k^{th}$ therapy period.

Figure 15:
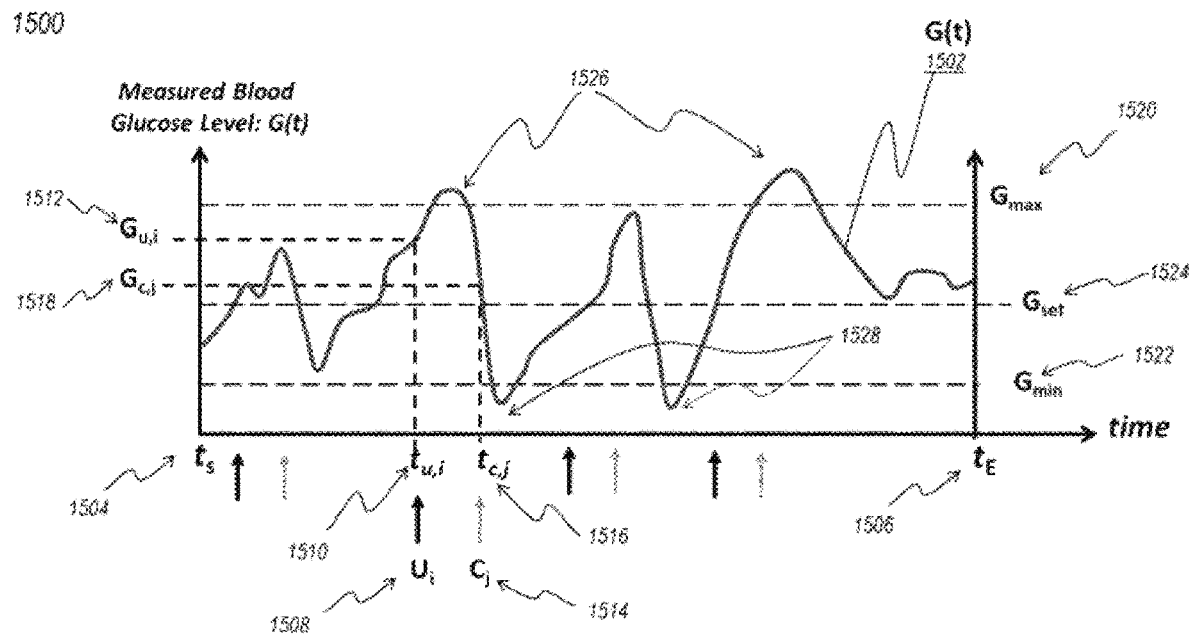
FIG. 15 illustrates an example of blood glucose level signal (CGM trace) and some of the parameters associated with glycemic control using a blood glucose control system.

FIG. 15 illustrates an example of blood glucose level signal G(t) 1502 (e.g., a CGM trace received from a CGM sensor) over a therapy period (starting from $t_S$ 1504 and ending at $t_E$ 1506) during which one or several doses of insulin and/or a counter-regulatory agent (e.g., glucagon) are determined and/or administered by the glucose control system 510. For example, an insulin dose of $U_i$ 1508 units may be provided at time $t_{u,i}$ 1510 at a measured glucose level of $G_{u,i}$ 1512 (where i varies from 1 to the number of insulin deliveries between $t_S$ 1504 and at $t_E$ 1506). Similarly the control system may have calculated a dose of $C_j$ 1514 units, that may have been administered or not, a glucose level $G_{c,j}$ 1518 at which glucagon may have been delivered and the time $t_{c,j}$ 1516, at which glucagon may have been delivered, (where j varies from 1 to the number of glucagon deliveries between $t_S$ 1504 and at $t_E$ 1506). The control system may be configured to provide therapy in order to maintain the BGL within a normal range defined by an upper bound $G_{max}$ 1520 and a lower bound $G_{min}$ 1522 and close to a setpoint $G_{set}$ 1524. In some examples, the glucose levels above $G_{max}$ 1520 may indicate hyperglycemia and glucose levels below $G_{min}$ 1522 may be considered hypoglycemia. For example, during the therapy period shown in FIG. 15, two instances of hyperglycemia 1526 and two instances of hypoglycemia 1528 may be identified by the control system. In some examples, during each therapy period the control system may store G(t) 1502, $t_{u,i}$ 1510, $t_{c,j}$ 1516, $U_i$ 1508 and $C_j$ 1514, for all therapy deliveries (all values of i and j). In some examples, the value of one or more control parameters (e.g., Tmax, $G_{set}$) may not change during the therapy period between $t_S$ 1504 and $t_E$ 1506.

Figure 16:
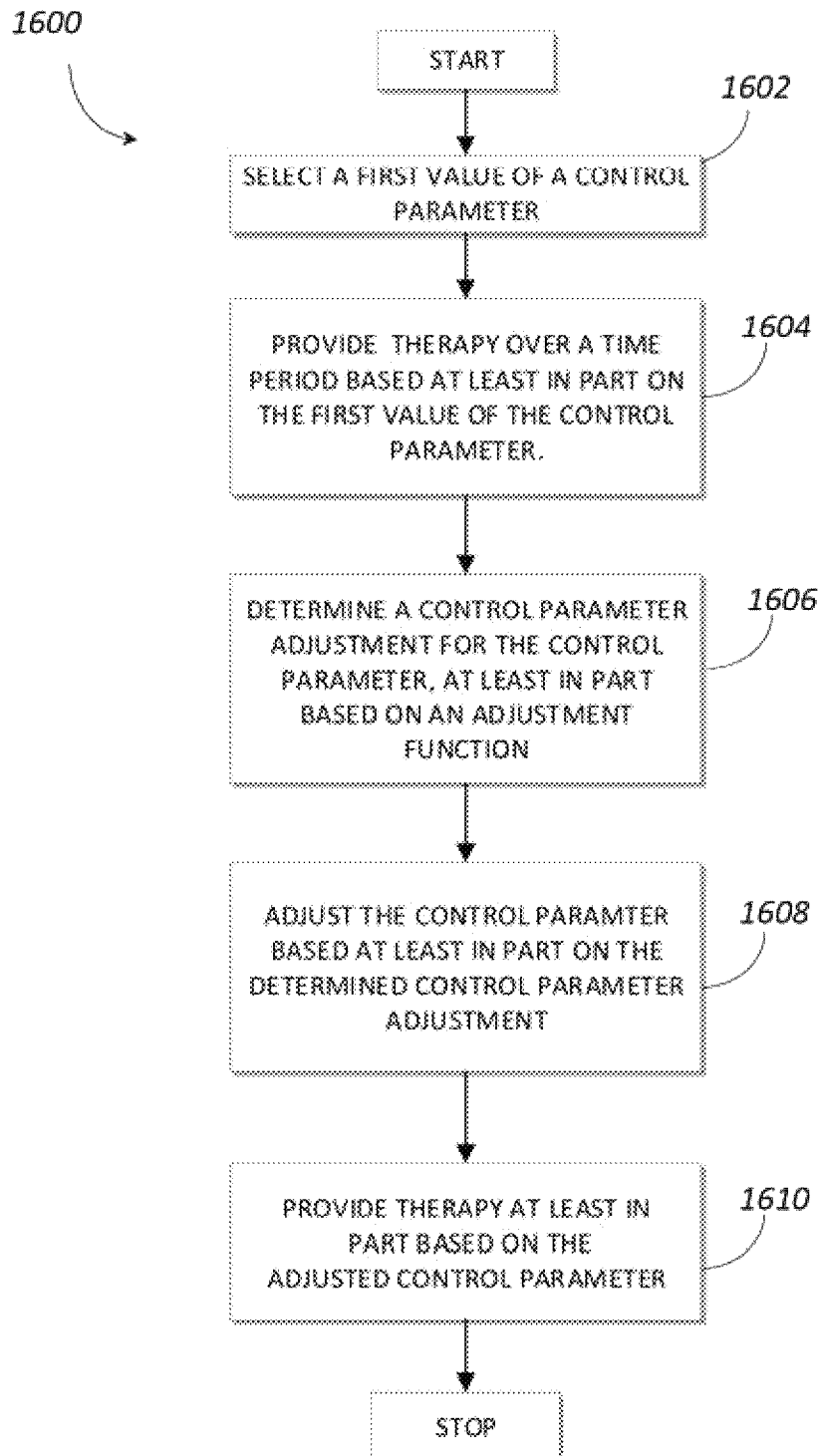
FIG. 16 presents a flowchart of an example automated blood glucose control refinement process based on an adjustment function in accordance with certain embodiments.

FIG. 16 presents a flowchart of an example automated blood glucose refinement process that may use the above-mentioned modification method to control Tmax and/or other control parameters of a glucose control system. The process 1600 may be performed by any system that can autonomously and/or automatically modify a control algorithm and/or a control parameter that affects execution of the control algorithm based on feedback (e.g., from a blood glucose signal) relating to therapy administered to a subject 512. For example, the process 1600 may be performed by one or more elements of the glucose level control system 510. In some cases, at least certain operations of the process 1600 may be performed by a separate computing system that receives blood glucose data from the glucose level control system 510. Although one or more different systems may perform one or more operations of the process 1600, to simplify discussion and not to limit the present disclosure, the process 1600 is described with respect to particular systems.

The process 1600 may be performed automatically and without user interaction. In some cases, a user may trigger the process 1600 via a command or interaction with a user interface. However, once the process 1600 is triggered, the process 1600 may be performed automatically. Further, the process 1600 may be performed continuously, periodically, or in response to a trigger. The trigger may be time based and/or based on a measurement of the glucose level of the subject. For example, the trigger may correspond to a determination that a glucose level of a subject differs by more than a threshold from a predicted glucose level that is predicted by a glucose level control algorithm based on the administering of medicament. Further, the trigger may be based on the activation or first time use of the glucose level control system 510 by the subject 512.

The process 1600 begins at block 1602 where a first value is selected for a control parameter (e.g., a control parameter that may be adaptively modified) of the glucose control system 510. For example, the control parameter can be a Tmax value used in the control algorithm of the glucose control system 510. In some examples, Tmax may be related to one or more parameters in a PK model used by the control algorithm. As another example, the control parameter can be a setpoint (e.g., $G_{set}$ 1524 in FIG. 15) or the target value for the measured value of the blood glucose concentration of a subject 512 (e.g., measured using a CGM sensor).

The first value of the control parameter may be selected based on a baseline value. The baseline value may be associated with clinical data, may be determined based on operation of the glucose level control system 510 for some period of time before performance of the process 1600, or may be determined from a prior performance of the process 1600. Alternatively, or in addition, the baseline value may be selected based on clinical data or a particular prescription for the subject 512. In some cases, the baseline value may be based on clinical data for average users or average users that share certain physiological data with the subject 512. In some cases, the baseline value is determined based on a healthcare provider's assessment of the subject 512. Further, the baseline value may be determined based on an infusion site (e.g., back, stomach, leg, etc.) for the glucose level control system 510. In some cases, the baseline value may be selected based on demographics or characteristics of the subject 512.

At block 1604, the glucose control system 510 provides therapy over a time period to the subject 512. based at least in part on the first value of the control parameter. Further, the therapy may be provided based at least in part on one or more glucose signals received during the time period. The glucose signals may be received from a glucose sensor (e.g., a CGM) and may correspond to a glucose level of the subject. In some cases, the time period may include one or more therapy periods. In some examples, the number of therapy periods included in the time period may be equal or unequal therapy periods. A therapy period may be a time period that corresponds to a single delivered medicament dose, which may include an instantaneous delivery or a delivery of the medicament dose over a period of time. Alternatively, a therapy period may be a time period that encompasses a plurality of medicament dose deliveries. Further, a therapy period may be a time period associated with a defined length of time. Alternatively, or in addition, the therapy period may be defined based on a number of medicament periods. In other words, the time period may vary based on the amount of time it takes to deliver or administer a specified number of doses of medicament (of any type or of a particular type).

In some examples, the time of delivery and dose of the plurality of therapies may be based at least in part on the glucose level signal and the first value of a control parameter of the control algorithm used by the glucose control system 510. The control parameter may include any control parameter that affects operation of the glucose level control system 510 and/or performance of a control algorithm of the glucose level control system 510.

For example, the control parameter can be Tmax, $T_{1/2}$, speed of delivery of a medicament dose, a setpoint for the glucose level, a blood glucose range, a threshold value of blood glucose level (e.g., a maximum or minimum value) and the like. The control algorithm may include any control algorithm and/or PK model used to determine a dose of medicament (e.g., insulin) to administer to the subject 512. In other words, the controller 518 or the processor 530 may use the control algorithm to generate a dose control signal based at least in part on a value (e.g., the first value selected at the block 1602) of the control parameter to cause the delivery device 514 to administer a dose of insulin or other medicament.

Each therapy of the plurality of the therapies provided over the time period, may correspond to a single administering of insulin to the subject 512. This single administering of insulin may be any type of insulin that may be administered for any reason. For example, the insulin dose may be a basal insulin dose, a priming dose, a dose supplied in response to a meal announcement, or a correction dose of insulin. Moreover, each therapy provided may be a medicament other than insulin, such as counter-regulatory agent (e.g., glucagon). In some cases, each therapy delivery may include a plurality of medicament (e.g., insulin and/or counter-regulatory agent) doses supplied or administered to the subject 512 over a therapy period. Further, the plurality of medicament doses may include different types of medicament doses, such as one or more basal doses, one or more meal doses associated with one or more meal announcements, one or more corrective doses, etc.

In some examples, the value of the control parameter that is being adjusted may change from one therapy period to another therapy period during the time window. For example, the value of the control parameter may change by a given amount in the beginning of each therapy period or group of therapy periods. In some other examples, the value of the control parameter may change by a given amount after certain number of therapies. In some examples, the amount by which the control parameter is changed may be determined based on one or more receding therapy periods in the time window. In some cases, the block 1604 may include one or more of the embodiments described with respect to the process 1304.

In some examples, during the therapy period or one or more therapy periods of the plurality of therapy periods included in the time period, therapy data may be obtained and/or stored. With reference to FIG. 15, in some examples, therapy data may include the glucose signal, G(t) 1524, the calculated or actual delivery time ($t_{c,j}$ 1516) and the estimated or delivered amount of a counter-regulatory agent ($C_j$ 1514). This therapy data may be stored in the memory 540 of the glucose level control system 510. Further, the therapy data may include a total amount of the counter-regulatory hormone administered during a therapy period. Alternatively, or in addition, other parameters and data associated with each therapy period may be stored in the memory 540. For example, the total amount of insulin administered, an amounts of insulin delivered ($U_i$ 1508), a delivery time ($t_{u,i}$ 1510) of the insulin delivered during each therapy period, data received from other sensors that may measure one or more physiological parameters of the subject, data received from the subject or user (e.g., via a user interface), and the like.

At block 1606, the glucose level control system 510 determines a control parameter adjustment for the control parameter. The control parameter adjustment may be based at least partially on the therapy data. In some embodiments, the adjustment may be determined using an adjustment function. For example, the adjustment function may be the function $f(y_k,g_k)$ for modifying Tmax according to equation 4. In some examples, the control parameter adjustment may be determined by analyzing glycemic control of blood glucose in the subject as indicated by the glucose level signal (e.g., G(t) 1524 or the CGM trace). Analyzing the glycemic control of the blood glucose in the subject may include tracking the blood glucose level of the subject 512 over time. Further, analyzing the glycemic control of the blood glucose in the subject may include comparing the blood glucose level of the subject 512 over time to a predicted blood glucose for the subject 512 over time estimated based on the PK model and control parameter values used in the control algorithm. In some examples, the value of the adjustment function $f(y_k,g_k)$ may be calculated at least in part using the estimated or actual values of $t_{c,j}$ 1516, $C_j$ 1514, and $G_{c,j}$, (where j varies from 1 to the number of counter-regulatory provided during the time period). In some other examples, determination of the adjustment function $f(y_k,g_k)$ may include a statistical analysis based on the estimated or actual values of $t_{c,j}$ 1516, $C_j$ 1514, and $G_{c,j}$, (where j varies from 1 to the number of counter-regulatory provided during the time period). In some such examples, the statistical analysis may be based on statistical quantities and/or the analytical tools described below.

In some cases, the adjustment to the control parameter may be determined based on the number of hypoglycemia 1528 and/or hyperglycemia 1526 events and/or duration of each event. In some examples, the adjustment to the control parameter may be determined based on the difference between measured glucose level and the setpoint ($G_{set}$ 1524). In some examples, the adjustment may be determined based on the time intervals during which the glucose level stays within a target range (e.g., between $G_{max}$ 1520 and $G_{min}$ 1522). In some cases, the adjustment may be determined based on the stability of the measured blood glucose level for the subject 512 or less volatility in the blood glucose level of the subject 512. For example, a statistical analysis may be performed to determine the distribution rate of change for G(t) beyond one or more threshold rates.

In some cases, the adjustment to the control parameter may, at least partially, be determined by analyzing one or more signals received from one or more subject sensors that measure one or more physiological parameters of the subject (e.g., heart rate, temperature and the like). In yet other examples, the adjustment to the control parameter may be determined based on an assessment or input received from the subject 512 (e.g., using a user interface of the AMD). For example, if the subject 512 feels woozy, dizzy, lightheaded, nauseous, or otherwise uncomfortable during one or a plurality of therapy periods, the subject 512 may, via, for example, a touchscreen user interface or other interface of the AMD, indicate how the subject 512 is feeling.

The adjustment may be determined in real-time or substantially in real-time accounting for the processing speed of the hardware processor 530, the glucose level control system 510, or the time for the subject to provide an assessment of his or her condition to the glucose level control system 510. In some cases, the adjustment to the control parameter may be determined by a computing system that is in communication with the glucose level control system 510. For example, the glucose level control system 510 may transmit the therapy data, to another computing system, such as a local computing system, a smartphone, or a cloud-based computing system. Further, the glucose level control system 510 may transmit the therapy data and data associated with the control parameters values to the computing system. The computing system may determine the adjustment that better manages the subject's 512 blood glucose level in the next time period.

At block 1608, the glucose level control system 510 adjusts the control parameter using the control parameter adjustment determined at the block 1606. In some examples, the adjustment may be performed autonomously or automatically. In some other examples, the control parameter adjustment determined at block 1606 may be presented to the subject or other user (e.g., parent, guardian, clinician, etc.) via a user interface (e.g., a touchscreen display). In some such cases, the subject or other user may be able to confirm or modify the control parameter adjustment. In other cases, the display of the control parameter adjustment may be presented for informational purposes and may not be adjustable by a user. In some cases, the control parameter may be adjusted only after receiving the user confirmation (e.g., a user interaction with a user interface). In some other examples, where the adjustment is determined by a computing system, the adjustment value may be presented to user via a user interface of the glucose control system or a user interface of the computing system. In some cases, the user may adjust the control parameter of the glucose control system using the adjustment value received from or presented by the computer system.

The adjustment at block 1608 may cause a change in the operation or execution of the control algorithm. This change in the execution of the control algorithm may result in a change in one or more factors associated with the provisioning of therapy to the subject 512. For example, the change in the execution of the control algorithm may result in a change in an amount of medicament delivered, a timing of the delivery of the medicament, a rate at which a dose of medicament is delivered to the subject 512, a target setpoint or target range for the blood glucose of the subject, a threshold used in determining whether to deliver medicament (e.g., a threshold difference from the target setpoint), or any other factor that may affect therapy delivered to the subject 512.

In some cases, the adjusted value of the control parameter may be output to a user (e.g., the subject or a parent). The user may then configure the glucose level control system 510 based on the selected control parameter value. Alternatively, or in addition, the glucose level control system 510 may automatically adjust the value of the control parameter. In some cases, the user may be provided with an opportunity to confirm the adjustment. In other cases, the adjustment may occur automatically without confirmation. However, the adjustment may be presented to the user (e.g., the subject or a healthcare provider) and/or logged in a therapy log.

At block 1610, the glucose level control system 510 provides therapy based at least in part on the updated control parameter that is updated at the block 1608. The new value of the control parameter may be maintained during a second time period. The second time period may refer to a specific amount of time, an amount of time to deliver a particular number of medicament doses, or a particular number of medicament doses.

The process 1600 may be repeated during subsequent time periods. In some examples, the process may be repeated periodically (every 24 hours, every two days, every week, or other time intervals). In some cases, the time period may be provided by the subject or a user. Further, the process may be repeated in response to a command. In some cases, the process may be repeated in response to determining that the subject's 512 blood glucose level does not satisfy one or more criteria for a particular amount of time. For example, the process may be repeated when a statistically significant difference between the measured mean value of the BGL and a target BGL exceeds a threshold, or a number of hypoglycemia and/or hyperglycemia detected exceeds a threshold number during a specific amount of time.

In some examples, the process 1600 may be used to adjust several control parameters that affect the therapy delivery by the glucose control system. In some such examples, the process 1600 may be used to adjust a first control parameter during a time period and to adjust a second control parameter during a second time period. The second time period may be immediately after the first time period or delayed by a particular time. In some implementations, the control system 510 may determine when to adjust the control parameter. In some examples, a delay between periods of control parameter adjustment may be determined at least in part on the glycemic control of the glucose signal. In some cases, the delay may be determined based on input received from a user. Further, the adjustment of the second control parameter may be at least partially determined based on the determined adjustment for the first control parameter.

In some embodiments, a third control parameter may be adjusted during a third time period. The adjustment of the third control parameter may immediately follow the adjustment of the second control parameter or may occur after a delay. The delay may be determined at least in part based on the glycemic control of the subject after the second control parameter is adjusted. In some cases, the glucose control system may be configured to sequentially adjust the first and second, or the first, second, and third control parameters when the glycemic control of the subject satisfies one or more threshold conditions. In some examples, the duration of the time period during which a control parameter is adjusted may differ from that of the first and second control parameters.

As described above, the process 1600 may be used to adjust one or more control parameters that affect the delivery of insulin. However, the process 1600 is not limited as such and may be used to modify one or more control parameters that affect the delivery of other medicaments, such as a counter-regulatory agent (e.g., glucagon). In some cases, the process 1600 may be used to recommend a change in insulin and/or counter-regulatory agent delivery without modifying the delivery. This can be advantageous for generating recommendations regarding counter-regulatory agent in a non-bi-hormonal glucose level control system 510 that does not support counter-regulatory agent, or that supports the use of counter-regulatory agent, but does not have the counter-regulatory agent available.

Implementation of Statistical Analysis in Automated Blood Glucose Control Refinement As described above, a value (e.g., a baseline value or optimal clinical value) of one or more control parameters of a PK model and/or control algorithm used by a glucose control system 510 may be determined by statistical analysis of therapy data sets (e.g., glycemic control information) collected from multiple cohorts of subjects (e.g., 20, 50, 100, 200 subjects) during a clinical study. In some examples, the control parameter (e.g., Tmax) may be directly measured for the subjects within each cohort (e.g., based on results of blood analysis following manual or automated medicament administrations). These measurements may be used to determine an optimal value of a control parameter (e.g., Tmax) to be used in a glucose control system. In some cases, the blood glucose level (BGL) of the subjects may be controlled and recorded for a given period (e.g., one week, two weeks, one months, or other periods) using identical or nearly identical glucose control systems. The subjects in each cohort may use the same values for a control parameter of the glucose control system while the subjects in different cohorts may use different values of the same control parameter. Subsequently, the measured therapy data sets, (e.g., comprising measured and/or determined glycemic control information for the subjects) over the given period may be compared using statistical analysis to evaluate an optimal value of the control parameter. For example, the measured glycemic control of subjects in a first cohort in response to setting Tmax to a first value, may be compared to the measured glycemic control of subjects in a second cohort in response to setting Tmax to a second value. Such comparison may include various statistical analysis that can reveal statistically significant differences between measured glycemic controls. For example, the mean value, variance and/or standard deviation of the measured blood glucose level data obtained from the first and second cohort, may be compared to a set of reference values that may be obtained from a third cohort of subjects with normal blood glucose level (e.g., nondiabetic subjects). To generate accurate results, such clinical studies often require several cohorts each comprising a large number of subjects (e.g., large enough to produce enable statistical analysis) and therefore large number of identical glucose control systems. For example, in some studies 10, 20, 50, or 100 subjects and glucose systems may be required. As such, determining the optimal value of one or more control parameters based on clinical studies can be expensive and time consuming. Moreover, clinical studies typically cannot capture unique physiological characteristics of and real-time physiological changes of a subject (even studies include several large cohorts).

A portable glucose control system that monitors the BGL in real time and autonomously or automatically provides medicament to a subject, may collect and store therapy data sets that, similar to those collected in clinical studies, may include sufficient number data points for a statistical analysis. In some examples, therapy data may include glycemic control information (e.g., received from a CGM sensor), other physiological effects of the therapy (e.g., obtained from subject sensors or the subject), an amount and type of medicament delivered, medicament delivery times, and the like. Advantageously, these therapy data sets may be used to determine an optimal value of one or more control parameters of the glucose control system or a value for the one or more control parameters of the glucose control system that provides improved diabetes management compared to a default value, baseline value, or initial clinically determined value. The optimal or improved values may be determined based on statistical analysis, including the type of statistical analysis that may be used in clinical studies. In some embodiments, the statistical analysis may include calculating one or more statistical quantities such as mean, variance, standard deviation, various statistical distributions (e.g., those described with respect to FIG. 17 below) and the like. On board and real-time (or near real-time) evaluation of values of one or more control parameters of a glucose control system based on therapy data collected during one or more therapy periods eliminates the need for expensive and time consuming clinical studies and may improve the maintenance of a subject's diabetes by, for example, taking into account unique physiological characteristics of and real-time physiological changes of a subject. Moreover, on board evaluation of control parameter values provides for faster and more accurate diabetes evaluation and management compared to clinical testing. Some of the embodiments described herein may be used to determine optimal values of one or more control parameters that may be used by a user to adjust the control parameters via a user interface of the glucose control system. In some cases, the glucose control system may autonomously adjust one or more control parameters using the determined optical values.

The therapy data collected by a glucose control system may include glycemic control information, information related to medicament delivery times, doses of medicament provided, the BGL level at the time of medicament delivery (e.g., measured based on a glucose signal obtained from a CGM sensor), the physiological effects of the medicament on a subject (e.g., BGL in a time period after medicament delivery, subjects assessment and the like), and any the type of data that may be determined from therapy provided to the subject. In some embodiments, the glucose control system may collect therapy data during one or more therapy periods. With reference to FIG. 15, the collected and stored therapy data during each therapy period (e.g., a period starting at is 1504 and ending at $t_E$ 1506) may include, but is not limited to: a CGM trace G(t) 1502, delivered doses (Ui 1508) and delivery times (time $t_{u,i}$) of insulin, delivered or determined doses ($C_i$ 1514) and delivery times ($t_{c,i}$ 1516), of a counter-regulatory agent (e.g., glucagon) and the like. The therapy data may be stored in a memory (e.g., a flash drive, a solid-state drive, a hard disk, or any other type of non-volatile memory) of the glucose control system as one or more data sets. Each data set may be associated with one or more categories of therapy data or a specific therapy period during which the therapy data was collected. In some cases, the value of the one or more control parameters may change from one therapy period to another therapy period. For example, the value of the control parameter may change by a given amount in the beginning of a therapy period or a group of therapy periods. The value of the control parameter may be changed automatically by the glucose level control system 510 or by a user via a user interface. In some cases, the control parameter may be changed by a given amount after certain number of therapy periods. The amount by which the control parameter is changed may be determined based on therapy data collected during one or more preceding therapy periods. Alternatively, or in addition, the amount by which the control parameter is changed may be provided by a user via a user interface. In some cases, the duration of one or more therapy periods is selected such that the measured or determined data sets are sufficiently large for statistical analysis. In some examples, an uncertainty associated with an optimal or improved value of a control parameter determined using statistical analysis may depend on the size of the data set used for the analysis.

In some embodiments, the process 1300 may be used to determine a value (e.g., an optimal value) of a control parameter using statistical analysis. For example, statistical analysis may be used to determine the therapy effects at block 1306, block 1314, or to compare the therapy effects resulting from different control parameter values at step 1316. In some such examples, at block 1308, the second value of the control parameter may be provided by the user (e.g., the subject or the guardian) based at least in part on the first effect and outcomes of the statistical analysis performed on the therapy data collected and/or stored during the first therapy period (block 1304). In some examples, at step 1316, a statistical analysis may be performed based at least in part on the first effect and the second effect to obtain a comparative assessment. The comparative assessment may be used to determine whether one of a pair or set of values of a control parameter results in an improved glycemic control of the subject compared to the other values used for the control parameter. In some embodiments, the determined value of the control parameter at block 1316 may be provided to the subject, a guardian or a healthcare provider via a user interface of the glucose control system 510 and/or a computing system (e.g., a smartphone, a notebook a personal computer and the like) connected to the glucose control system (e.g., via a wireless link). In some such embodiments, the subject, the guardian or the healthcare provider may change the value of the corresponding control parameter to the determined value by an interaction with a user interface before the next therapy period (e.g., at block 1318). Alternatively, or in addition, the glucose level control system 510 may automatically change value of the control parameter to the determined value and proceed to block 1318. In some such cases, the user may be provided with an opportunity to confirm the modification. In other cases, the modification may occur automatically without confirmation. However, the modification may be presented to the user (e.g., the subject or a healthcare provider) and/or logged in a therapy log.

In some examples, the first and second therapy provided to the subject during the first (block 1304) and second (block 1312) therapy periods, may include a plurality of therapy deliveries. During the first (block 1304) and second (block 1312) therapy periods, a first and second first therapy data may be obtained by the control system 510. In some such cases, the therapy data may comprise glycemic control information that at least includes the glucose signal received during the corresponding therapy period. Determining the first effect may include calculating statistical characteristics of the therapy data collected during the plurality of therapies provided during each period. For example, the control system 510 may calculate the mean value, deviation from mean value, and the variance of the measured BGL. In some cases, the control system 510 may calculate one or more quantities (e.g., statistical quantities) to quantify the average blood glucose level and its deviation from a baseline level. In some embodiments, the control system 510 may determine one or more quantities (e.g., statistical quantities) to evaluate the variability of glycemic control and the associated risks (e.g., risk of hypoglycemia or hyperglycemia) or quantify the average blood glucose level and its deviations from a baseline (e.g., normal) level. In some cases, the duration of the second period may be equal to the duration of the first period. Alternatively, or in addition, the duration of each period may be selected such that each period includes the same number of therapies provided to the subject. In some embodiments, the duration of each period may be selected such that the number of times therapy is administered during the time period is large enough to enable statistically significant assessments. In some cases, at block 1316, the comparison between the first effect and the second effect, may include statistical analysis of statistical data generated based on the data collected during the first and second period.

In some examples, in addition to the optimal values of one or more control parameters, the control system may generate a control parameter optimization report that may include the statistical quantities calculated during the optimization process. Further, the report may include a graphical representation of the therapy data and related risk assessments. In some such examples, this report may be used by the subject or a healthcare provider to make decisions related to selecting a determined optimal parameter value. Additionally, the control parameter optimization report may include information that may be used by the subject or a healthcare provider to modify the overall strategy for managing the subject's glycemic control. For example, modifying the mealtime, content or amount of meal consumed by the subject, and the like.

Figure 17:
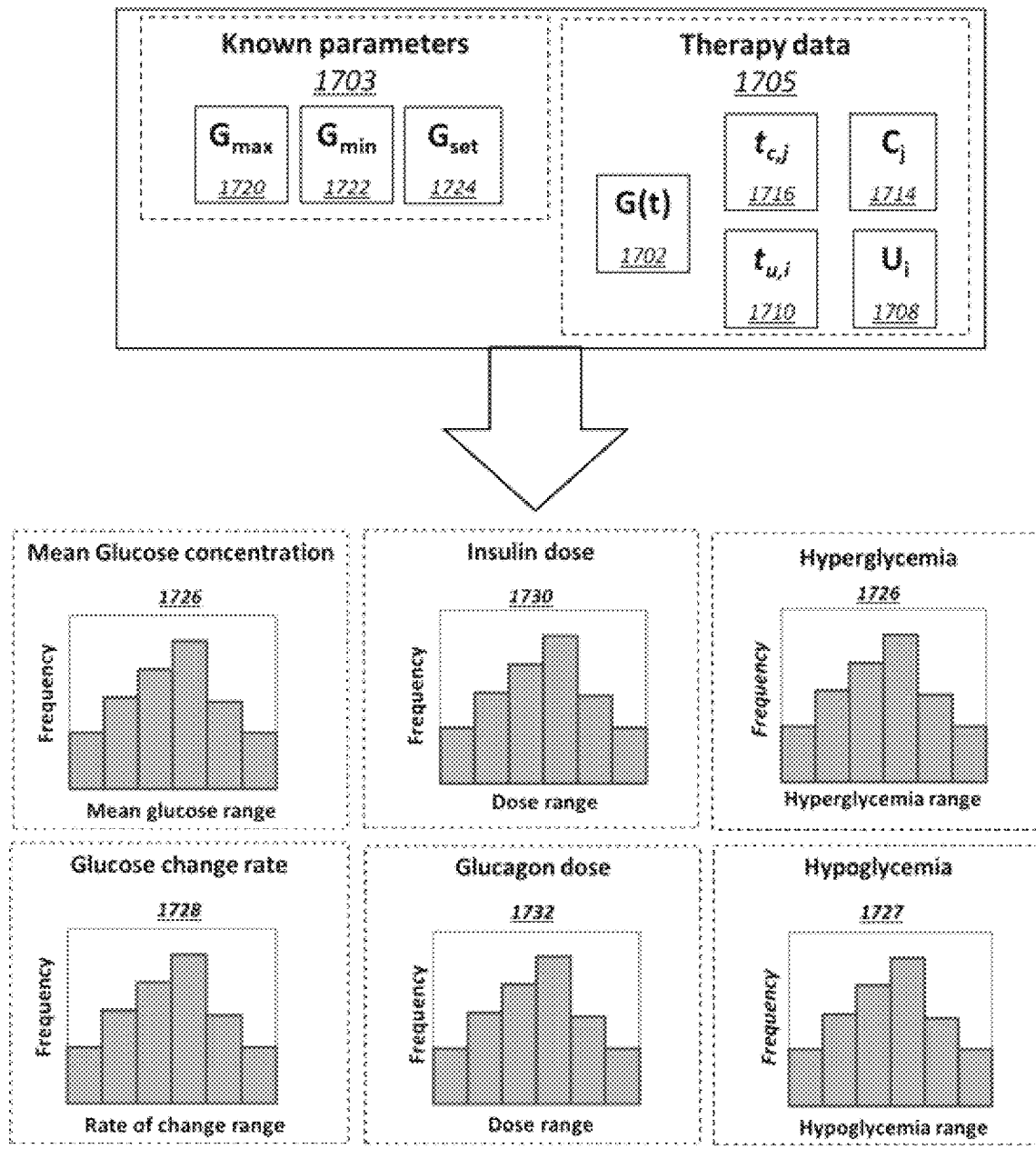
FIG. 17 illustrates some examples of statistical quantities that may be generated and utilized by the blood glucose control system as part of statistical analysis.

FIG. 17 illustrates some examples of statistical quantities that may be generated and utilized at blocks 1306 and 1314 of the process 1300, using the therapy data 1705 during a therapy period, and known parameters of the control system 1703. In some embodiments, during the therapy period the value of certain control parameter may be fixed and/or selected based on baseline values (e.g., outcomes of previous clinical studies) or a previously determined value (e.g., by a different control parameter modification and/or optimization process). With reference to FIG. 15, in the example shown in FIG. 17, $G_{min}$ 1722 (lower bound for normal BGL), $G_{max}$ 1720 (upper bound for normal BGL) and $G_{set}$ 1724 (target BGL) are assumed to be known values provided by the subject, the user, a health care provider or determined by a computing system based on a set of clinical data. For example, $G_{min}$ 1722 may between 65 mg/dL and 75 mg/dL, $G_{max}$ 1720 may be between 175 mg/dL and 185 mg/dL and $G_{set}$ 1724 may be between 70 mg/dL and 180 mg/dL. In some examples, $G_{set}$ 1724 may be a value (e.g., an optimal) determined by a previous optimization process (e.g., the process 1300). G(t) 1702 (the CGM trance or the measured glycemic control), $U_i$'s 1708, $t_{u,i}$'s 1710, $C_i$'s 1514 and $t_{c,i}$'s 1716 may be included in the therapy data collected during the therapy period. In some examples, the therapy data 1705 may be used to generate various types of statistical quantities. For example, the therapy data 1705 may be used to generate probability distributions (e.g., discrete or continuous) and/or frequency distributions (e.g., absolute, relative, or cumulative) for certain measured or determined values. For example, the distributions associated with the glucose concentration 1726 (e.g., portions of the therapy period during which the glucose signal was within selected ranges), glucose change rate 1728 (e.g., portions of the therapy period during which the glucose change rate signal was within selected ranges rates), insulin dose 1730 (percent of insulin doses provided within selected dose ranges), glucagon dose 1732 (percent of glucagon doses provided within selected dose ranges), hyperglycemia 1734 (percent of hyperglycemia events detected wherein the glucose signal was above $G_{max}$ by an amount within selected ranges), hypoglycemia 1736 (percent of hypoglycemia events detected wherein the glucose signal was below $G_{min}$ by an amount within selected ranges) and the like. In some examples, one or more characteristic of these statistical distributions (mean, variance, deviation from mean, and the like) or a specific combination of some characteristics of these statistical distributions, may be used to determine (e.g., quantify) the effect of a therapy. In some examples the therapy data considered to generate certain statistical data (e.g., a histogram) may be filtered to exclude the data points collected during certain events. For example, during a mealtime, during exercise, and the like. In some examples, time bins associated with these events may be specified by a user through a user interface.

In some embodiments, the statistical analysis may comprise analytical methods and tools that can compare the effect of different control parameter values. Some examples of analytical methods and tools that can be used with one or more of the embodiments described herein are described in the article "*Statistical Tools to Analyze Continuous Glucose Monitor Data*" (W. Clarke et al., Diabetes Technology and Therapeutics, vol. 11, S45-S54, 2009), which is hereby incorporated by reference in its entirety herein. Examples of methods and tools that may facilitate extraction of information from complex and voluminous measured glycemic control information during therapy periods, are discussed herein. In some cases, the therapy data used for statistical analysis includes the glucose trace of the subject or G(t). In some examples, G(t) may be a time-stamped series of glycemic data received from a CGM sensor (see FIG. 17). In some examples, the glucose signal obtained from CGM may represent blood glucose level as a discrete time series that approximates G(t) in steps determined by the resolution of the particular device (e.g., a reading every 2 min, 5 min, 10 min and the like). In some examples, statistical analysis may be performed on the therapy data (e.g., the glucose signal received from a CGM sensor) to provide an assessment (e.g., a comparative assessment) related to: (1) average blood glucose level and deviations from normal glycemic control (sometimes referred to as normoglycemia), (2) variability and risk assessment, and (3) clinical events, such as post-meal glucose excursions and hypoglycemic episodes. In some embodiments, the assessment may be made based on two sets of therapy data collected during two time periods. In some such examples, the assessment may be used by the control system 510 to determine whether the glycemic control for a subject has been improved from a first therapy period to a second therapy period. In some examples, the assessment may be used by a health care provider to evaluate the glycemic control of a subject during one or more time periods.

In some cases, the blood glucose control system may determine three values of average blood glucose: the mean value (e.g., computed for the entire G(t) measured during a therapy period or part of a therapy period), a pre-meal mean value (e.g., computed for the time window of 60-120 min after the meal), and post-meal mean value (e.g., computed for the time window of 0-60 min before meal). Computing of pre- and post-meal averages and the difference between the averages can serve as an indication of the overall effectiveness of pre-meal bolus timing and bolus amount. In some examples, deviation from target or normoglycemia may be evaluated by determining percentages of time spent within, below, or above preset target limits (e.g., $G_{min}$=70 and $G_{max}$180 mg/dL). In some examples, the percentage of time within each range may be calculated via linear interpolation between consecutive glucose readings. In some other examples, percentage of time within additional ranges can be computed. In some such examples, the probability of occurrence of extreme hypoglycemia and hyperglycemia may be also evaluated. To quantify variability of blood glucose level, in some examples, standard deviation and variance may be used to compute variability of BGL. In some cases, a risk index may be defined that can serve as a measure of overall glucose variability when focusing of the relationship between glucose variability and risks for hypo- and hyperglycemia. In some examples, an individual function may be calculated to split the overall glucose variation into two independent sections related to excursions into hypo- and hyperglycemia, and at the same time equalize the amplitude of these excursions with respect to the risk they carry. For example, a BGL transition from 180 to 250 mg/dL may appear threefold larger than a transition from 70 to 50 mg/dL, whereas if converted into risk, these fluctuations would appear equal. In some cases, analysis of BGL rate of change (e.g., measured in mg/dL/min) may be used to evaluate the dynamics of BGL fluctuations on the time scale of minutes. In other words, this is an evaluation of the "local" properties of the system as opposed to "global" properties discussed above. In some examples the local properties may be assessed at a neighborhood of any point in time by the value BGL, its first or, sometimes, second derivatives (acceleration).

In some examples, in addition to statistical analysis of the therapy data, in the blocks 1306, 1314, and 1316 of the process 1300, a statistical analysis of the user inputs provided during the first or second therapy period may be used in determining or comparing the therapy effects. For example, the number of times and time of the day that the subject has indicated certain symptoms, may be used to determining therapy effects.

In some cases, in addition to the statistical analysis of the therapy data in the blocks 1306, 1314, and 1316 of the process 1300, a statistical analysis of the biomedical or physiological data received from one or more subject sensors (e.g., a smart watch, weight sensor, etc.) may be used in determining or comparing the therapy effects. For example, subject's temperature, blood pressure, heart rate), from a weight sensor, or any other type of biomedical sensor.

In some examples, the process 1300 may be modified to determine the optimal value of Tmax, or a value of Tmax that provides improved maintenance of the subject's diabetes, by reducing Tmax (increasing the aggressiveness of the therapy) after each therapy period in a series of therapy periods, until a statistical assessment shows that further reduction of the Tmax does not improve the mean glucose level without increasing the probability of hypoglycemia. Improved maintenance of the subject's diabetes may include maintaining a mean glucose level closer to a setpoint glucose level range or reducing fluctuations in mean glucose level over time compared to prior control value (e.g., Tmax) settings. It should be understood that other metrics may be used to measure an improvement of maintenance of the subject's diabetes, such as reduction in hypoglycemia risk events or reduction in administration of insulin without increasing diabetic effects or corresponding risks.

Figure 18:
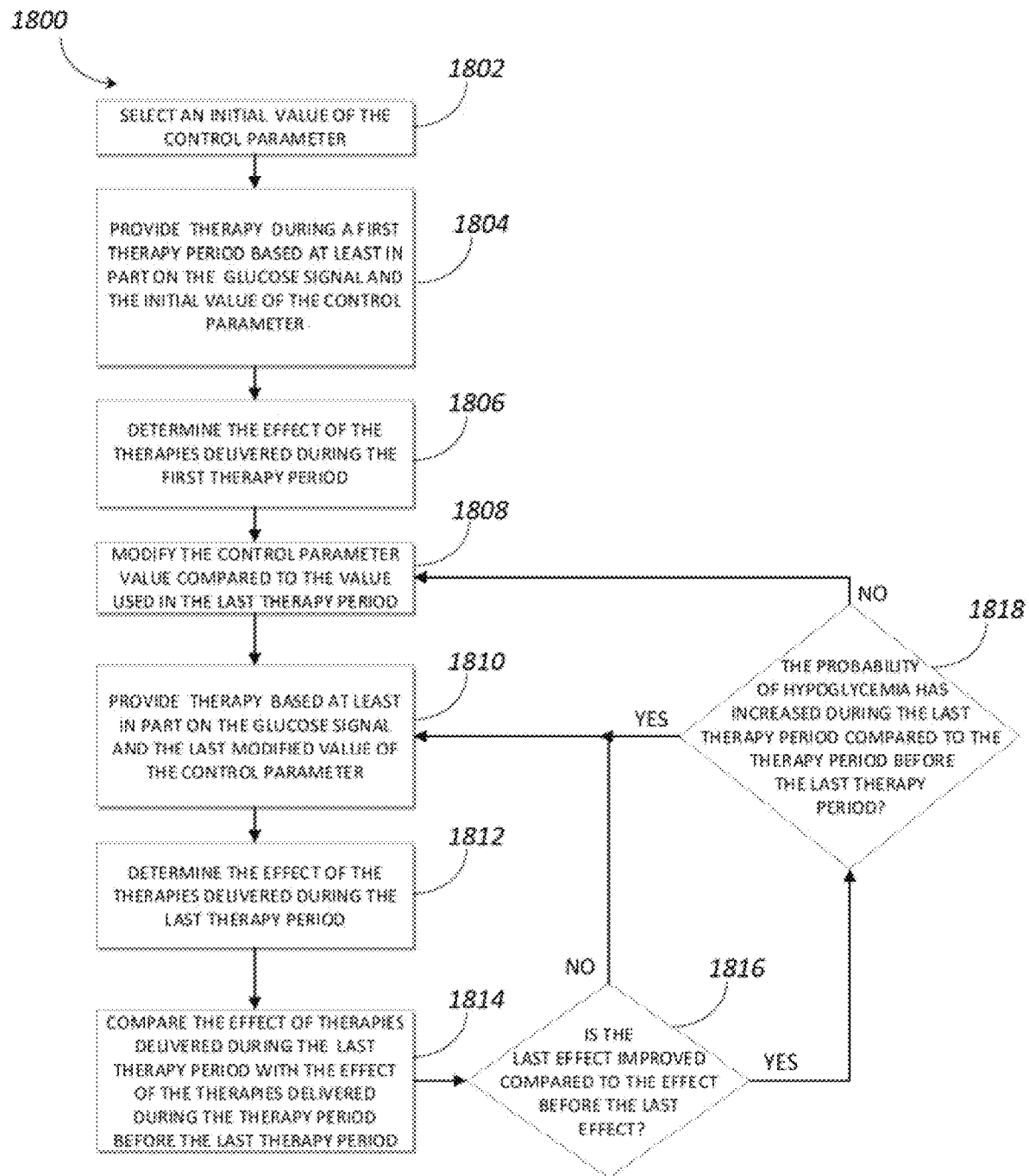
FIG. 18 presents a flowchart of an example automated blood glucose control refinement process in accordance with certain embodiments.

FIG. 18 presents a flowchart of an example automated control parameter refinement process in accordance with certain embodiments. The process 1800 may be performed by any system that can autonomously and/or automatically modify a control algorithm and/or a control parameter that affects execution of the control algorithm based on feedback (e.g., from a blood glucose signal) relating to therapy administered to a subject 512. For example, the process 1800 may be performed by one or more elements of the glucose level control system 510. In some cases, at least certain operations of the process 1800 may be performed by a separate computing system that receives blood glucose data from the glucose level control system 510. Although one or more different systems may perform one or more operations of the process 1800, to simplify discussions and not to limit the present disclosure, the process 1800 is described with respect to particular systems.

The process 1800 may be performed automatically and without user interaction. In some cases, a user may trigger the process 1800 via a command or interaction with a user interface. However, once the process 1800 is triggered, the process 1800 may be performed automatically. Further, the process 1800 may be performed continuously, periodically, or in response to a trigger. The trigger may be time based and/or based on a measurement of the glucose level of the subject. For example, the trigger may correspond to a determination that a glucose level of a subject differs by more than a threshold from a predicted glucose level that is predicted by a glucose level control algorithm based on the administering of medicament. Further, the trigger may be based on the activation or first time use of the glucose level control system 510 by the subject 512.

In some embodiments, the glucose level control system 510 may perform the process 1800 in order to adjust one or more control parameters of the glucose control system 510 to improve the glycemic control of a subject. The control parameter may include any control parameter that affects operation of the glucose level control system 510 and/or performance of a control algorithm of the glucose level control system 510. In some such embodiments, in addition to improving the glycemic control of the subject, the process 1800 may take into account the risk of hypoglycemia in the subject. In some embodiments, the process 1800 may include one or more of the embodiments previously described with respect to the process 1300.

The process 1800 begins at block 1802 where an initial value is selected for a control parameter of the glucose control system (e.g., Tmax or other control parameters of the glucose control system selected to be optimized). The control parameter can be a control parameter of a pharmacokinetic (PK) model used by a control algorithm PK of the glucose control system 510. In some examples, the control parameter may be a time until insulin within blood plasma of the subject reaches a particular concentration level subsequent to administration of an insulin dose. In some cases, the initial value of the control parameter may be based on therapy delivered during a time period prior to the first therapy period, a clinical value, or a body mass of the subject.

In some examples, the initial value of the control parameter may be selected using one or more of the embodiments described with respect to the block 1304 of the process 1300. In some embodiments, the control parameter may be a control parameter used by the control algorithm of the glucose control system to account for accumulation of insulin in a subject. In some embodiments the control parameter may be used to control an insulin dosing response of the control algorithm to a blood glucose excursion in the subject based on a glucose level signal received from a glucose level sensor (e.g., a SGM sensor).

At block 1804, the control system 510 may provide therapy during a first therapy period based at least in part on the glucose level signal and the initial value of the control parameter. In certain embodiments, the block 1804 can include one or more of the embodiments previously described with respect to the block 1304 of the process 1300. In some embodiments, the first therapy data may include glycemic control information resulting from the delivery of the first therapy. In some examples, the system may store all or some of the therapy data generated during the first therapy period in a memory of the control system 510. In some examples, the therapy provided at block 1804, may comprise a plurality of medicament deliveries.

At block 1806, the control system 510 may determine the therapy effect of the therapy provided during the first therapy period using statistical analysis of the first therapy data collected and stored at block 1804. In some examples, the statistical analysis may include calculating the statistical quantities discussed above and with reference to FIG. 17. In some cases, the statistical analysis may include regression analysis between certain measured and/or calculated parameters at block 1804. In some such examples the regression analysis may include determining an autoregression model. In some examples, the control system 510 may determine the therapy effect using one or more of the embodiments described with respect to the block 1306 of the process 1300.

At block 1808, the control system 510 may modify the value of the control parameter compared to the initial value selected at block 1802 or the value used in the last therapy period. In some examples, the modified value may be a value that makes the therapy more aggressive (e.g., aggressive by a significant amount). For example, when the control parameter is Tmax, at block 1808 the value of Tmax may be reduced to an amount less (e.g., 5, 10, 15 minutes, or more) than the value used in a previous therapy period (e.g., the initial value or the last modified value). In some examples, the modified value of the control parameter may be received from a user interface of the blood glucose control system responsive to a user interaction with the user interface. The previous therapy period may be the first therapy period or any earlier therapy period. In some examples, the value for Tmax may be lowered by a significant amount (e.g., 10 minutes, 15 minutes, or other values). Further, the amount by which Tmax is reduced may be smaller than a previous reduction during a previous iteration of the process 1800. In some embodiments, the control parameter may be modified automatically without action by a user. In some cases, modifying the control parameter may change a timing, a dosage size, or a speed of injection of insulin administered to the subject.

At block 1810, the control system 510 provides therapy to the subject based at least in part on the glucose signal and the modified value of the control parameter received from block 1808. In some examples, the duration of the therapy period (at block 1810), may be equal to the duration of one or more previous therapy periods. In some other examples, the duration of the therapy period may be determined based on the determined therapy effects of the therapies delivered during one or more previous therapy periods. In some examples, at block 1810 the system may store all or some of the therapy data generated during the therapy period. In some examples, the therapy provided at block 1810, may comprise a plurality of medicament deliveries. In some cases, the therapy data may include glycemic control information resulting from the delivery of the therapy.

At block 1812, the control system 510 determines the therapy effect of the therapy provided at block 1810 during the last therapy period. In some examples, the therapy effects may be determined based at least in part on the therapy data obtained and stored at block 1810. In some examples, the control system 510 may determine the therapy effect using one or more of the embodiments described with respect to the block 1306 of the process 1300.

At block 1814, the control system 510 performs a statistical analysis based at least in part in the determined therapy effect of the therapies provided and stored during the last therapy period and the therapy period before the last therapy period to obtain a comparative assessment. In some such examples the comparative assessment may be based on statistical analysis of determined effects and the therapy data collected during the corresponding therapy periods. In some examples, the statistical analysis may include generating statistical quantities (e.g., distributions shown in FIG. 17) using the therapy data. In some examples, the statistical analysis may include the analytical method described above. In some such examples, one or more characteristics of the statistical data may be used to compare the therapy effects. In some examples, the statistical analysis may include calculating one or more of a mean, a median, a mode, a standard deviation, a rate, a ratio, or a probability based on the therapy data obtained in the last two therapy periods or the determined effects of the therapies provided during the last two periods.

At the decision block 1816, the control system 510, based at least in part on the comparative assessment received from block 1814, the control system 510 may determine whether the value of the control parameter used during the last therapy period has improved the glycemic control for the subject compared to the therapy period before the last therapy period. In some embodiments, the control system 510 may determine whether the modified value for the control parameter has resulted in statistically significant improvement in glycemic control. In some embodiments, the control system 510 may determine whether the modified value for the control parameter has resulted in an improvement of a physiological parameter of the subject. In these embodiments, the physiological parameter may be determined based at least in part on the glucose level signal received from a glucose level sensor.

If the control system 510 determines at the decision block 1816 that the glycemic control for the subject is not improved, the control system 510 may return to the block 1810 and continue providing therapy to the subject based on the last modified value of the control parameter without any further modification.

If at the decision block 1816 the control system 510 determines that the value of the control parameter used during the last therapy period has improved the glycemic control for the subject compared to the therapy period before the last therapy period, the control system 510 proceeds to decision block 1818. In some cases, the improvement in the glycemic control should be larger than a threshold level before the system 510 proceeds to block 1818. In some cases, the control system proceeds to block 1818 if the modified value of the control parameter results in a reduced occurrence of blood glucose excursions compared to the first value of the control parameter.

At decision the block 1818 the control system 510 may determine whether the frequency and/or severity of hypoglycemia events is increased during the last therapy period compared to the therapy period before the last therapy period. In some examples, if the control system 510 determines that the frequency and/or severity of hypoglycemia events is increased (e.g., beyond a threshold number or amount) during the last therapy period, the control system 510 may return to the block 1810 and continue providing therapy to the subject based on the last modified value of the control parameter without any further modification. If at decision block 1818, the control system determines that the change in frequency and/or severity of hypoglycemia events is negligible (e.g., below a threshold number or amount), the control system may proceed to the block 1808 where the control system 510 modifies the value of the control parameter. In some examples, the modified value may be a value that results in more aggressive therapy (e.g., the value of Tmax may be reduced). In some such examples, the amount by which the control parameter is changed may be smaller than a reduction amount in one or more previous modifications.

In some examples, at the block 1818 the control system may determine risks or the frequency and severity of one or more events other than hypoglycemia. For example, the control system may determine that in spite of an improvement in glycemic control for the subject, the rate and magnitude of glucose concentration has increased beyond threshold value. In some such examples, these additional risk determinations may be used to determine whether to keep or modify the last value of the control parameter.

In some embodiments, a modified version of the process 1800 may be used by the glucose control system wherein the process stops at block 1816 and the control system continues providing therapy based on the last modified value of the control parameter until a user input is received. In some such examples, the last value of the control parameter (modified at block 1808), the results of the comparative assessment generated based on the comparison performed at block 1814 (e.g., whether a statistically significant improvement in subject's glycemic control resulted from the last control parameter change), may be output to the subject, a guardian or a healthcare provider via a user interface of the glucose control system 510 and/or a computing system (e.g., a smartphone, a notebook a personal computer and the like) connected to the glucose control system (e.g., via a wireless link). In some such embodiments, at least in part based on the outcomes of the comparative assessment, the subject, the guardian or the healthcare provider may change the value of the corresponding control parameter (e.g., an interaction with a user interface) before the next therapy period.

In some examples, the statistical analysis used to determine the therapy effects (e.g., at blocks 1306 and 1312 in the process 1300, and bock 1806 and 1812 in the process 1800) or to compare between therapy effects (e.g., at block 1316 in the process 1300 and block 1814 in the process 1800), may include regression analysis. In some examples, regression analysis may be used to find a relation between parameters calculated and/or measured during the therapy period. For example, with reference to FIG. 17, a regression analysis may be used to find a relation between $U_j$ and the rate of glucose concentration change (e.g., using $G(t)$ near $t_i$) for a plurality of therapies provided during a therapy period. In some cases, the outcomes of one or more regression analysis may be used in the optimization process to determine a value of the control parameter.

In some examples, the therapy data captured and stored during one or more therapy periods may be divided to equal time intervals wherein each time interval starts and ends at substantially the same specific start and end times within a 24 period. In some such examples, an autoregression model may be derived for the glycemic control over the time interval between the specific start and end times. Subsequently, the resulting autoregression model may be used to determine whether the glycemic control has been improved compared to a previous therapy period. In some cases, the resulting autoregression model may be used to make additional adjustments to one or more control parameters in the subsequent therapy periods (after therapy periods following the period in which an autoregression model is determined).

In some examples, the outcome of the statistical analysis of therapy data may be used to evaluate the accuracy glucose signal generated by a CGM sensor.

As mentioned above in some examples the glucose control system may generate a control parameter optimization report that may include some or all of the statistical quantities calculated during the optimization process, outcomes of the statistical analysis and graphical representation of the therapy data and related risk assessments. In some such examples, a Control Variability-Grid Analysis (CVGA) may be included in the control parameter optimization report, to visualize the variability of CGM data at a group level from a glucose-control point of view. In some examples the graphs may comprise distinctive groups of graphs, for example, to visualize average glycemia and deviations from target values, visualize variability and risk assessment, and event-based clinical characteristics. In some other examples, the graphical data may represent average glycemia and deviations from target glucose trace and aggregated glucose trace representing the time spent below, within or above the preset target range and visualizing the crossing of glycemic thresholds. In yet other examples, the control parameter optimization report may include graphs representing variability and risk assessment data. For example, a risk trace may be presented to highlighting essential variance (e.g., by equalizing the size of glucose deviations towards hypo- and hyperglycemia, emphasizing large glucose excursions, and suppress fluctuation within target range). In some other examples, histogram of blood glucose rate of change may be included in the report to presented, for example, the spread and range of glucose transitions. In yet other examples, Poincare' plots may be included in the report to visualize the stability of the glucose signal during different therapy periods that may be also associated with different values of a control parameter.

Terminology

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware. Further, the computing system may include, be implemented as part of, or communicate with an automated blood glucose system, an ambulatory medicament system, or an ambulatory medical device.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A computer-implemented method of modifying therapy provided to a subject using a blood glucose control system, the method comprising:

by a hardware processor configured to generate a dose control signal for the blood glucose control system, receiving a glucose level signal from a glucose level sensor operatively connected to the subject;

causing first therapy to be delivered by the blood glucose control system to a subject during a first therapy period, wherein the first therapy is delivered based at least in part on a first value of a control parameter used by a control algorithm to generate the dose control signal, wherein the control parameter is used by the control algorithm to account for accumulation of insulin in the subject, thereby controlling an insulin dosing response of the control algorithm to a blood glucose excursion in the subject as indicated by the glucose level signal;

determining a first effect corresponding at least in part to the first therapy, wherein determining the first effect comprises analyzing glycemic control of blood glucose in the subject as indicated by the glucose level signal;

autonomously generating a second value of the control parameter, wherein the autonomously generated second value is determined as a function based on the first value and the first effect;

modifying the control parameter from the first value to the second value; and causing second therapy to be delivered by the blood glucose control system to the subject during a second therapy period, wherein the second therapy is delivered based at least in part on the second value of the control parameter, and wherein changing the control parameter modifies the therapy provided to the subject.

2. The computer-implemented method of claim 1, further comprising:

by the hardware processor, determining a second effect corresponding at least in part to the second therapy;

selecting one of the first value of the control parameter or the second value of the control parameter as an active control parameter value based at least in part on a comparison of the first effect and the second effect; and configuring the blood glucose control system to provide therapy to the subject during a third therapy period based at least in part on the active control parameter value, wherein the selection of the active control parameter value modifies the therapy provided to the subject.

3. The computer-implemented method of claim 1, wherein the control parameter used by the control algorithm relates to at least one time constant used in a calculation of an accumulation of insulin in the subject by the control algorithm.

4. The computer-implemented method of claim 1, wherein the control parameter used by the control algorithm corresponds to a rate of insulin diminishment in the subject.

5. The computer-implemented method of claim 1, wherein the first therapy period comprises a time period corresponding to the administering of multiple instances of therapy, and wherein the first therapy comprises the multiple instances of therapy.

6. The computer-implemented method of claim 1, wherein modifying the control parameter to the second value modifies one or more of a timing, a dosage size, or an administration rate of insulin administered during the second therapy period.

7. The computer-implemented method of claim 1, wherein the first value of the control parameter is based at least in part on one or more of therapy delivered during a time period prior to the first therapy period, a clinical value, or a body mass of the subject.

8. The computer-implemented method of claim 1, wherein the control parameter used by the control algorithm corresponds to a time until insulin within blood plasma of the subject reaches a particular concentration level subsequent to administration of an insulin dose.

9. A computer-implemented method of modifying therapy provided to a subject using a blood glucose control system, the method comprising:

by a hardware processor configured to generate a dose control signal for the blood glucose control system, causing first therapy to be delivered by the blood glucose control system to a subject during a first therapy period, wherein the first therapy is delivered based at least in part on a first value of a control parameter used by a control algorithm to generate the dose control signal;

determining a first effect corresponding at least in part to the first therapy, wherein determining the first effect comprises receiving a glucose level signal from a glucose level sensor operatively connected to the subject;

autonomously generating a second value of the control parameter based at least in part on a baseline value of the control parameter and an output of a function defined based on glycemic control of the subject, wherein the glucose level signal comprises an indication of the glycemic control of the subject during the first therapy period;

modifying the control parameter from the first value to the second value; and causing second therapy to be delivered by the blood glucose control system to the subject during a second therapy period, wherein the second therapy is delivered based at least in part on the second value of the control parameter, and wherein changing the control parameter modifies the therapy provided to the subject.

10. The computer-implemented method of claim 9, further comprising:

by the hardware processor, determining a second effect corresponding at least in part to the second therapy;

selecting one of the first value of the control parameter or the second value of the control parameter as an active control parameter value based at least in part on a comparison of the first effect and the second effect; and configuring the blood glucose control system to provide therapy to the subject during a third therapy period based at least in part on the active control parameter value, wherein the selection of the active control parameter value modifies the therapy provided to the subject.

11. The computer-implemented method of claim 9, wherein the first therapy comprises multiple instances of therapy administered over the first therapy period.

12. The computer-implemented method of claim 9, wherein the control parameter used by the control algorithm corresponds to a time until insulin within blood of the subject reaches a particular concentration level attributable to administration of an insulin dose.

13. A computer-implemented method of modifying therapy provided to a subject using a blood glucose control system, the method comprising:
- by a hardware processor configured to generate a dose control signal for the blood glucose control system,
  - causing first therapy to be delivered by the blood glucose control system to a subject during a first therapy period, wherein the first therapy is delivered based at least in part on a first value of a control parameter used by a control algorithm to generate the dose control signal;
  - determining a first effect corresponding at least in part to the first therapy, wherein determining the first effect comprises receiving a glucose level signal from a glucose level sensor operatively connected to the subject;
  - autonomously generating a second value of the control parameter, wherein the autonomously generated second value is determined as a function based at least in part on a baseline value;
  - modifying the control parameter from the first value to the second value;
  - causing second therapy to be delivered by the blood glucose control system to the subject during a second therapy period, wherein the second therapy is delivered based at least in part on the second value of the control parameter, and wherein changing the control parameter modifies the therapy provided to the subject;
  - determining a second effect corresponding at least in part to the second therapy;
  - autonomously performing a comparison of the first effect and the second effect without action by a human;
  - selecting one of the first value of the control parameter or the second value of the control parameter as an active control parameter value based at least in part on the comparison of the first effect and the second effect; and
  - configuring the blood glucose control system to provide therapy to the subject during a third therapy period based at least in part on the active control parameter value, wherein the selection of the active control parameter value modifies the therapy provided to the subject.

14. The computer-implemented method of claim 13, wherein the second value of the control parameter is based at least in part on glycemic control indicated by the glucose level signal.

15. The computer-implemented method of claim 13, wherein the baseline value comprises the first value of the control parameter.

16. The computer-implemented method of claim 13, wherein the first value of the control parameter is determined based at least in part on the baseline value.

17. The computer-implemented method of claim 13, further comprising performing the comparison of the first effect and the second effect, wherein the comparison is performed substantially in real-time in response to determining the second effect.

18. The computer-implemented method of claim 13, further comprising performing the comparison of the first effect and the second effect, wherein the comparison of the first effect and the second effect comprises performing a statistical comparison of the first effect and the second effect.

19. The computer-implemented method of claim 13, further comprising performing the comparison of the first effect and the second effect, wherein the comparison of the first effect and the second effect comprises performing regression analysis of at least the first effect and the second effect.

20. The computer-implemented method of claim 13, wherein the second value of the control parameter may be selected based on performance of a regression analysis between a time of absorption of subcutaneously administered insulin into blood of the subject and a glycemic control function, wherein the glycemic control function is based at least in part on the glucose level signal.

21. An automated blood glucose control system configured to autonomously modify a control parameter used by a control algorithm to generate a dose control signal that causes therapy to be provided to a subject, the automated blood glucose control system comprising:
- a medicament delivery interface configured to operatively connect to a medicament pump for infusing medicament into the subject;
- a memory configured to store specific computer-executable instructions and therapy data; and
- a hardware processor in communication with the memory and configured to execute the specific computer-executable instructions to at least:
  - receive a glucose level signal from a glucose level sensor operatively connected to the subject;
  - cause first therapy to be delivered to the subject during a first therapy period, wherein the first therapy is delivered based at least in part on a first value of the control parameter used by the control algorithm to generate the dose control signal, wherein the control parameter is used by the control algorithm to account for accumulation of insulin in the subject, thereby controlling an insulin dosing response of the control algorithm to a blood glucose excursion in the subject as indicated by the glucose level signal;
  - determine a first effect corresponding at least in part to the first therapy, wherein determining the first effect comprises analyzing glycemic control of blood glucose in the subject as indicated by the glucose level signal;
  - autonomously generate a second value of the control parameter, wherein the autonomously generated second value is determined as a function based on the first value and the first effect;
  - modify the control parameter from the first value to the second value; and
  - cause second therapy to be delivered to the subject during a second therapy period, wherein the second therapy is delivered based at least in part on the second value of the control parameter, and wherein changing the control parameter modifies the therapy provided to the subject.

22. The automated blood glucose control system of claim 21, wherein the hardware processor is further configured to execute the specific computer-executable instructions to at least:
- determine a second effect corresponding at least in part to the second therapy;
- select one of the first value of the control parameter or the second value of the control parameter as an active control parameter value based at least in part on a comparison of the first effect and the second effect; and
- provide therapy to the subject during a third therapy period based at least in part on the active control parameter value, wherein the selection of the active control parameter value modifies the therapy provided to the subject.

23. The automated blood glucose control system of claim 21, wherein the control parameter used by the control algorithm relates to at least one time constant used in a calculation of an accumulation of insulin in the subject by the control algorithm.

24. The automated blood glucose control system of claim 21, wherein the control parameter used by the control algorithm corresponds to a rate of insulin diminishment in the subject.

25. The automated blood glucose control system of claim 21, wherein the first therapy period comprises a time period corresponding to the administering of multiple instances of therapy, and wherein the first therapy comprises the multiple instances of therapy.

26. The automated blood glucose control system of claim 21, wherein modifying the control parameter to the second value modifies one or more of a timing, a dosage size, or a rate of administration of insulin administered during the second therapy period.

27. The automated blood glucose control system of claim 21, wherein the first value of the control parameter is based at least in part on one or more of therapy delivered during a time period prior to the first therapy period, a clinical value, or a body mass of the subject.

28. The automated blood glucose control system of claim 21, wherein the control parameter used by the control algorithm corresponds to a time until insulin within blood plasma of the subject reaches a particular concentration level subsequent to administration of an insulin dose.

29. The automated blood glucose control system of claim 21, wherein the control parameter corresponds to Tmax or $T_{1/2}$.

* * * * *

UNITED STATES PATENT AND TRADEMARK OFFICE
CERTIFICATE OF CORRECTION

PATENT NO. : 11,116,902 B2
APPLICATION NO. : 17/061927
DATED : September 14, 2021
INVENTOR(S) : Firas H. El-Khatib et al.

Page 1 of 1

It is certified that error appears in the above-identified patent and that said Letters Patent is hereby corrected as shown below:

In the Specification

At Column 1, Lines 9 and 10, delete "Agreement No. W912CG20C0013, awarded by Defense Advanced Research Projects Agency" and insert --Contract No. DK120234, awarded by the National Institutes of Health--

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*